(12) United States Patent
Choi et al.

(10) Patent No.: US 11,963,440 B2
(45) Date of Patent: Apr. 16, 2024

(54) COMPOUND AND PHOTOELECTRIC DEVICE, IMAGE SENSOR, AND ELECTRONIC DEVICE INCLUDING THE SAME

(71) Applicant: Samsung Electronics Co., Ltd., Suwon-si (KR)

(72) Inventors: Taejin Choi, Suwon-si (KR); Jeong Il Park, Seongnam-si (KR); Jisoo Shin, Suwon-si (KR); Sung Young Yun, Suwon-si (KR); Seon-Jeong Lim, Yongin-si (KR); Youn Hee Lim, Suwon-si (KR); Yeong Suk Choi, Suwon-si (KR); Hye Rim Hong, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 792 days.

(21) Appl. No.: 17/065,816

(22) Filed: Oct. 8, 2020

(65) Prior Publication Data
US 2021/0111353 A1 Apr. 15, 2021

(30) Foreign Application Priority Data

Oct. 10, 2019 (KR) .................. 10-2019-0125543

(51) Int. Cl.
| | |
|---|---|
| H01L 51/00 | (2006.01) |
| C07D 421/04 | (2006.01) |
| C07D 421/06 | (2006.01) |
| C07D 421/14 | (2006.01) |
| H10K 85/60 | (2023.01) |
| H10K 19/20 | (2023.01) |
| H10K 30/30 | (2023.01) |
| H10K 39/32 | (2023.01) |

(52) U.S. Cl.
CPC ......... *H10K 85/657* (2023.02); *C07D 421/04* (2013.01); *C07D 421/06* (2013.01); *C07D 421/14* (2013.01); *H10K 85/636* (2023.02); *H10K 85/654* (2023.02); *H10K 19/20* (2023.02); *H10K 30/30* (2023.02); *H10K 39/32* (2023.02)

(58) Field of Classification Search
None
See application file for complete search history.

(56) References Cited

U.S. PATENT DOCUMENTS

| | | | |
|---|---|---|---|
| 5,206,375 A | 4/1993 | Schefczik et al. | |
| 8,525,577 B2 | 9/2013 | Yofu et al. | |
| 9,786,847 B2 | 10/2017 | Lim et al. | |
| 9,818,956 B2 | 11/2017 | Ro et al. | |
| 9,941,477 B2 | 4/2018 | Choi et al. | |
| 10,224,486 B2 | 3/2019 | Yagi et al. | |
| 10,236,449 B2 | 3/2019 | Yun et al. | |
| 10,276,802 B2 | 4/2019 | Shibuya et al. | |
| 10,326,083 B2 | 6/2019 | Yagi et al. | |
| 10,461,256 B2 | 10/2019 | Choi et al. | |
| 10,566,544 B2 | 2/2020 | Shibuya et al. | |
| 2009/0281145 A1 | 11/2009 | Baraldi et al. | |
| 2016/0155954 A1 | 6/2016 | Lim et al. | |

FOREIGN PATENT DOCUMENTS

| | | |
|---|---|---|
| EP | 193885 A1 | 9/1986 |
| EP | 3243822 A1 | 11/2017 |
| EP | 3473622 A1 | 4/2019 |
| KR | 20160046567 A | 4/2016 |
| KR | 20160052448 A | 5/2016 |
| KR | 20160062527 A | 6/2016 |
| KR | 20170037390 A | 4/2017 |
| KR | 20170060488 A | 6/2017 |
| KR | 20170114839 A | 10/2017 |
| KR | 20170126753 A | 11/2017 |
| KR | 20170137648 A | 12/2017 |
| WO | WO-2018140578 A1 | 8/2018 |

OTHER PUBLICATIONS

Chemical Abstract Registry No. 333409-88-4, indexed in the Registry File on STN CAS Online Apr. 30, 2001.*

Hokuto Seo et al., 'Color Sensors with Three Vertically Stacked Organic Photodetectors' *Japanese Journal of Applied Physics*, vol. 46, No. 49, 2007, pp. L1240-L1242.

Satoshi Aihara et al., 'Stacked Image Sensor With Green- and Red-Sensitive Organic Photoconductive Films Applying Zinc Oxide Thin-Film Transistors to a Signal Readout Circuit' *IEEE Transactions on Electron Devices*, vol. 56, No. 11, Nov. 2009, pp. 2570-2576.

Mikio Ihama et al., 'CMOS Image Sensor with a Thin Overlaid Panchromatic Organic Photoconductive Layer for Sensors with Reduced Pixel Size' *IDW*, 2009, pp. 2123-2126.

(Continued)

*Primary Examiner* — Po-Chih Chen
(74) *Attorney, Agent, or Firm* — HARNESS, DICKEY & PIERCE, P.L.C.

(57) ABSTRACT

A compound of Chemical Formula 1, and an organic photoelectric device, an image sensor, and an electronic device including the same are disclosed:

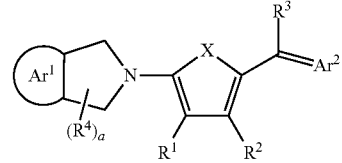

[Chemical Formula 1]

In Chemical Formula 1, the definition of each group and parameter is as described in the detailed description.

24 Claims, 10 Drawing Sheets

(56) References Cited

OTHER PUBLICATIONS

Seon-Jeong Lim et al., 'Organic-on-silicon complementary metal-oxide-semiconductor colour image sensors' *Scientific Reports*, 5:7708, Jan. 2015.
Juha Alakarhu, 'Image Sensors and Image Quality in Mobile Phones' *International Image Sensor Workshop*, Jun. 2007.
Extended European Search Report dated Jan. 27, 2021, issued in corresponding European Patent Application No. 20200840.5.

* cited by examiner

COMPOUND AND PHOTOELECTRIC DEVICE, IMAGE SENSOR, AND ELECTRONIC DEVICE INCLUDING THE SAME

CROSS-REFERENCE TO RELATED APPLICATION

This application claims priority to and the benefit of Korean Patent Application No. 10-2019-0125543 filed in the Korean Intellectual Property Office on Oct. 10, 2019, the entire contents of which are incorporated herein by reference.

BACKGROUND

1. Field

Example embodiments provide a compound and a photoelectric device, an image sensor, and/or an electronic device including the same.

2. Description of Related Art

A photoelectric device converts light into an electrical signal using photoelectric effects. The photoelectric device may include a photodiode, a phototransistor, and the like, and it may be applied to an image sensor, an organic light emitting diode, and the like.

An image sensor including the photodiode is getting higher in resolution day by day, and accordingly, a pixel size is getting smaller. At present, a silicon photodiode is widely used, but it has a problem of deteriorated sensitivity since silicon photodiode has a smaller absorption area due to small pixels. Accordingly, an organic material that is capable of replacing silicon has been researched.

The organic material has a high absorption coefficient and selectively absorbs light in a particular wavelength region depending on a molecular structure, and thus may simultaneously replace a photodiode and a color filter and resultantly improve sensitivity and contribute to high integration.

SUMMARY

Example embodiments provide a compound capable of selectively absorbing light in a green wavelength region and having improved thermal stability.

Example embodiments also provide a photoelectric device (e.g., organic photoelectric device) capable of selectively absorbing light in the green wavelength region and maintaining good efficiency even under high temperature conditions.

Example embodiments also provide an image sensor including the photoelectric device (e.g., organic photoelectric device).

Example embodiments also provide an electronic device including the image sensor.

According to example embodiments, a compound is represented by Chemical Formula 1.

[Chemical Formula 1]

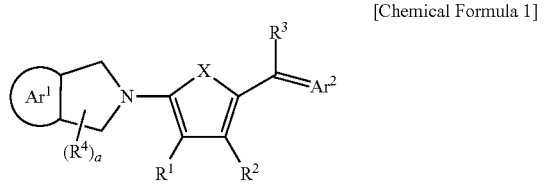

In Chemical Formula 1,

Ar$^1$ is a substituted or unsubstituted C6 to C30 arene group, a substituted or unsubstituted C3 to C30 heteroarene group, or a condensed ring thereof, X is O, S, Se, Te, S(=O), S(=O)$_2$, NR$^a$, SiR$^b$R$^c$, GeR$^d$R$^e$, or CR$^f$R$^g$ (wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure), Ar$^2$ is a substituted or unsubstituted C6 to C30 hydrocarbon ring group having at least one functional group selected from C=O, C=S, C=Se, and C=Te, a substituted or unsubstituted C2 to C30 heterocyclic group having at least one functional group selected from C=O, C=S, C=Se, and C=Te, or a fused ring group thereof, R$^1$ to R$^3$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, a pentafluorosulfanyl group (—SF$_5$), a hydroxyl group, an amine group, a hydrazine group, a hydrazone group, a carboxyl group or a salt thereof, a sulfonic acid group or a salt thereof, a phosphoric acid group or a salt thereof, —SiR$^a$R$^b$R$^c$ (wherein R$^a$, R$^b$, and R$^c$ are independently hydrogen or a substituted or unsubstituted C1 to C10 alkyl group), or a combination thereof, R$^4$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a is an integer of 0 to 4.

In some embodiments, the compound may be represented by Chemical Formula 2-1.

[Chemical Formula 2-1]

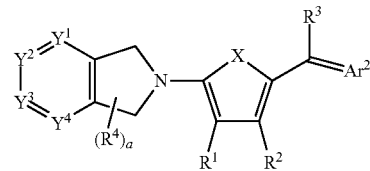

In Chemical Formula 2-1,

Y$^1$ to Y$^4$ are independently N or CR$^p$, wherein R$^p$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group or adjacent CR$^p$'s are linked to each other to form a substituted or unsubstituted C6 to C30 arene group, a substituted or unsubstituted C3 to C30 heteroarene group, or a condensed ring thereof, X is O, S, Se, Te, S(=O), S(=O)$_2$, NR$^a$, SiR$^b$R$^c$, GeR$^d$R$^e$, or CR$^f$R$^g$ (wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), $Ar^2$ is a substituted or unsubstituted C6 to C30 hydrocarbon ring group including at least one functional group selected from C=O, C=S, C=Se, and C=Te, a substituted or unsubstituted C2 to C30 heterocyclic group including at least one functional group selected from C=O, C=S, C=Se, and C=Te, or a fused ring group thereof, $R^1$ to $R^3$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, a pentafluorosulfanyl group (—SF$_5$), a hydroxyl group, an amine group, a hydrazine group, a hydrazone group, a carboxyl group or a salt thereof, a sulfonic acid group or a salt thereof, a phosphoric acid group or a salt thereof, —SiR$^a$R$^b$R$^c$ (wherein $R^a$, $R^b$, and $R^c$ are independently hydrogen or a substituted or unsubstituted C1 to C10 alkyl group), or a combination thereof, $R^4$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a is an integer of 0 to 4.

In some embodiments, the compound may be represented by Chemical Formula 2-2.

[Chemical Formula 2-2]

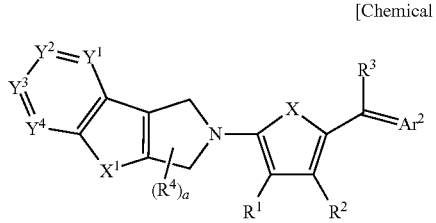

In Chemical Formula 2-2,

X is O, S, Se, Te, S(=O), S(=O)$_2$, NR$^a$, SiR$^b$R$^c$, GeR$^d$R$^e$, or CR$^f$R$^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), $X^1$ is O, S, Se, Te, S(=O), S(=O)$_2$, NR$^a$, SiR$^b$R$^c$, GeR$^d$R$^e$, or CR$^f$R$^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), $Ar^2$ is a substituted or unsubstituted C6 to C30 hydrocarbon ring group having at least one functional group selected from C=O, C=S, C=Se, and C=Te, a substituted or unsubstituted C2 to C30 heterocyclic group having at least one functional group selected from C=O, C=S, C=Se, and C=Te, or a fused ring group thereof, $R^1$ to $R^3$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, a pentafluorosulfanyl group (—SF$_5$), a hydroxyl group, an amine group, a hydrazine group, a hydrazone group, a carboxyl group or a salt thereof, a sulfonic acid group or a salt thereof, a phosphoric acid group or a salt thereof, —SiR$^a$R$^b$R$^c$ (wherein $R^a$, $R^b$, and $R^c$ are independently hydrogen or a substituted or unsubstituted C1 to C10 alkyl group), or a combination thereof, $R^4$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a is an integer of 0 to 4, and $Y^1$ to $Y^4$ are independently N or CR$^p$, wherein $R^p$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group or adjacent CR$^p$'s are linked to each other to form a substituted or unsubstituted C6 to C30 arene group, a substituted or unsubstituted C3 to C30 heteroarene group, or a condensed ring thereof.

In some embodiments, the compound may be represented by Chemical Formula 2-3.

[Chemical Formula 2-3]

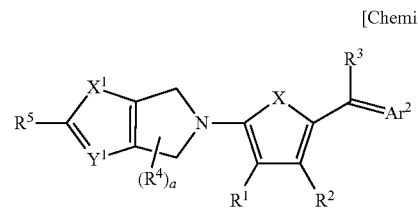

In Chemical Formula 2-3,

X is O, S, Se, Te, S(=O), S(=O)$_2$, NR$^a$, SiR$^b$R$^c$, GeR$^d$R$^e$, or CR$^f$R$^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), $X^1$ is O, S, Se, Te, S(=O), S(=O)$_2$, NR$^a$, SiR$^b$R$^c$, GeR$^d$R$^e$, or CR$^f$R$^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), $Ar^2$ is a substituted or unsubstituted C6 to C30 hydrocarbon ring group having at least one functional group selected from C=O, C=S, C=Se, and C=Te, a substituted or unsubstituted C2 to C30 heterocyclic group having at least one functional group selected from C=O, C=S, C=Se, and C=Te, or a fused ring group thereof, $R^1$ to $R^3$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, a pentafluorosulfanyl group (—$SF_5$), a hydroxyl group, an amine group, a hydrazine group, a hydrazone group, a carboxyl group or a salt thereof, a sulfonic acid group or a salt thereof, a phosphoric acid group or a salt thereof, —$SiR^aR^bR^c$ (wherein $R^a$, $R^b$, and $R^c$ are independently hydrogen or a substituted or unsubstituted C1 to C10 alkyl group), or a combination thereof, $R^4$ and $R^5$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a is an integer of 0 to 4, and $Y^1$ is N or $CR^p$, wherein $R^p$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group or $R^p$ and $R^5$ are linked to each other to form a substituted or unsubstituted C6 to C30 arene group, a substituted or unsubstituted C3 to C30 heteroarene group, or a condensed ring thereof.

In some embodiments, the compound may be represented by one of Chemical Formulas 2-1A to 2-1E.

[Chemical Formula 2-1A]

![Chemical Formula 2-1A structure]

In Chemical Formula 2-1A,

X, $Ar^2$, $R^1$ to $R^4$, and a are the same as in Chemical Formula 2-1, $R^{11}$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 is an integer of 0 to 4.

[Chemical Formula 2-1B]

![Chemical Formula 2-1B structure]

In Chemical Formula 2-1B,

X, $Ar^2$, $R^1$ to $R^4$, and a are the same as in Chemical Formula 2-1, $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a1 is an integer of 0 to 4, and a2 is an integer of 0 to 2.

[Chemical Formula 2-1C]

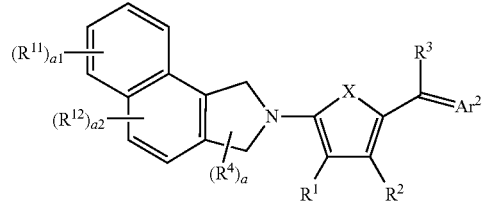

In Chemical Formula 2-1C,

X, $Ar^2$, $R^1$ to $R^4$, and a are the same as in Chemical Formula 2-1, $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a1 is an integer of 0 to 4, and a2 is an integer of 0 to 2.

[Chemical Formula 2-1D]

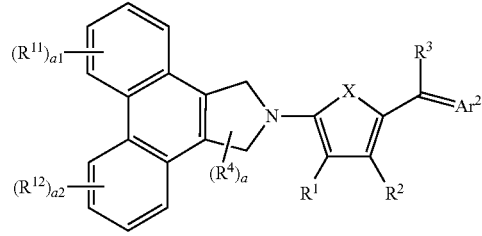

In Chemical Formula 2-1D,

X, $Ar^2$, $R^1$ to $R^4$, and a are the same as in Chemical Formula 2-1, $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer ranging from 0 to 4.

[Chemical Formula 2-1E]

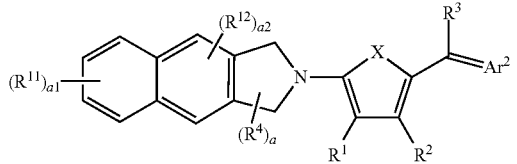

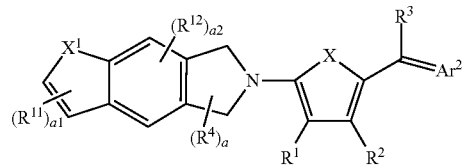

In Chemical Formula 2-1E,

X, $Ar^2$, $R^1$ to $R^4$, and a are the same as in Chemical Formula 2-1, $X^1$ is O, S, Se, Te, S(=O), S(=O)$_2$, $NR^a$, $SiR^bR^c$, $GeR^dR^e$, or $CR^fR^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer of 0 to 2.

In some embodiments, the compound may be represented by one of Chemical Formulas 2-2A to 2-2J.

[Chemical Formula 2-2A]

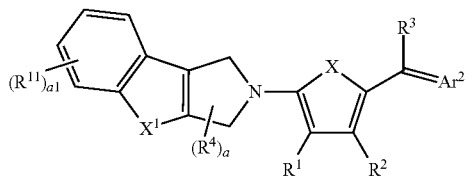

In Chemical Formula 2-2A,

X, $X^1$, $Ar^2$, $R^1$ to $R^4$, and a are the same as in Chemical Formula 2-2, $R^{11}$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 is an integer of 0 to 4.

[Chemical Formula 2-2B]

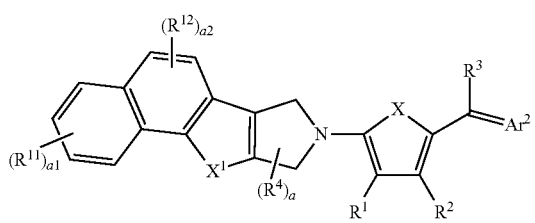

In Chemical Formula 2-2B,

X, $X^1$, $Ar^2$, $R^1$ to $R^4$, and a are the same as in Chemical Formula 2-2, $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a1 is an integer of 0 to 4, and a2 is an integer of 0 to 2.

[Chemical Formula 2-2C]

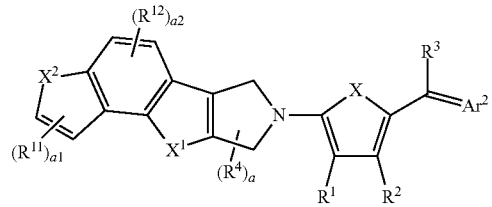

In Chemical Formula 2-2C,

X, $X^1$, $Ar^2$, $R^1$ to $R^4$, and a are the same as in Chemical Formula 2-2, $X^2$ is O, S, Se, Te, S(=O), S(=O)$_2$, $NR^a$, $SiR^bR^c$, $GeR^dR^e$, or $CR^fR^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer of 0 to 2.

[Chemical Formula 2-2D]

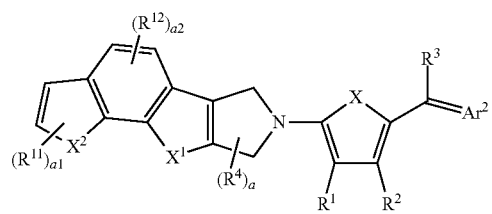

In Chemical Formula 2-2D,

X, $X^1$, $Ar^2$, $R^1$ to $R^4$, and a are the same as in Chemical Formula 2-2, $X^2$ is O, S, Se, Te, S(=O), S(=O)$_2$, $NR^a$, $SiR^bR^c$, $GeR^dR^e$, or $CR^fR^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer of 0 to 2.

[Chemical Formula 2-2E]

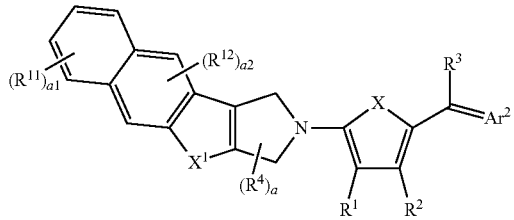

In Chemical Formula 2-2E,
X, $X^1$, $Ar^2$, $R^1$ to $R^4$, and a are the same as in Chemical Formula 2-2,
$R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group,
a1 is an integer of 0 to 4, and
a2 is an integer of 0 to 2.

[Chemical Formula 2-2F]

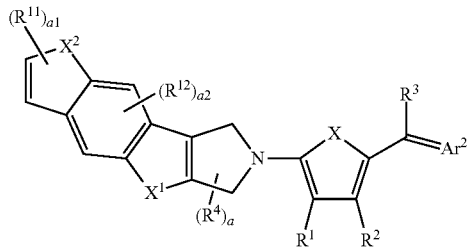

In Chemical Formula 2-2F,
X, $X^1$, $Ar^2$, $R^1$ to $R^4$, and a are the same as in Chemical Formula 2-2,
$X^2$ is O, S, Se, Te, S(=O), S(=O)$_2$, $NR^a$, $SiR^bR^c$, $GeR^dR^e$, or $CR^fR^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure),
$R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and
a1 and a2 are independently an integer of 0 to 2.

[Chemical Formula 2-2G]

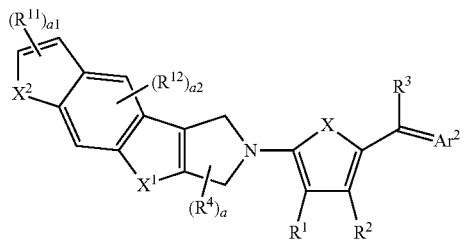

In Chemical Formula 2-2G,
X, $X^1$, $Ar^2$, $R^1$ to $R^4$, and a are the same as in Chemical Formula 2-2,
$X^2$ is O, S, Se, Te, S(=O), S(=O)$_2$, $NR^a$, $SiR^bR^c$, $GeR^dR^e$, or $CR^fR^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure),
$R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and
a1 and a2 are independently an integer of 0 to 2.

[Chemical Formula 2-2H]

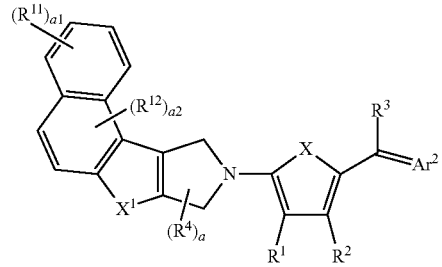

In Chemical Formula 2-2H,
X, $X^1$, $Ar^2$, $R^1$ to $R^4$, and a are the same as in Chemical Formula 2-2,
$R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group,
a1 is an integer of 0 to 4, and
a2 is an integer of 0 to 2.

[Chemical Formula 2-2I]

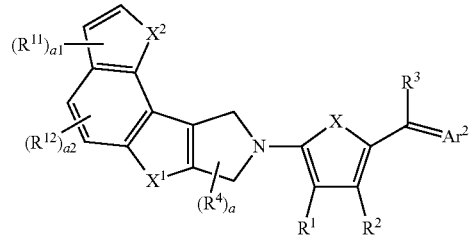

In Chemical Formula 2-2I,
X, $X^1$, $Ar^2$, $R^1$ to $R^4$, and a are the same as in Chemical Formula 2-2,
$X^2$ is O, S, Se, Te, S(=O), S(=O)$_2$, $NR^a$, $SiR^bR^c$, $GeR^dR^e$, or $CR^fR^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer of 0 to 2.

[Chemical Formula 2-2J]

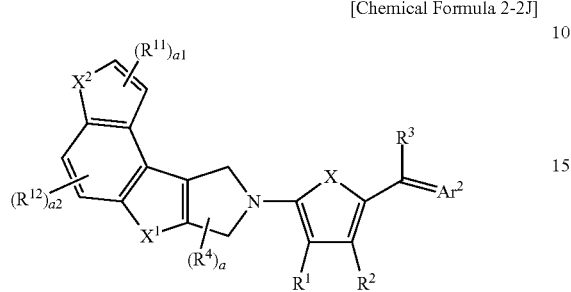

In Chemical Formula 2-2J,

X, $X^1$, $Ar^2$, $R^1$ to $R^4$, and a are the same as in Chemical Formula 2-2, $X^2$ is O, S, Se, Te, S(=O), S(=O)$_2$, $NR^a$, $SiR^bR^c$, $GeR^dR^e$, or $CR^fR^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer of 0 to 2.

In some embodiments, the compound represented by Chemical Formula 2-3 may be represented by one of Chemical Formulas 2-3A to 2-3D.

[Chemical Formula 2-3A]

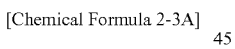
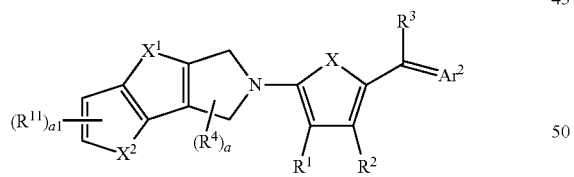

In Chemical Formula 2-3A,

X, $X^1$, $Ar^2$, $R^1$ to $R^4$, and a are the same as in Chemical Formula 2-3, $X^2$ is O, S, Se, Te, S(=O), S(=O)$_2$, $NR^a$, $SiR^bR^c$, $GeR^dR^e$, or $CR^fR^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), $R^{11}$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 is an integer of 0 to 2.

[Chemical Formula 2-3B]

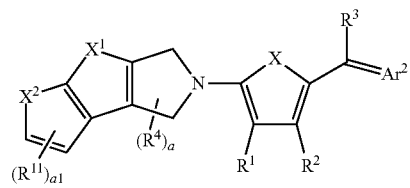

In Chemical Formula 2-3B,

X, $X^1$, $Ar^2$, $R^1$ to $R^4$, and a are the same as in Chemical Formula 2-3, $X^2$ is O, S, Se, Te, S(=O), S(=O)$_2$, $NR^a$, $SiR^bR^c$, $GeR^dR^e$, or $CR^fR^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), $R^{11}$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 is an integer of 0 to 2.

[Chemical Formula 2-3C]

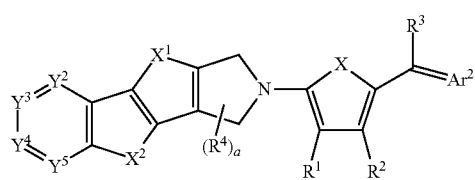

In Chemical Formula 2-3C,

X, $X^1$, $Ar^2$, $R^1$ to $R^4$, and a are the same as in Chemical Formula 2-3, $X^2$ is O, S, Se, Te, S(=O), S(=O)$_2$, $NR^a$, $SiR^bR^c$, $GeR^dR^e$, or $CR^fR^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), and $Y^2$ to $Y^5$ are independently N or $CR^p$, wherein $R^p$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group or adjacent $CR^p$'s are linked to each other to form a substituted or unsubstituted C6 to C30 arene group, a substituted or unsubstituted C3 to C30 heteroarene group, or a condensed ring thereof.

[Chemical Formula 2-3D]

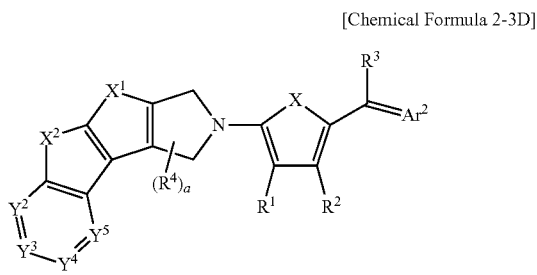

In Chemical Formula 2-3D,

X, $X^1$, $Ar^2$, $R^1$ to $R^4$, and a are the same as in Chemical Formula 2-3, $X^2$ is O, S, Se, Te, S(=O), S(=O)$_2$, $NR^a$, $SiR^bR^c$, $GeR^dR^e$, or $CR^fR^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), and $Y^2$ to $Y^5$ are independently N or $CR^p$, wherein $R^p$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group or adjacent $CR^p$'s are linked to each other to form a substituted or unsubstituted C6 to C30 arene group, a substituted or unsubstituted C3 to C30 heteroarene group, or a condensed ring thereof.

In some embodiments, in Chemical Formula 1, $Ar^2$ may be a ring group represented by Chemical Formula 3.

[Chemical Formula 3]

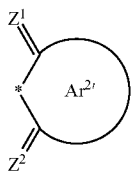

In Chemical Formula 3, $Ar^{2'}$ is a substituted or unsubstituted C6 to C30 aryl group or a substituted or unsubstituted C3 to C30 heteroaryl group, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group.

In some embodiments, in Chemical Formula 1, $Ar^2$ may be a ring group represented by one of Chemical Formulas 4A to 4F.

[Chemical Formula 4A]

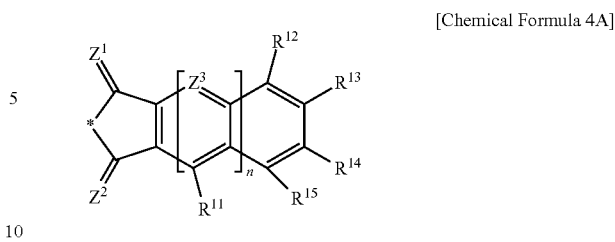

In Chemical Formula 4A, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group, $Z^3$ is N or $CR^c$ (wherein $R^c$ is hydrogen, deuterium, or a substituted or unsubstituted C1 to C10 alkyl group), $R^{11}$, $R^{12}$, $R^{13}$, $R^{14}$, and $R^{15}$ are the same or different and are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, wherein $R^{12}$ and $R^{13}$ and $R^{14}$ and $R^{15}$ are independently present or are linked to each other to form a fused aromatic ring, n is 0 or 1, and

* is a linking portion.

[Chemical Formula 4B]

In Chemical Formula 4B, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group, $Z^3$ is O, S, Se, Te, or $C(R^a)(CN)$ (wherein $R^a$ is hydrogen, a cyano group (—CN), or a C1 to C10 alkyl group), $R^{11}$ and $R^{12}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking portion.

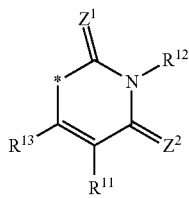

[Chemical Formula 4C]

In Chemical Formula 4C, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking portion.

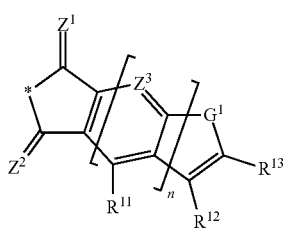

[Chemical Formula 4D]

In Chemical Formula 4D, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group, $Z^3$ is N or $CR^c$ (wherein $R^c$ is hydrogen or a substituted or unsubstituted C1 to C10 alkyl group), $G^1$ is O, S, Se, Te, $SiR^xR^y$, or $GeR^zR^w$, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, wherein $R^{12}$ and $R^{13}$ are independently present or are linked to each other to form an aromatic ring, n is 0 or 1, and

* is a linking portion.

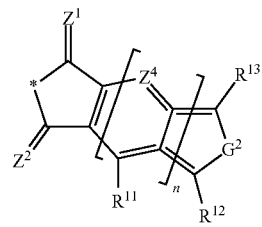

[Chemical Formula 4E]

In Chemical Formula 4E, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group, $Z^4$ is $NR^a$, $CR^bR^c$, O, S, Se, Te, S(=O), S(=O)$_2$, $SiR^dR^e$ and $GeR^fR^g$ (wherein $R^a$, $R^b$, $R^c$, $R^d$, $R^e$, $R^d$, $R^e$, $R^f$ and $R^g$ is hydrogen or a substituted or unsubstituted C1 to C10 alkyl group), $G^2$ is O, S, Se, Te, $SiR^xR^y$, or $GeR^zR^w$, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, n is 0 or 1, and

* is a linking portion.

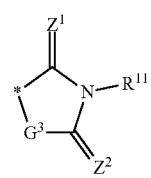

[Chemical Formula 4F]

In Chemical Formula 4F, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group, $R^{11}$ is hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^3$ is O, S, Se, Te, $SiR^xR^y$, or $GeR^zR^w$, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group.

In some embodiments, $Ar^2$ may be the ring group represented by Chemical Formula 4A and $Ar^2$ may be represented by one of Chemical Formulas 4A-1, 4A-2, or 4A-3,

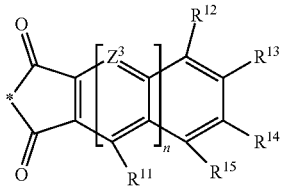

[Chemical Formula 4A-1]

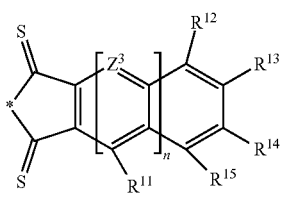

[Chemical Formula 4A-2]

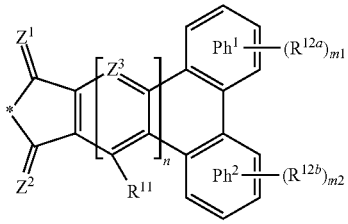

[Chemical Formula 4A-3]

In Chemical Formulas 4A-1 and 4A-2, $Z^3$, $R^{11}$, n, $R^{12}$, $R^{13}$, $R^{14}$, and $R^{15}$ are the same as in Chemical Formula 4A, and in Chemical Formula 4A-3, $Z^1$, $Z^2$, $Z^3$, $R^{11}$, and n are the same as in Chemical Formula 4A, $R^{12a}$ and $R^{12b}$ are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, m1 and m2 are independently an integer of 0 to 4, and $Ph^1$ and $Ph^2$ are a fused phenylene ring.

In some embodiments, $Ar^2$ may be the ring group represented by Chemical Formula 4B and $Ar^2$ may represented by one of Chemical Formulas 4B-1, 4B-2, or 4B-3,

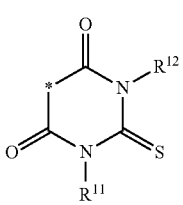

[Chemical Formula 4B-1]

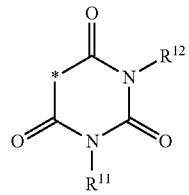

[Chemical Formula 4B-2]

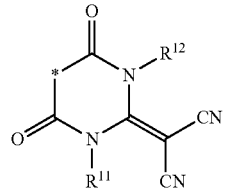

[Chemical Formula 4B-3]

In Chemical Formulas 4B-1, 4B-2, and 4B-3, $R^{11}$ and $R^{12}$ are the same as in Chemical Formula 4B.

In some embodiments, $Ar^2$ may be the ring group represented by Chemical Formula 4C and $Ar^2$ may be represented by one of Chemical Formulas 4C-1 or 4C-2,

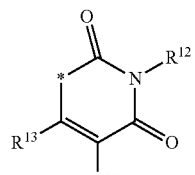

[Chemical Formula 4C-1]

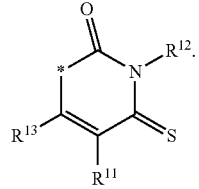

[Chemical Formula 4C-2]

In Chemical Formulas 4C-1 and 4C-2, $R^{11}$ to $R^{13}$ are the same as in Chemical Formula 4C.

In some embodiments, the compound represented by Chemical Formula 1 may have an aspect ratio (Z/X) obtained by dividing a shortest length (Z) by a longest length (X) in a range of less than or equal to about 0.30.

In some embodiments, the compound may have a maximum absorption wavelength ($\lambda_{max}$) in a wavelength range of greater than or equal to about 500 nm and less than or equal to about 580 nm, for example greater than or equal to about 520 nm and less than or equal to about 555 nm in a thin film state.

In some embodiments, the compound may exhibit a light absorption curve having a full width at half maximum (FWHM) of about 50 nm to about 100 nm.

In some embodiments, the compound may be a p-type semiconductor compound, the compound may have a HOMO energy level ranging from about 5.2 eV to about 5.8 eV and an energy bandgap ranging from about 2.12 eV to about 2.48 eV, the LUMO energy level of the compound may be in a range of about 3.7 eV to about 2.7 eV, and the compound may have a molecular weight of about 300 g/mol to about 1500 g/mol.

In some embodiments, the compound may be represented by Chemical Formula 1A or Chemical Formula 1B,

[Chemical Formula 1A]

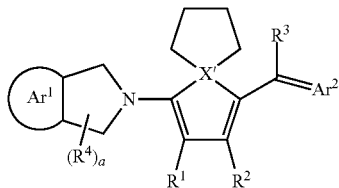

[Chemical Formula 1B]

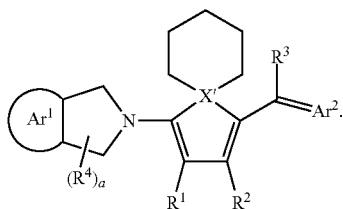

In Chemical Formulas 1A and 1B,
Ar$^1$, Ar$^2$, R$^1$ to R$^4$, and a are the same as in Chemical Formula 1, and
X' is Si, Ge, or C.

According to another embodiment, a photoelectric device (e.g., organic photoelectric device) includes a first electrode and a second electrode facing each other and an active layer interposed between the first electrode and the second electrode and including the compound represented by Chemical Formula 1.

According to another embodiment, an image sensor includes the photoelectric device.

In some embodiments, image sensor may include a semiconductor substrate integrated with a plurality of first photo-sensing devices sensing light in a blue wavelength region and a plurality of second photo-sensing devices sensing light in a red wavelength region, and the photoelectric device on the semiconductor substrate and selectively sensing light in a green wavelength region.

The first photo-sensing device and the second photo-sensing device may be stacked in a vertical direction in the semiconductor substrate.

The image sensor may further include a color filter layer including a blue filter selectively transmitting light in a blue wavelength region and a red filter selectively transmitting light in a red wavelength region.

The image sensor may include a green photoelectric device which is the photoelectric device, a blue photoelectric device selectively absorbing light in a blue wavelength region, and a red photoelectric device selectively absorbing light in a red wavelength region that are stacked.

According to another embodiment, an electronic device includes the image sensor.

The compound may selectively absorb light in a green wavelength region and may have improved thermal stability and charge mobility. The compound improves efficiency of the device by increasing wavelength selectivity of the green wavelength region and provides photoelectric devices, image sensors and electronic devices that do not deteriorate performance even at high temperature processes due to improved thermal stability.

DETAILED DESCRIPTION

Figure 1:
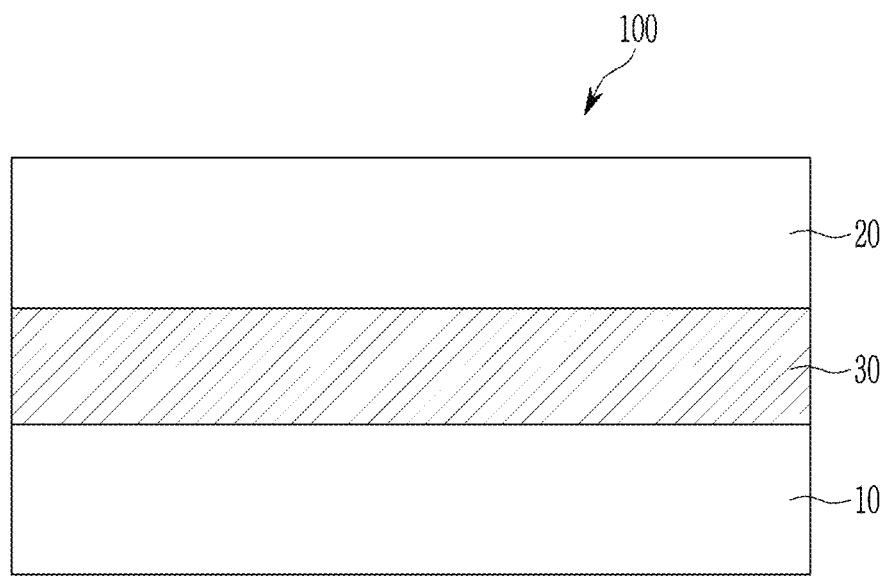
FIG. 1 is a cross-sectional view showing a photoelectric device according to an embodiment.

Example embodiments will hereinafter be described in detail, and may be easily performed by a person having an ordinary skill in the related art. However, this disclosure may be embodied in many different forms and is not to be construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

As used herein, "at least one of A, B, or C," "one of A, B, C, or a combination thereof" and "one of A, B, C, and a combination thereof" refer to each constituent element, and a combination thereof (e.g., A; B; A and B; A and C; B and C; or A, B, and C).

As used herein, when a specific definition is not otherwise provided, "substituted" refers to replacement of a hydrogen of a compound or a functional group by a substituent selected from a halogen atom (F, Br, Cl, or I), a hydroxy group, a nitro group, a cyano group, an azido group, an amidino group, an amine group (—NR'R", wherein R' and R" are the same or different, and are a hydrogen atom, a C1 to C20 alkyl group, or a C6 to C30 aryl group), a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C1 to C20 alkoxy group, a C2 to C20 alkenyl group, a C2 to C20 alkynyl group, a C6 to C30 aryl group, a C7 to C30 arylalkyl group, a C2 to C20 heteroaryl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof.

As used herein, when a specific definition is not otherwise provided, "arene group" may be a hydrocarbon ring group having an arene ring, in which all ring-forming atoms are carbon atoms and form a conjugation structure. The arene group may include monocyclic, non-fused polycyclic, or fused polycyclic (e.g., rings sharing adjacent pairs of carbon atoms) hydrocarbon ring groups, and an additional ring(s) of the non-fused polycyclic hydrocarbon ring group and the fused polycyclic hydrocarbon ring group may be an arene ring or a hydrocarbon ring which is not an arene ring. The arene group may be a C6 to C30 arene group, a C6 to C20 arene group, or a C6 to C10 arene group.

As used herein, when a specific definition is not otherwise provided, "heteroarene group" refers to a group obtained by replacing 1 to 3 carbon atom(s) in an arene ring of the arene group with hetero atom(s) selected from N, O, S, P and Si. The heteroarene group may be a C3 to C30 heteroarene group, a C3 to C20 heteroarene group, or a C3 to C10 heteroarene group.

As used herein, "aryl group" refers to a monovalent arene group, and "heteroaryl group" refers to a monovalent heteroarene group.

As used herein, when a specific definition is not otherwise provided, "hydrocarbon ring group" may be a C3 to C30 hydrocarbon ring group. The hydrocarbon ring group may be an arene ring group (e.g., a C6 to C30 arene group, a C6 to C20 arene group, or a C6 to C10 arene group, such as a C6 to C30 aryl group, a C6 to C20 aryl group, or a C6 to C10 aryl group), an alicyclic hydrocarbon ring group (e.g., a C3 to C30 cycloalkyl group, a C5 to C30 cycloalkyl group, a C3 to C20 cycloalkyl group, or a C3 to C10 cycloalkyl group), or a fused ring group thereof. For example, the fused ring group refers to a fused ring group of an arene ring and a alicyclic hydrocarbon ring, for example a fused ring formed by linking at least one arene ring such as a C6 to C30 arene group, a C6 to C20 arene group, or a C6 to C10 arene group, to at least one alicyclic hydrocarbon ring such as a C3 to C30 cycloalkyl group, a C3 to C20 cycloalkyl group, or a C3 to C10 cycloalkyl group.

As used herein, when a specific definition is not otherwise provided, "heterocyclic group" refers to a C2 to C30 heterocyclic group. The heterocyclic group refers to a hydrocarbon ring group in which at least one carbon, for example, one to three carbons are replaced by a heteroatom selected from N, O, S, P and Si, wherein the hydrocarbon ring group is selected from an arene hydrocarbon ring group (e.g., a C6 to C30 arene group, a C6 to C20 arene group, or a C6 to C10 arene group, such as a C6 to C30 aryl group, a C6 to C20 aryl group, or a C6 to C10 aryl group), an alicyclic hydrocarbon ring group (e.g., a C3 to C30 cycloalkyl group, a C3 to C20 cycloalkyl group, or a C3 to C10 cycloalkyl group), and a fused ring group thereof. In addition, one or more carbon atoms of the heterocyclic group may be replaced by a thiocarbonyl group (C=S).

As used herein, when a specific definition is not otherwise provided, "hetero" refers to one including 1 to 3 heteroatoms selected from N, O, S, Se, Te, P, and Si.

As used herein, "alkyl group" refers to a monovalent linear or branched saturated hydrocarbon group, for example a methyl group, an ethyl group, a propyl group, an isopropyl group, an n-butyl group, an isobutyl group, a t-butyl group, a pentyl group, a hexyl group, and the like.

As used herein, "cycloalkyl group" refers to a monovalent hydrocarbon cyclic group in which the atoms of the cycle are carbon, for example a cyclopropyl group, a cyclobutyl group, a cyclopentyl group, or a cyclohexyl group.

As used herein, when a definition is not otherwise provided, "cyano-containing group" refers to a monovalent group such as a C1 to C30 (e.g., C1 to C20, or C1 to C10) alkyl group, a C2 to C30 (e.g., C2 to C20, or C2 to C10) alkenyl group, or a C2 to C30 (e.g., C2 to C20, or C2 to C10) alkynyl group where at least one hydrogen is substituted with a cyano group. The cyano-containing group also refers to a divalent group such as $=CR^{x'}-(CR^xR^y)_p-CR^{y'}(CN)_2$ wherein $R^x$, $R^y$, $R^{x'}$, and $R^{y'}$ are independently hydrogen or a C1 to C10 alkyl group and p is an integer of 0 to 10 (or 1 to 10). Specific examples of the cyano-containing group may be a dicyanomethyl group, a dicyanovinyl group, a cyanoethynyl group, and the like. As used herein, the cyano-containing group does not include a functional group including a cyano group (—CN) alone.

As used herein, when a definition is not otherwise provided, "combination thereof" refers to at least two groups bound to each other by a single bond or a C1 to C10 alkylene group, or at least two fused groups.

As used herein, when a definition is not otherwise provided, "aromatic hydrocarbon group" includes a C6 to C30 arene group, such as a C6 to C30 aryl group or a C6 to C30 arylene group, such as a phenyl group or a naphthyl group, but is not limited thereto.

As used herein, when a definition is not otherwise provided, "aliphatic hydrocarbon group" may include, for example, a C1 to C15 alkyl group such as a methyl group, an ethyl group, a propyl group, and the like, a C1 to C15 alkylene group, a C2 to C15 alkenyl group such as an ethenyl group or a propenyl group, a C2 to C15 alkynyl group such as an ethynyl group or a propynyl group, but is not limited thereto.

As used herein, when a definition is not otherwise provided, "aromatic ring" refers to a C5 to C12 ring group (e.g., C6 to C10 aryl group) that provides a conjugated structure or a C2 to C10 heterocyclic group (e.g., C2 to C10 heteroaryl group) that provides a conjugated structure.

As used herein, when a definition is not otherwise provided, "spiro structure" may be a substituted or unsubstituted C5 to C30 hydrocarbon ring group or a substituted or unsubstituted C2 to C30 heterocyclic group which shares one atom (e.g., Si, Ge or C) with another ring. The C5 to C30 hydrocarbon ring group may be, for example, a substituted or unsubstituted C5 to C30 cycloalkyl group (e.g., a substituted or unsubstituted C3 to C20 cycloalkyl group or a substituted or unsubstituted C3 to C10 cycloalkyl group) and the substituted or unsubstituted C2 to C30 heterocyclic group may be, for example, a substituted or unsubstituted C2 to C20 heterocycloalkyl group or a substituted or unsubstituted C2 to C10 heterocycloalkyl group.

Hereinafter, a compound according to an embodiment is described. The compound is represented by Chemical Formula 1.

[Chemial Formula 1]

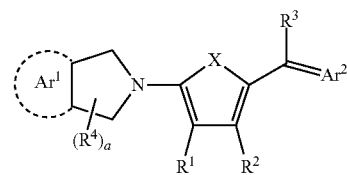

In Chemical Formula 1,

Ar¹ is a substituted or unsubstituted C6 to C30 arene group, a substituted or unsubstituted C3 to C30 heteroarene group, or a condensed ring thereof, X is O, S, Se, Te, S(=O), S(=O)$_2$, NR$^a$, SiR$^b$R$^c$, GeR$^d$R$^e$, or CR$^f$R$^g$ (wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure), Ar² is a substituted or unsubstituted C6 to C30 hydrocarbon ring group having at least one functional group selected from C=O, C=S, C=Se, and C=Te, a substituted or unsubstituted C2 to C30 heterocyclic group having at least one functional group selected from C=O, C=S, C=Se, and C=Te, or a fused ring group thereof, R¹ to R³ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, a pentafluorosulfanyl group (—SF$_5$), a hydroxyl group, an amine group, a hydrazine group, a hydrazone group, a carboxyl group or a salt thereof, a sulfonic acid group or a salt thereof, a phosphoric acid group or a salt thereof, —SiR$^a$R$^b$R$^c$ (wherein R$^a$, R$^b$, and R$^c$ are independently hydrogen or a substituted or unsubstituted C1 to C10 alkyl group), or a combination thereof, R⁴ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a is an integer of 0 to 4.

The compound represented by Chemical Formula 1 includes an electron donor moiety of an N-containing ring, a linker of an X-containing ring, and an electron acceptor moiety represented by Ar². In Chemical Formula 1, the electron donor moiety has a non-conjugation structure of an N-containing ring, thereby improving a light absorption property of a green light region and inducing a planar structure to improve charge mobility of the compound.

The compound represented by Chemical Formula 1 may have an aspect ratio (Z/X) obtained by dividing the shortest length (Z) by the longest length (X) in a range of less than or equal to about 0.30, for example less than or equal to about 0.25 or less than or equal to about 0.20. Within the range, the compound may maintain excellent planarity, and accordingly, the charge mobility thereof may be improved.

The compound represented by Chemical Formula 1 has a donor-linker-acceptor structure of a specific structure, whereby an absorption wavelength may be adjusted in a green wavelength range (about 500 nm to about 580 nm), a deposition temperature thereof may be lowered, and an absorption coefficient may be increased.

In Chemical Formula 1, Ar¹ may be a C6 to C30 arene group, a substituted or unsubstituted C3 to C30 heteroarene group, or a condensed ring thereof.

In example embodiments, the compound represented by Chemical Formula 1 may be represented by Chemical Formula 2-1.

[Chemial Formula 2-1]

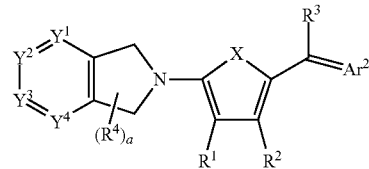

In Chemical Formula 2-1,

X is O, S, Se, Te, S(=O), S(=O)$_2$, NR$^a$, SiR$^b$R$^c$, GeR$^d$R$^e$, or CR$^f$R$^g$ (wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure), Ar² is a substituted or unsubstituted C6 to C30 hydrocarbon ring group having at least one functional group selected from C=O, C=S, C=Se, and C=Te, a substituted or unsubstituted C2 to C30 heterocyclic group having at least one functional group selected from C=O, C=S, C=Se, and C=Te, or a fused ring group thereof, R¹ to R³ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, a pentafluorosulfanyl group (—SF$_5$), a hydroxyl group, an amine group, a hydrazine group, a hydrazone group, a carboxyl group or a salt thereof, a sulfonic acid group or a salt thereof, a phosphoric acid group or a salt thereof, —SiR$^a$R$^b$R$^c$ (wherein R$^a$, R$^b$ and R$^c$ are independently hydrogen or a substituted or unsubstituted C1 to C10 alkyl group), or a combination thereof, R⁴ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a is an integer of 0 to 4, and Y¹ to Y⁴ are independently N or CR$^p$, wherein R$^p$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group or adjacent CR$^p$'s are linked to each other to form a substituted or unsubstituted C6 to C30 arene group, a substituted or unsubstituted C3 to C30 heteroarene group, or a condensed ring thereof.

In example embodiments, the compound represented by Chemical Formula 1 may be represented by Chemical Formula 2-2.

[Chemical Formula 2-2]

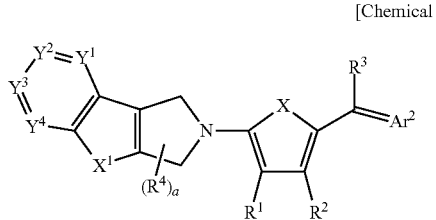

[Chemical Formula 2-3]

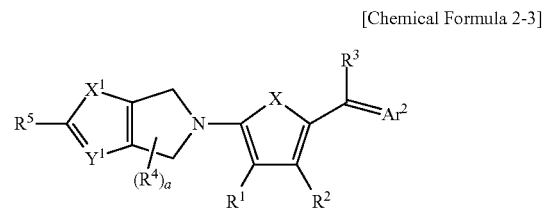

In Chemical Formula 2-2,

X is O, S, Se, Te, S(=O), S(=O)$_2$, NR$^a$, SiR$^b$R$^c$, GeR$^d$R$^e$, or CR$^f$R$^g$ (wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure), X$^1$ is O, S, Se, Te, S(=O), S(=O)$_2$, NR$^a$, SiR$^b$R$^c$, GeR$^d$R$^e$, or CR$^f$R$^g$ (wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure), Ar$^2$ is a substituted or unsubstituted C6 to C30 hydrocarbon ring group having at least one functional group selected from C=O, C=S, C=Se, and C=Te, a substituted or unsubstituted C2 to C30 heterocyclic group having at least one functional group selected from C=O, C=S, C=Se, and C=Te, or a fused ring group thereof, R$^1$ to R$^3$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, a pentafluorosulfanyl group (—SF$_5$), a hydroxyl group, an amine group, a hydrazine group, a hydrazone group, a carboxyl group or a salt thereof, a sulfonic acid group or a salt thereof, a phosphoric acid group or a salt thereof, —SiR$^a$R$^b$R$^c$ (wherein R$^a$, R$^b$ and R$^c$ are independently hydrogen or a substituted or unsubstituted C1 to C10 alkyl group), or a combination thereof, R$^4$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a is an integer of 0 to 4, and Y$^1$ to Y$^4$ are independently N or CR$^p$, wherein R$^p$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group or adjacent CR$^p$'s are linked to each other to form a substituted or unsubstituted C6 to C30 arene group, a substituted or unsubstituted C3 to C30 heteroarene group, or a condensed ring thereof.

In example embodiments, the compound represented by Chemical Formula 1 may be represented by Chemical Formula 2-3.

In Chemical Formula 2-3,

Y$^1$ is N or CR$^p$, wherein R$^p$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group or R$^p$ and R$^5$ are linked to each other to form a substituted or unsubstituted C6 to C30 arene group, a substituted or unsubstituted C3 to C30 heteroarene group, or a condensed ring thereof, X is O, S, Se, Te, S(=O), S(=O)$_2$, NR$^a$, SiR$^b$R$^c$, GeR$^d$R$^e$, or CR$^f$R$^g$ (wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure), X$^1$ is O, S, Se, Te, S(=O), S(=O)$_2$, NR$^a$, SiR$^b$R$^c$, GeR$^d$R$^e$, or CR$^f$R$^g$ (wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure), Ar$^2$ is a substituted or unsubstituted C6 to C30 hydrocarbon ring group having at least one functional group selected from C=O, C=S, C=Se, and C=Te, a substituted or unsubstituted C2 to C30 heterocyclic group having at least one functional group selected from C=O, C=S, C=Se, and C=Te, or a fused ring group thereof, R$^1$ to R$^3$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, a pentafluorosulfanyl group (—SF$_5$), a hydroxyl group, an amine group, a hydrazine group, a hydrazone group, a carboxyl group or a salt thereof, a sulfonic acid group or a salt thereof, a phosphoric acid group or a salt thereof, —SiR$^a$R$^b$R$^c$ (wherein R$^a$, R$^b$ and R$^c$ are independently hydrogen or a substituted or unsubstituted C1 to C10 alkyl group), or a combination thereof, R$^4$ and R$^5$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a is an integer of 0 to 4.

In example embodiments, the compound represented by Chemical Formula 2-1 may be represented by one of Chemical Formulas 2-1A to 2-1E.

[Chemical Formula 2-1A]

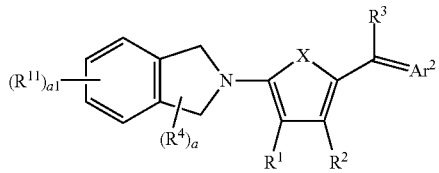

In Chemical Formula 2-1A,

X, Ar$^2$, R$^1$ to R$^4$, and a are the same as in Chemical Formula 2-1,

R$^{11}$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 is an integer of 0 to 4.

[Chemical Formula 2-1B]

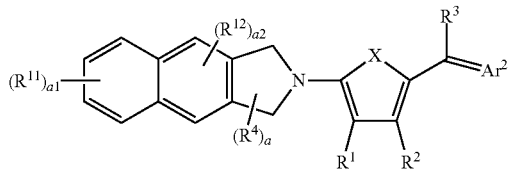

In Chemical Formula 2-1B,

X, Ar$^2$, R$^1$ to R$^4$, and a are the same as in Chemical Formula 2-1, R$^{11}$ and R$^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a1 is an integer of 0 to 4, and a2 is an integer of 0 to 2.

[Chemical Formula 2-1C]

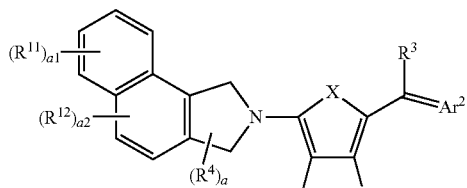

In Chemical Formula 2-1C,

X, Ar$^2$, R$^1$ to R$^4$, and a are the same as in Chemical Formula 2-1,

R$^{11}$ and R$^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a1 is an integer of 0 to 4, and a2 is an integer of 0 to 2.

[Chemical Formula 2-1D]

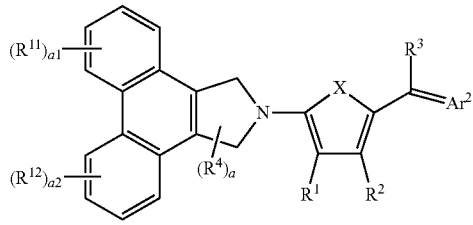

In Chemical Formula 2-1D,

X, Ar$^2$, R$^1$ to R$^4$, and a are the same as in Chemical Formula 2-1,

R$^{11}$ and R$^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer ranging from 0 to 4.

[Chemical Formula 2-1E]

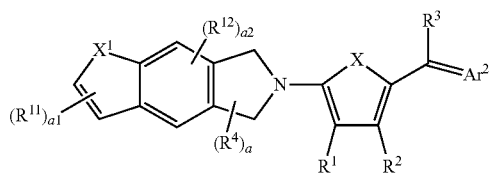

In Chemical Formula 2-1E,

X, Ar$^2$, R$^1$ to R$^4$, and a are the same as in Chemical Formula 2-1,

X$^1$ is O, S, Se, Te, S(=O), S(=O)$_2$, NR$^a$, SiR$^b$R$^c$, GeR$^d$R$^e$, or CR$^f$R$^g$ (wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure), R$^{11}$ and R$^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer of 0 to 2.

The compound represented by Chemical Formula 2-2 may be represented by one of Chemical Formulas 2-2A to 2-2J.

[Chemical Formula 2-2A]

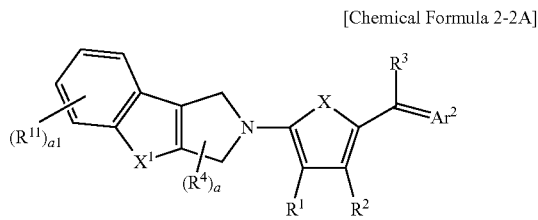

In Chemical Formula 2-2A,

X, $X^1$, $Ar^2$, $R^1$ to $R^4$, and a are the same as in Chemical Formula 2-2, $R^{11}$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 is an integer of 0 to 4.

[Chemical Formula 2-2B]

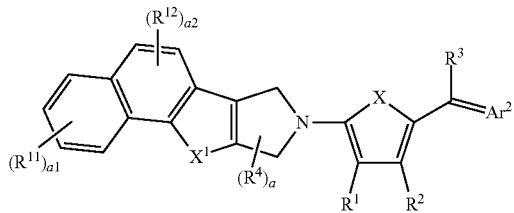

In Chemical Formula 2-2B,

X, $X^1$, $Ar^2$, $R^1$ to $R^4$, and a are the same as in Chemical Formula 2-2, $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a1 is an integer of 0 to 4, and a2 is an integer of 0 to 2.

[Chemical Formula 2-2C]

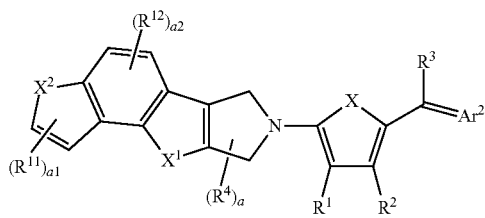

In Chemical Formula 2-2C,

X, $X^1$, $Ar^2$, $R^1$ to $R^4$, and a are the same as in Chemical Formula 2-2, $X^2$ is O, S, Se, Te, S(=O), S(=O)$_2$, $NR^a$, $SiR^bR^c$, $GeR^dR^e$, or $CR^fR^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer of 0 to 2.

[Chemical Formula 2-2D]

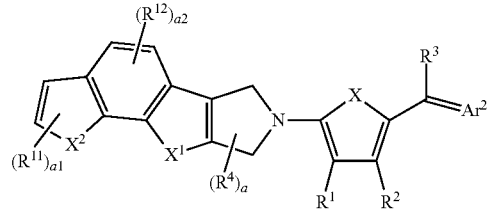

In Chemical Formula 2-2D,

X, $X^1$, $Ar^2$, $R^1$ to $R^4$, and a are the same as in Chemical Formula 2-2, $X^2$ is O, S, Se, Te, S(=O), S(=O)$_2$, $NR^a$, $SiR^bR^c$, $GeR^dR^e$, or $CR^fR^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer of 0 to 2.

[Chemical Formula 2-2E]

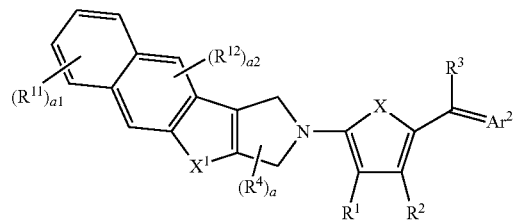

In Chemical Formula 2-2E,

X, $X^1$, $Ar^2$, $R^1$ to $R^4$, and a are the same as in Chemical Formula 2-2, $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a1 is an integer of 0 to 4, and a2 is an integer of 0 to 2.

[Chemical Formula 2-2F]

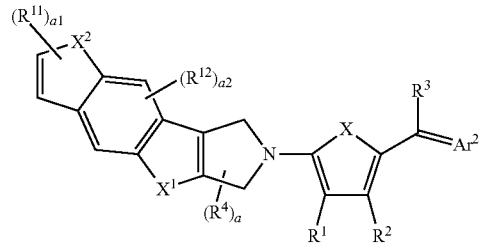

In Chemical Formula 2-2F,

X, $X^1$, $Ar^2$, $R^1$ to $R^4$, and a are the same as in Chemical Formula 2-2, $X^2$ is O, S, Se, Te, S(=O), S(=O)$_2$, $NR^a$, $SiR^bR^c$, $GeR^dR^e$, or $CR^fR^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer of 0 to 2.

[Chemical Formula 2-2G]

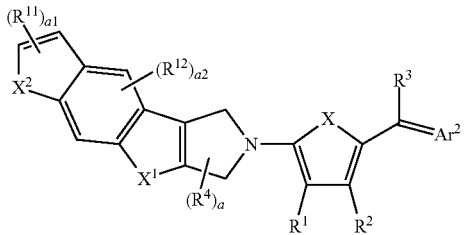

In Chemical Formula 2-2G,

X, $X^1$, $Ar^2$, $R^1$ to $R^4$, and a are the same as in Chemical Formula 2-2, $X^2$ is O, S, Se, Te, S(=O), S(=O)$_2$, $NR^a$, $SiR^bR^c$, $GeR^dR^e$, or $CR^fR^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer of 0 to 2.

[Chemical Formula 2-2H]

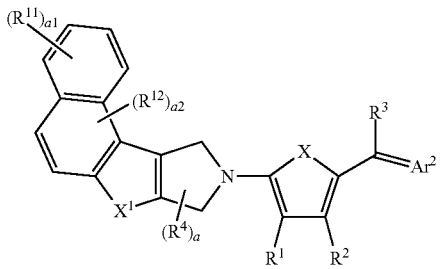

In Chemical Formula 2-2H,

X, $X^1$, $Ar^2$, $R^1$ to $R^4$, and a are the same as in Chemical Formula 2-2, $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a1 is an integer of 0 to 4, and a2 is an integer of 0 to 2.

[Chemical Formula 2-2I]

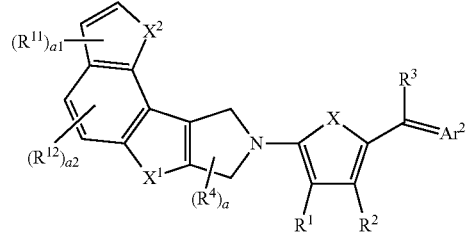

In Chemical Formula 2-2I,

X, $X^1$, $Ar^2$, $R^1$ to $R^4$, and a are the same as in Chemical Formula 2-2, $X^2$ is O, S, Se, Te, S(=O), S(=O)$_2$, $NR^a$, $SiR^bR^c$, $GeR^dR^e$, or $CR^fR^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer of 0 to 2.

[Chemical Formula 2-2J]

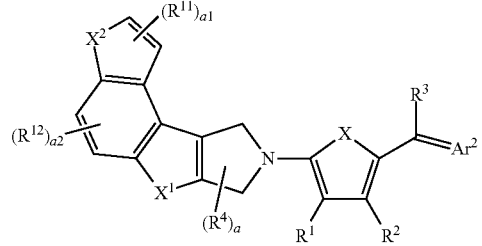

In Chemical Formula 2-2J,

X, $X^1$, $Ar^2$, $R^1$ to $R^4$, and a are the same as in Chemical Formula 2-2, $X^2$ is O, S, Se, Te, S(=O), S(=O)$_2$, $NR^a$, $SiR^bR^c$, $GeR^dR^e$, or $CR^fR^g$ (wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure), $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer of 0 to 2.

The compound represented by Chemical Formula 2-3 may be represented by one of Chemical Formulas 2-3A to 2-3D.

[Chemical Formula 2-3A]

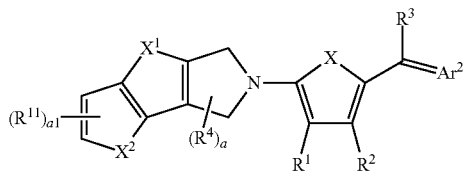

In Chemical Formula 2-3A,

X, $X^1$, $Ar^2$, $R^1$ to $R^4$, and a are the same as in Chemical Formula 2-3, $X^2$ is O, S, Se, Te, S(=O), S(=O)$_2$, NR$^a$, SiR$^b$R$^c$, GeR$^d$R$^e$, or CR$^f$R$^g$ (wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure), $R^{11}$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 is an integer of 0 to 2.

[Chemical Formula 2-3B]

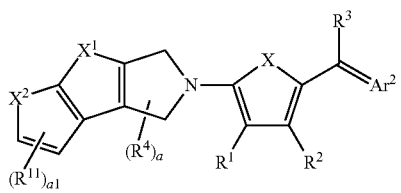

In Chemical Formula 2-3B,

X, $X^1$, $Ar^2$, $R^1$ to $R^4$, and a are the same as in Chemical Formula 2-3, $X^2$ is O, S, Se, Te, S(=O), S(=O)$_2$, NR$^a$, SiR$^b$R$^c$, GeR$^d$R$^e$, or CR$^f$R$^g$ (wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure), $R^{11}$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 is an integer of 0 to 2.

[Chemical Formula 2-3C]

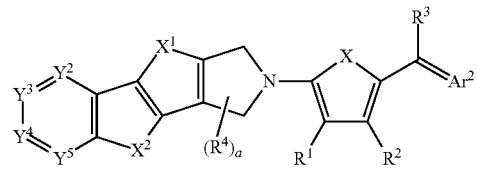

In Chemical Formula 2-3C,

X, $X^1$, $Ar^2$, $R^1$ to $R^4$, and a are the same as in Chemical Formula 2-3, $X^2$ is O, S, Se, Te, S(=O), S(=O)$_2$, NR$^a$, SiR$^b$R$^c$, GeR$^d$R$^e$, or CR$^f$R$^g$ (wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure), and $Y^2$ to $Y^5$ are independently N or CR$^p$, wherein R$^p$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group or adjacent CR$^p$'s are linked to each other to form a substituted or unsubstituted C6 to C30 arene group, a substituted or unsubstituted C3 to C30 heteroarene group, or a condensed ring thereof.

[Chemical Formula 2-3D]

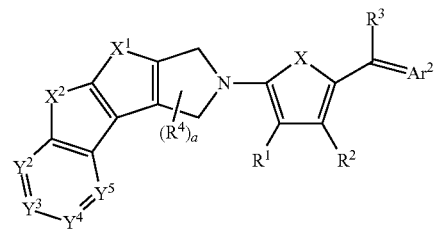

In Chemical Formula 2-3D,

X, $X^1$, $Ar^2$, $R^1$ to $R^4$, and a are the same as in Chemical Formula 2-3, $X^2$ is O, S, Se, Te, S(=O), S(=O)$_2$, NR$^a$, SiR$^b$R$^c$, GeR$^d$R$^e$, or CR$^f$R$^g$ (wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure), and $Y^2$ to $Y^5$ are independently N or CR$^p$, wherein R$^p$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group or adjacent CR$^p$'s are linked to each other to form a substituted or unsubstituted C6 to C30 arene group, a substituted or unsubstituted C3 to C30 heteroarene group, or a condensed ring thereof.

In Chemical Formula 1, Chemical Formulas 2-1 to 2-3, Chemical Formulas 2-1A to 2-1E, Chemical Formulas 2-2A to 2-2J, and Chemical Formulas 2-3A to 2-3D, when X is SiR$^b$R$^c$, GeR$^d$R$^e$, or CR$^f$R$^g$, R$^b$ and R$^c$, R$^d$ and R$^e$, or R$^f$ and R$^g$ may be independently present or may be linked to each other to form a spiro structure. In addition, in Chemical Formula 2-2, Chemical Formula 2-3, Chemical Formula 2-1E, Chemical Formulas 2-2A to 2-2J, and Chemical Formula 2-3A to 2-3D, when X$^1$ is SiR$^b$R$^c$, GeR$^d$R$^e$, or CR$^f$R$^g$, R$^b$ and R$^c$, R$^d$ and R$^e$, or R$^f$ and R$^g$ may be independently present or may be linked to each other to form a spiro structure. In Chemical Formula 2-2C, Chemical Formula 2-2D, Chemical Formula 2-2E, Chemical Formula 2-2F, Chemical Formula 2-2G, Chemical Formula 2-2I, Chemical Formula 2-2J, Chemical Formula 2-3A, Chemical Formula 2-3B, Chemical Formula 2-3C, and Chemical Formula 2-3D, when X$^2$ is SiR$^b$R$^c$, GeR$^d$R$^e$, or CR$^f$R$^g$, R$^b$ and R$^c$, R$^d$ and R$^e$, or R$^f$ and R$^g$ may be independently present or may be linked to each other to form a spiro structure. The spiro structure may be a substituted or unsubstituted C5 to C30 hydrocarbon ring group or a substituted or unsubstituted C2 to C30 heterocyclic group. The C5 to C30 hydrocarbon ring group may be, for example, a substituted or unsubstituted C5 to C30 cycloalkyl group (e.g., a substituted or unsubstituted C3 to C20 cycloalkyl group or a substituted or unsubstituted C3 to C10 cycloalkyl group) and the substituted or unsubstituted C2 to C30 heterocyclic group may be, for example, a substituted or unsubstituted C2 to C20 heterocycloalkyl group or a substituted or unsubstituted C2 to C10 heterocycloalkyl group.

For example, when the spiro structure is a C5 cycloalkyl group or a C6 cycloalkyl group, the compound represented by Chemical Formula 1 may be represented by Chemical Formula 1A or 1B.

[Chemical Formula 1A]

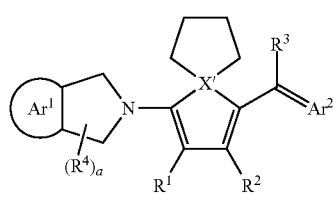

[Chemical Formula 1B]

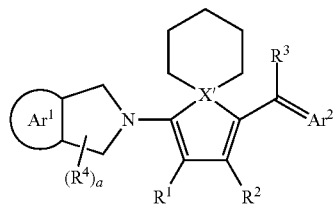

In Chemical Formulas 1A and 1B,
Ar$^1$, Ar$^2$, R$^1$ to R$^4$, and a are the same as in Chemical Formula 1 and X' is Si, Ge, or C.

In Chemical Formula 1, Ar$^2$ may be represented by Chemical Formula 3.

[Chemical Formula 3]

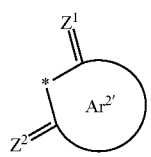

In Chemical Formula 3,
Ar$^{2'}$ is a substituted or unsubstituted C6 to C30 aryl group or a substituted or unsubstituted C3 to C30 heteroaryl group,
Z$^1$ is O, S, Se, or Te, and
Z$^2$ is O, S, Se, Te, or CR$^a$R$^b$, wherein R$^a$ and R$^b$ are independently hydrogen, a substituted or unsubstituted C1 to C10 alkyl group, a cyano group, or a cyano-containing group, and wherein when Z$^2$ is CR$^a$R$^b$, at least one of R$^a$ and R$^b$ is a cyano group or a cyano-containing group.

In Chemical Formula 1, Ar$^2$ may be a ring group represented by one of Chemical Formulas 4A to 4F.

[Chemical Formula 4A]

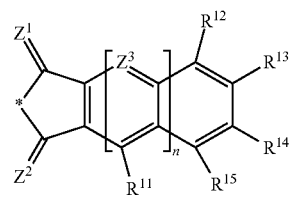

In Chemical Formula 4A,
Z$^1$ is O, S, Se, or Te,
Z$^2$ is O, S, Se, Te, or CR$^a$R$^b$, wherein R$^a$ and R$^b$ are independently hydrogen, a substituted or unsubstituted C1 to C10 alkyl group, a cyano group, or a cyano-containing group, and wherein when Z$^2$ is CR$^a$R$^b$, at least one of R$^a$ and R$^b$ is a cyano group or a cyano-containing group,
Z$^3$ is N or CR$^c$ (wherein R$^c$ is hydrogen, deuterium, or a substituted or unsubstituted C1 to C10 alkyl group),
R$^{11}$, R$^{12}$, R$^{13}$, R$^{14}$, and R$^{15}$ are the same or different and are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, wherein R$^{12}$ and R$^{13}$ and R$^{14}$ and R$^{15}$ are independently present or are linked to each other to form a fused aromatic ring,
n is 0 or 1, and
* is a linking portion.

[Chemical Formula 4B]

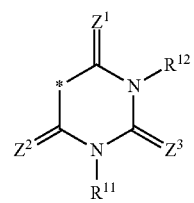

In Chemical Formula 4B,
Z$^1$ is O, S, Se, or Te,
Z$^2$ is O, S, Se, Te, or CR$^a$R$^b$, wherein R$^a$ and R$^b$ are independently hydrogen, a substituted or unsubstituted C1 to C10 alkyl group, a cyano group, or a cyano-containing group, and wherein when Z$^2$ is CR$^a$R$^b$, at least one of R$^a$ and R$^b$ is a cyano group or a cyano-containing group,
Z$^3$ is O, S, Se, Te, or C(R$^a$)(CN) (wherein R$^a$ is hydrogen, a cyano group (—CN), or a C1 to C10 alkyl group), R¹¹ and R¹² are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking portion.

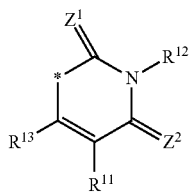

[Chemical Formula 4C]

In Chemical Formula 4C, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* is a linking portion.

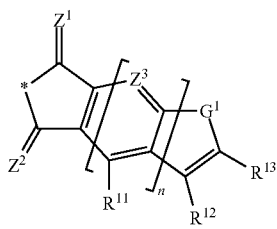

[Chemical Formula 4D]

In Chemical Formula 4D, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group, $Z^3$ is N or $CR^c$ (wherein $R^c$ is hydrogen or a substituted or unsubstituted C1 to C10 alkyl group), $G^1$ is O, S, Se, Te, $SiR^xR^y$, or $GeR^zR^w$, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, wherein $R^{12}$ and $R^{13}$ are independently present or are linked to each other to form an aromatic ring, n is 0 or 1, and

* is a linking portion.

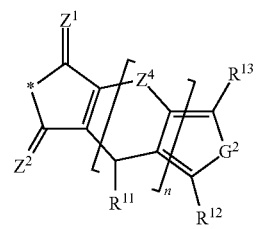

[Chemical Formula 4E]

In Chemical Formula 4E, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group, $Z^4$ is $NR^a$, $CR^bR^c$, O, S, Se, Te, S(=O), S(=O)$_2$, $SiR^dR^e$, or $GeR^fR^g$ (wherein $R^a$, $R^b$, $R^c$, $R^d$, $R^e$, $R^d$, $R^e$, $R^f$, and $R^g$ are independently hydrogen or a substituted or unsubstituted C1 to C10 alkyl group), $G^2$ is O, S, Se, Te, $SiR^xR^y$, or $GeR^zR^w$, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group, $R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, n is 0 or 1, and

* is a linking portion.

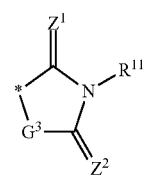

[Chemical Formula 4F]

$Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group, $R^{11}$ is hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^3$ is O, S, Se, Te, $SiR^xR^y$, or $GeR^zR^w$, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group.

The ring group represented by Chemical Formula 4A may be a ring group represented by Chemical Formula 4A-1 or 4A-2.

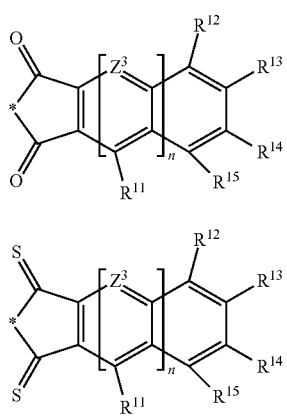

[Chemical Formula 4A-1]

[Chemical Formula 4A-2]

In Chemical Formulas 4A-1 and 4A-2, $Z^3$, $R^{11}$, n, $R^{12}$, $R^{13}$, $R^{14}$, and $R^{15}$ are the same as in Chemical Formula 4A.

The ring group represented by Chemical Formula 4A may be a ring group represented by Chemical Formula 4A-3 when $R^{12}$ and $R^{13}$ and/or $R^{14}$ and $R^{15}$ are independently linked to each other to form a fused aromatic ring.

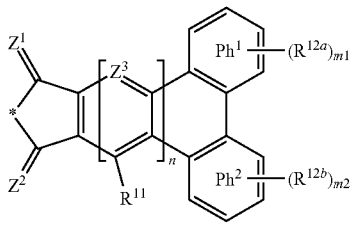

[Chemical Formula 4A-3]

In Chemical Formula 4A-3, $Z^1$, $Z^2$, $Z^3$, $R^{11}$, and n are the same as in Chemical Formula 4A, $R^{12a}$ and $R^{12b}$ are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, m1 and m2 are independently an integer of 0 to 4, $Ph^1$ and $Ph^2$ mean a fused phenylene ring and one of $Ph^1$ and $Ph^2$ may be optionally omitted.

The ring group represented by Chemical Formula 4B may be, for example, a ring group represented by Chemical Formula 4B-1, 4B-2, or 4B-3.

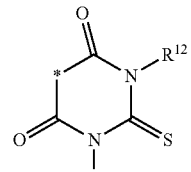

[Chemical Formula 4B-1]

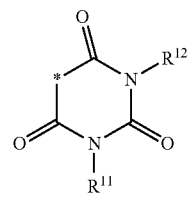

[Chemical Formula 4B-2]

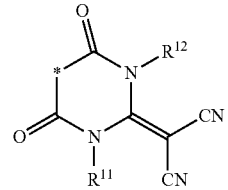

[Chemical Formula 4B-3]

In Chemical Formulas 4B-1, 4B-2, and 4B-3, $R^{11}$ and $R^{12}$ are the same as in Chemical Formula 4B.

The ring group represented by Chemical Formula 4C may be, for example, a ring group represented by Chemical Formula 4C-1 or 4C-2.

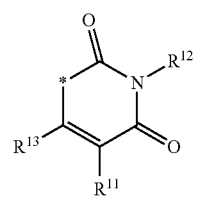

[Chemical Formula 4C-1]

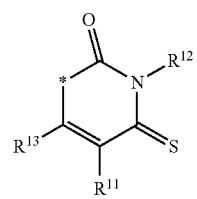

[Chemical Formula 4C-2]

In Chemical Formulas 4C-1 and 4C-2, $R^{11}$ to $R^{13}$ are the same as in Chemical Formula 4C.

In Chemical Formula 1, N of the electron donor moiety, X of the X-containing ring, and $Z^1$ (O, S, Se, or Te) present in the electron acceptor moiety increase intra-molecular interactions at specific wavelengths and thus absorption intensity may be improved.

Specific examples of the compound represented by Chemical Formula 1 may include compounds of Chemical Formula 5A, Chemical Formula 5B, or Chemical Formula 5C, but are not limited thereto.

[Chemical Formula 5A]
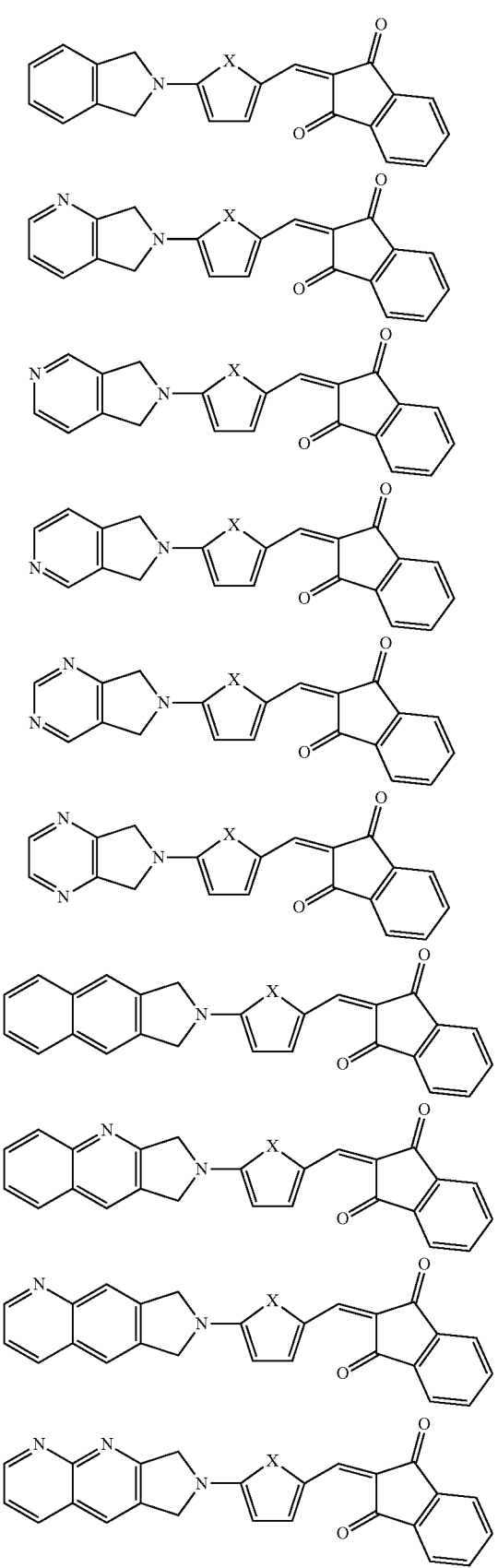
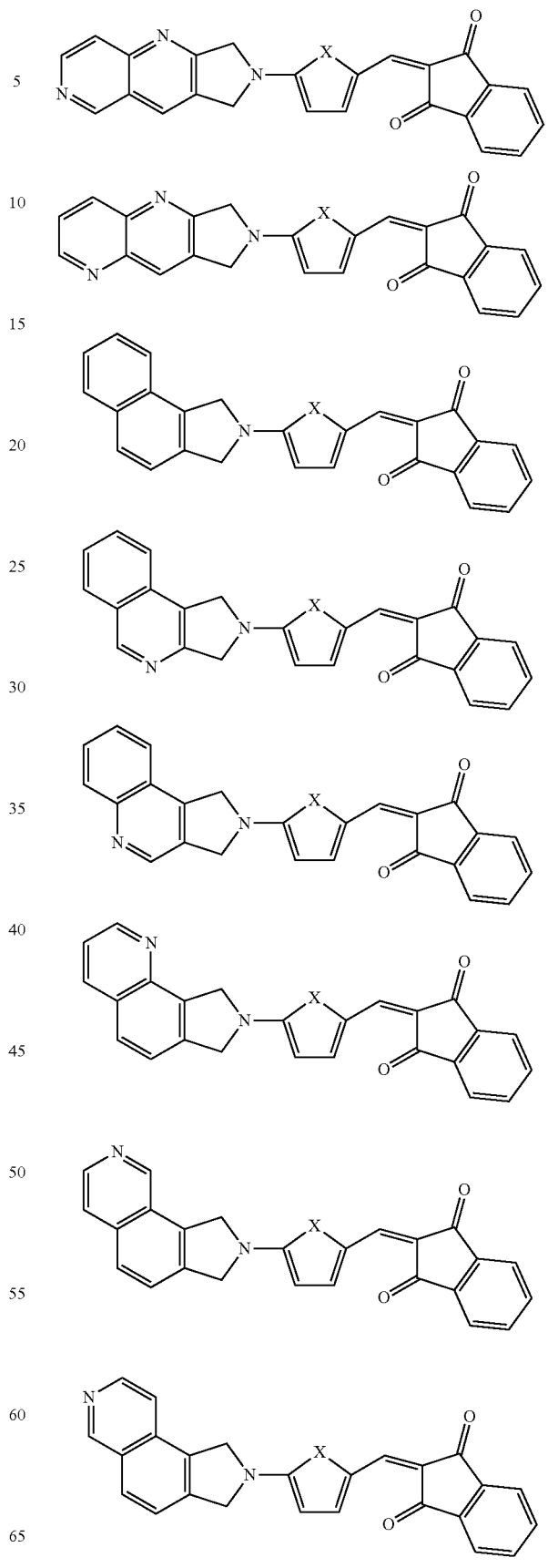

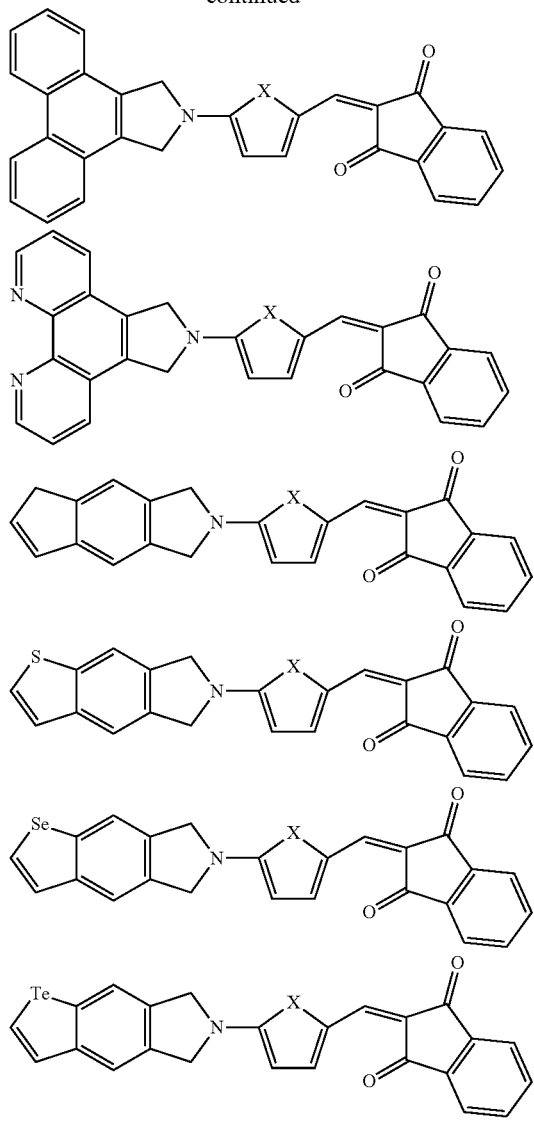

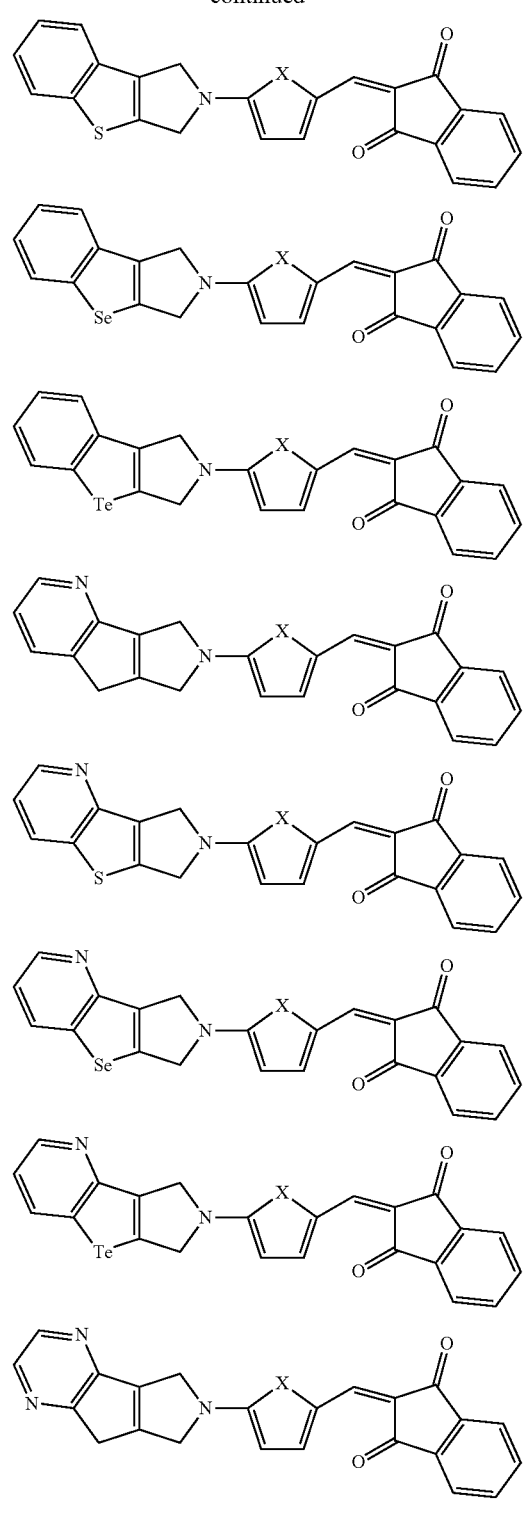

In Chemical Formula 5A,

X is the same as in Chemical Formula 1, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—ON), a cyano-containing group, and a combination thereof.

[Chemical Formula 5B]

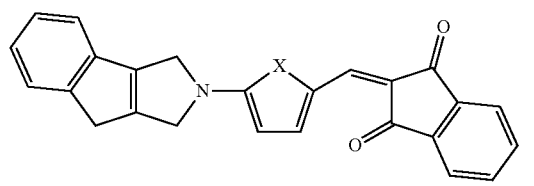

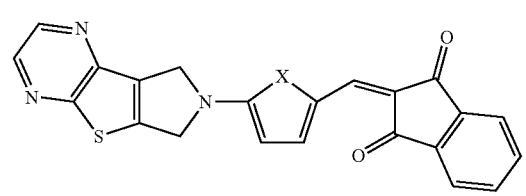

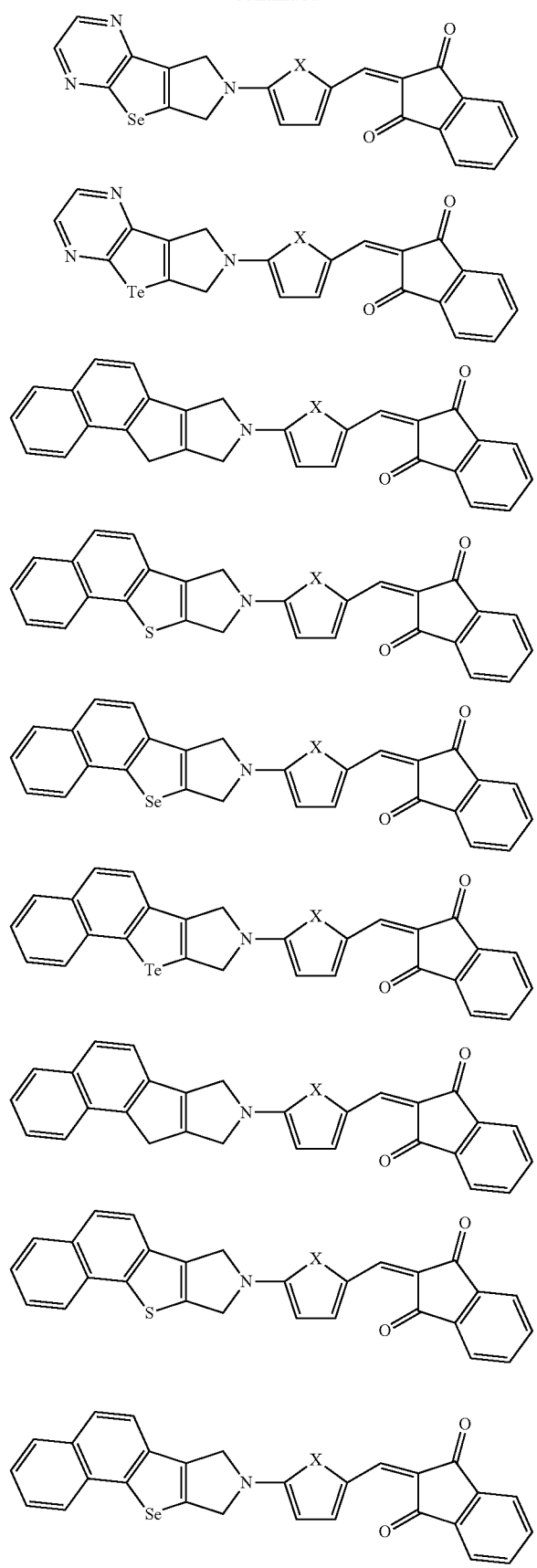
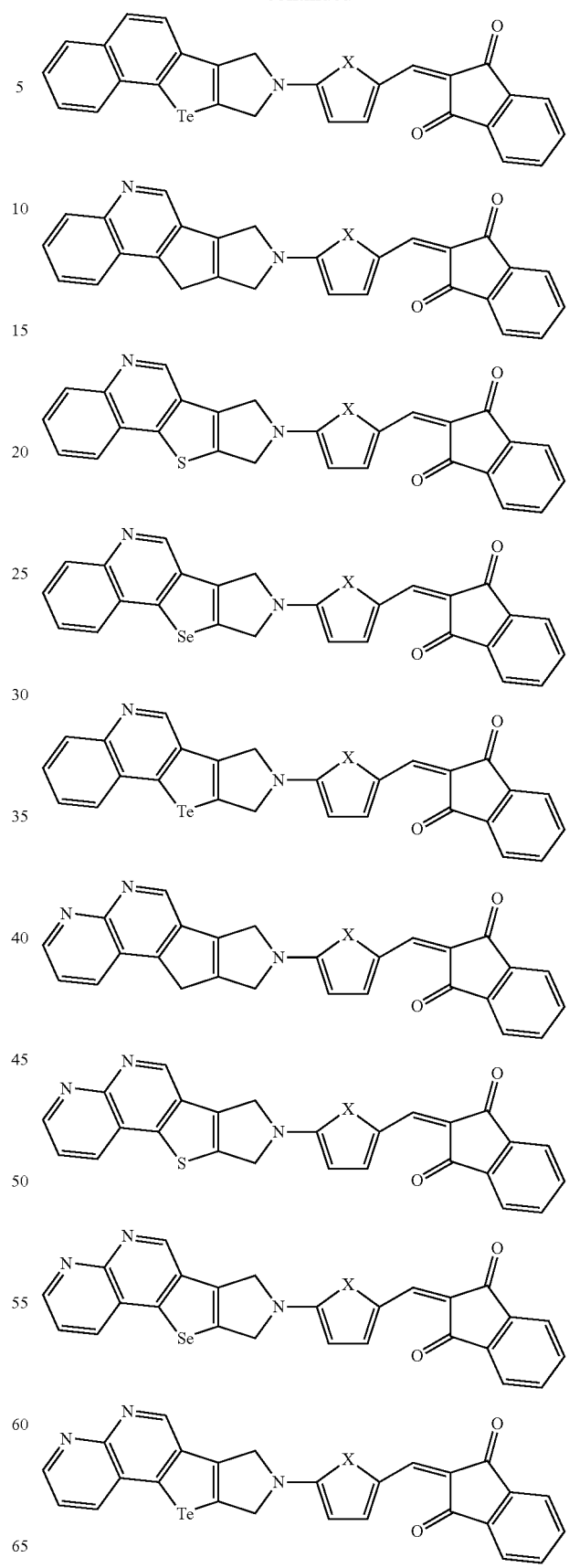

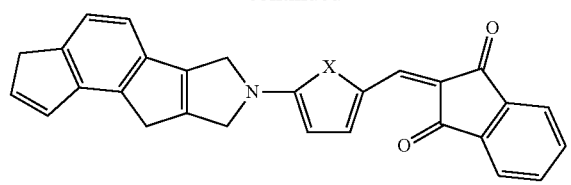
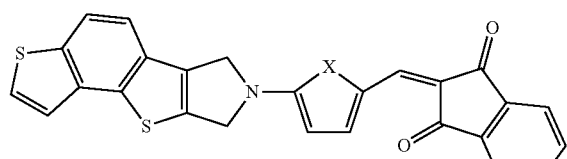
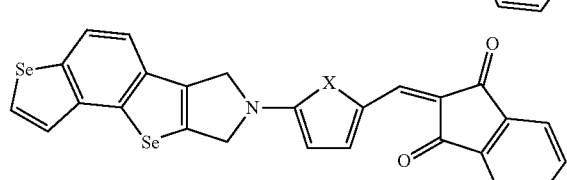
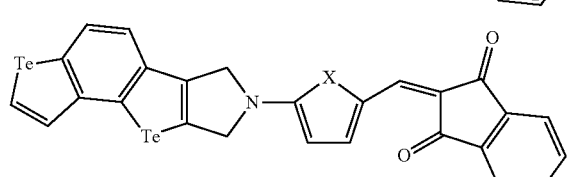
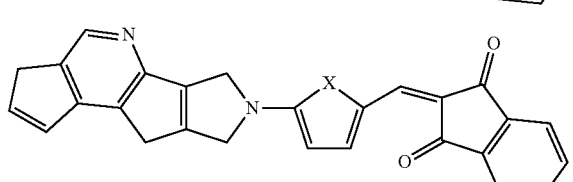
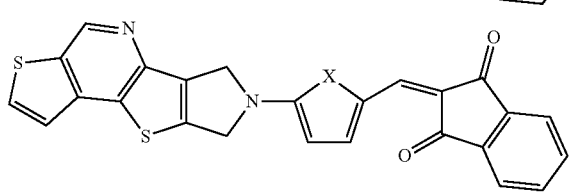
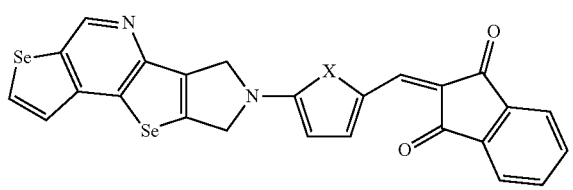
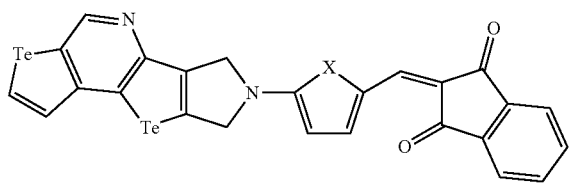
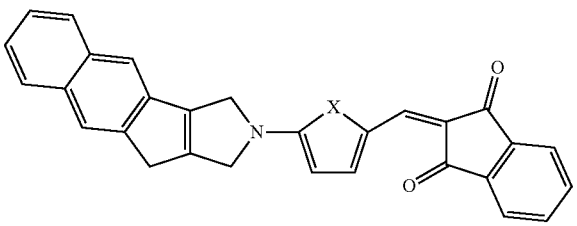
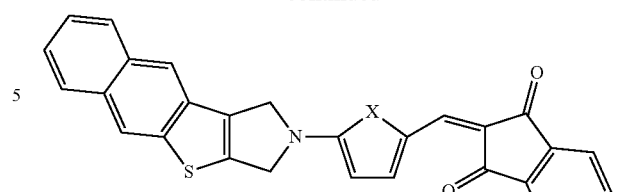
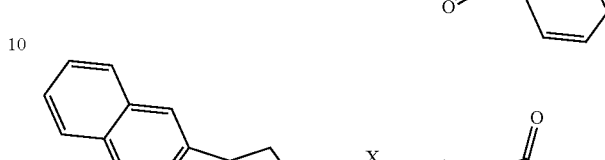
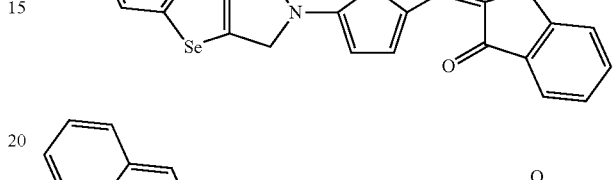
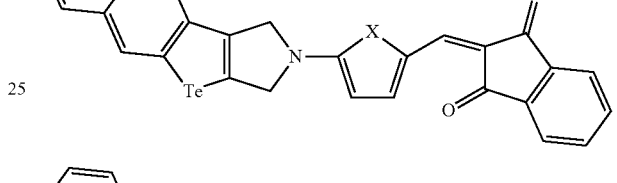
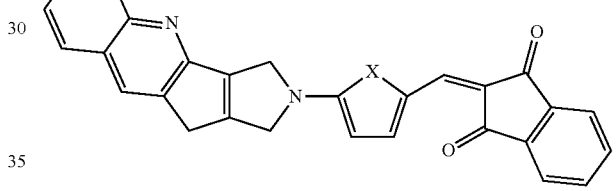
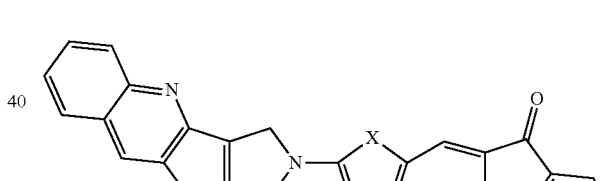
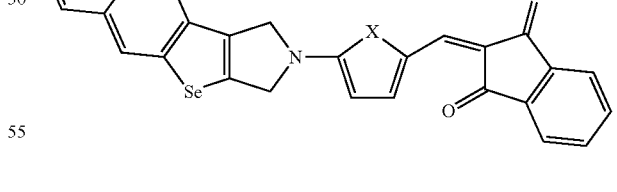
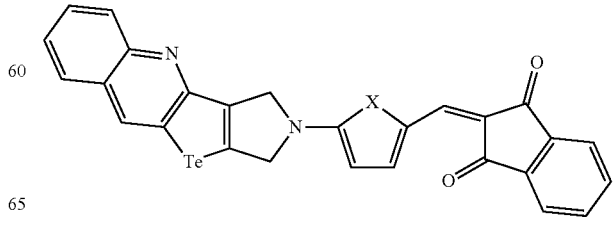

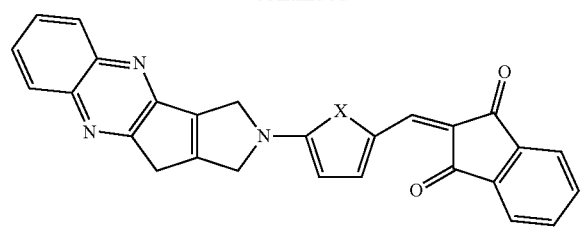
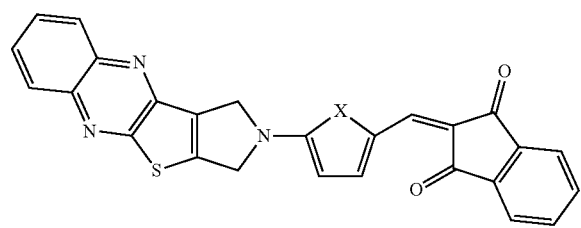
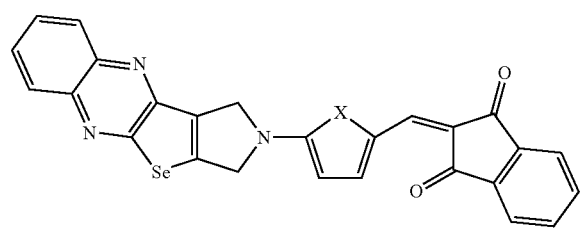
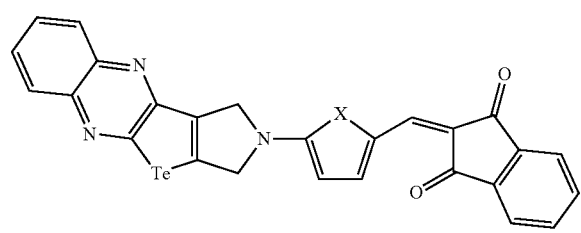
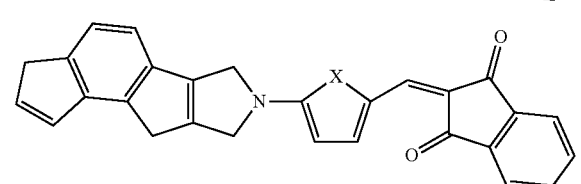
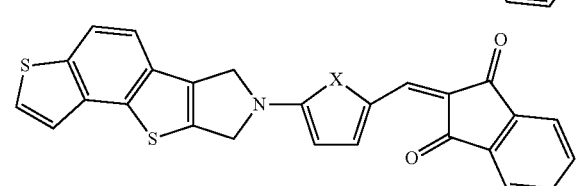
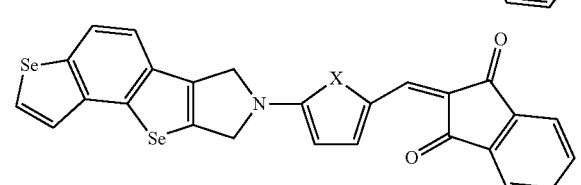
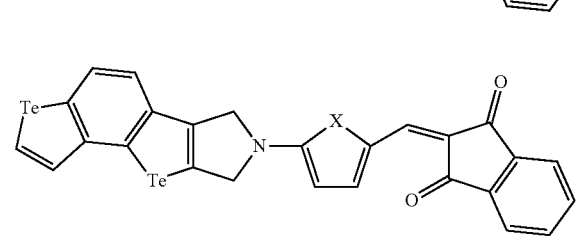
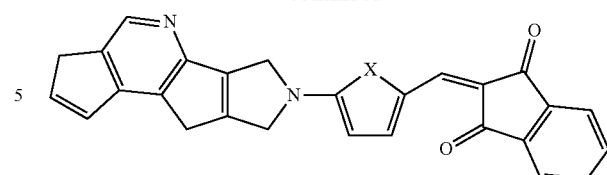
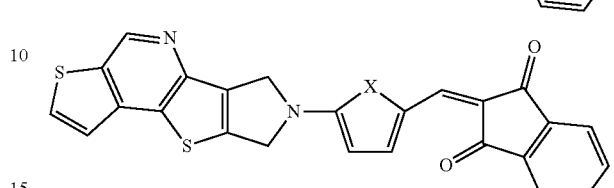
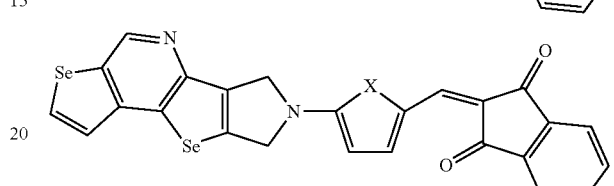
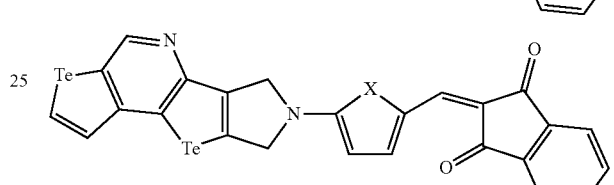
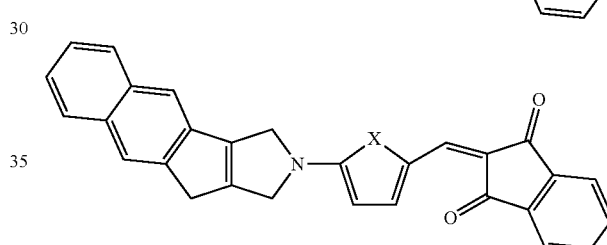
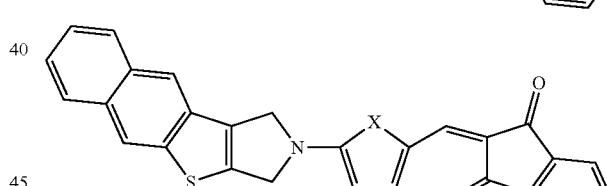
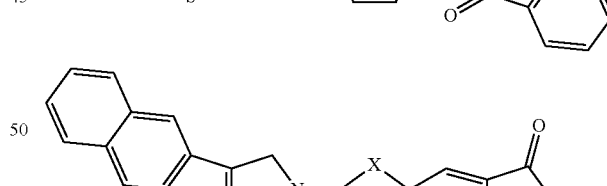
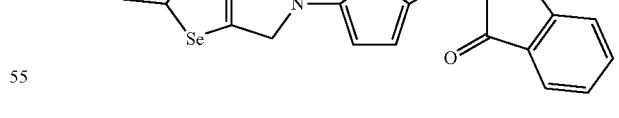
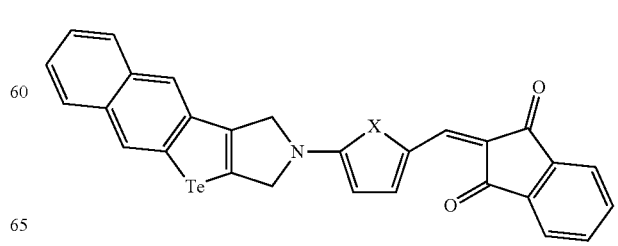

51
-continued
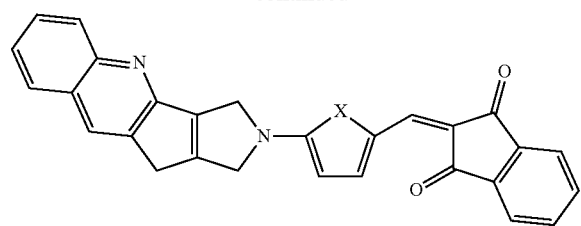
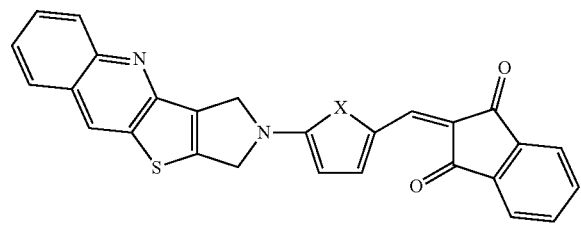
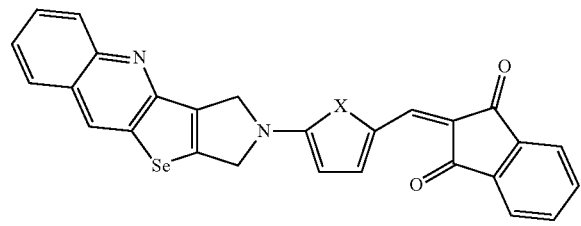
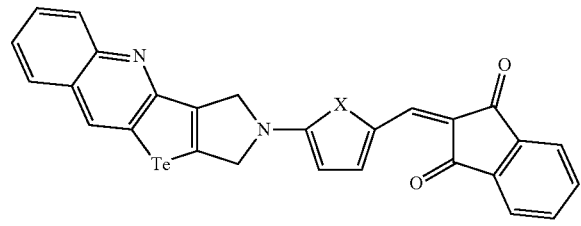
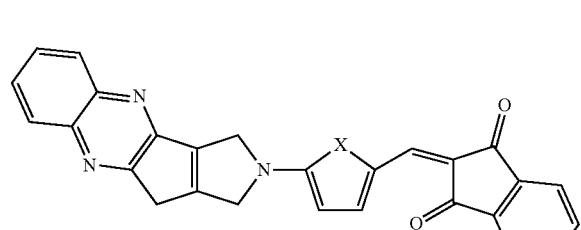
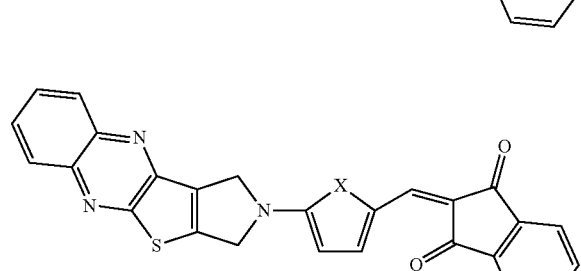
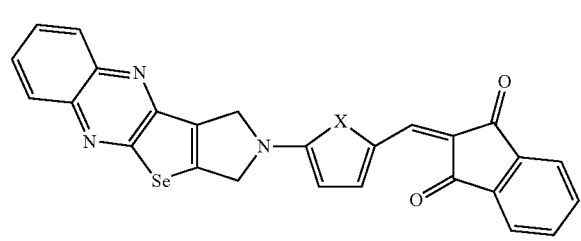
52
-continued
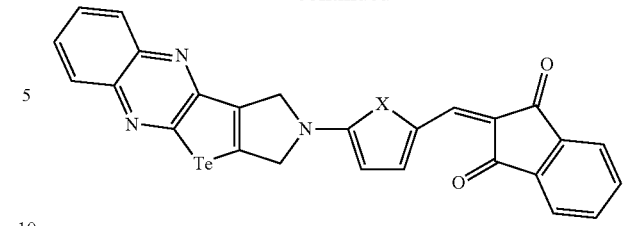
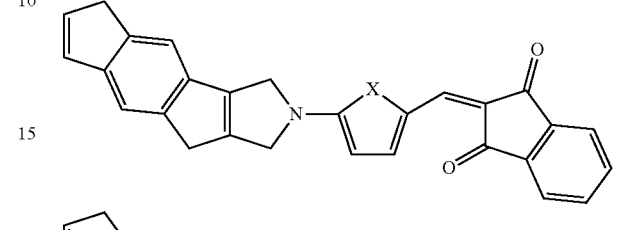
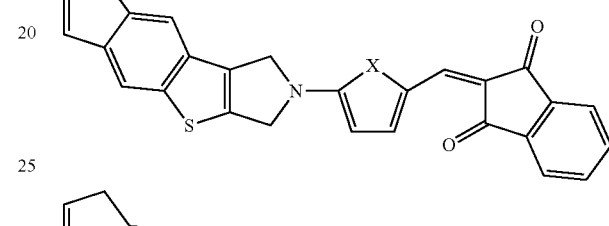
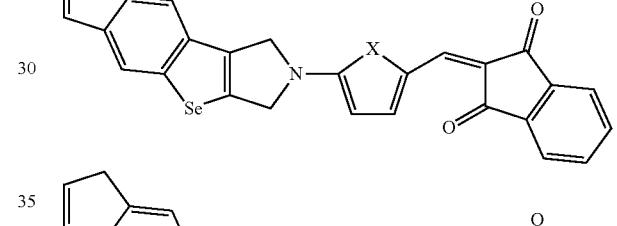
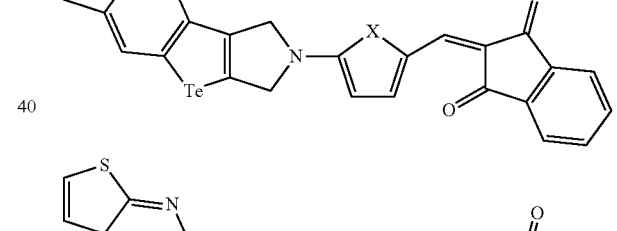
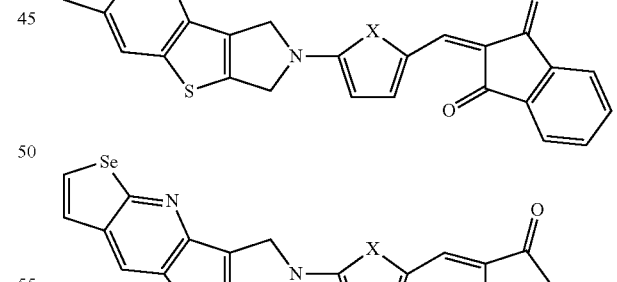
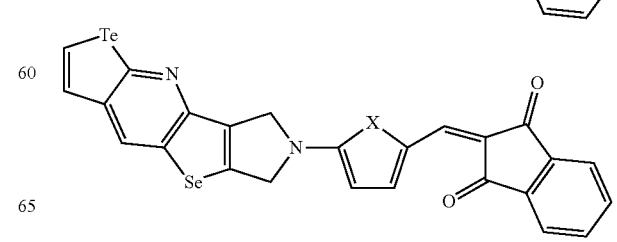

In Chemical Formula 5B,

X is the same as in Chemical Formula 1, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—ON), a cyano-containing group, and a combination thereof.

[Chemical Formula 5C]

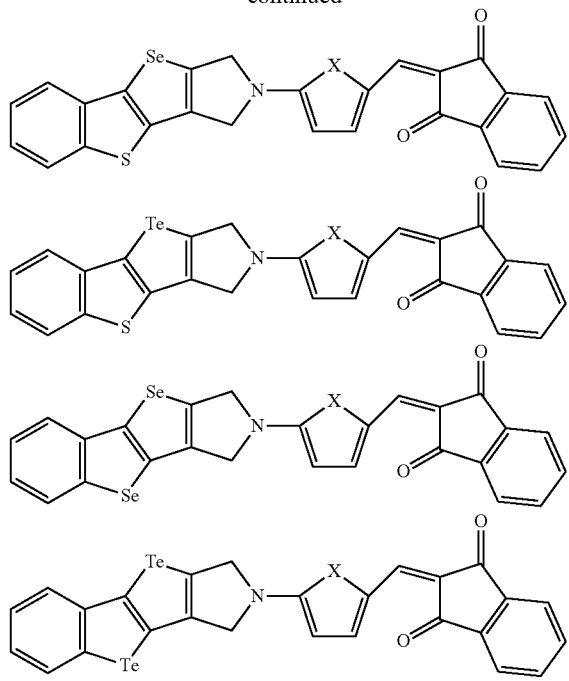

In Chemical Formula 5C,

X is the same as in Chemical Formula 1, and hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

In Chemical Formulas 5A, 5B, and 5C, a ring group alone represented by Chemical Formula 4A is illustrated as an acceptor structure, but the case of any one of Chemical Formulas 4B to 4F may be illustrated in the same manner.

The compound may selectively absorb light in a green wavelength region, and may have a maximum absorption wavelength ($\lambda_{max}$) in a wavelength region of greater than or equal to about 500 nm, for example greater than or equal to about 510 nm, greater than or equal to about 520 nm, greater than or equal to about 525 nm, or greater than or equal to about 530 nm and less than or equal to about 590 nm, for example less than or equal to about 580 nm, less than or equal to about 570 nm, less than or equal to about 560 nm, less than or equal to about 555 nm, or less than or equal to about 550 nm.

The compound may exhibit a light absorption curve having a full width at half maximum (FWHM) of about 50 nm to about 100 nm, for example about 50 nm to about 95 nm, about 60 nm to about 95 nm, about 70 nm to about 95 nm, or about 80 nm to about 95 nm in a thin film state. Herein, the FWHM is a width of a wavelength corresponding to half of a maximum absorption point. As used herein, when specific definition is not otherwise provided, it may be defined by absorbance measured by UV-Vis spectroscopy. When the full width at half maximum (FWHM) is within the range, selectivity in a green wavelength region may be increased. The thin film may be a thin film deposited under a vacuum condition.

The compound may be formed into a thin film by a deposition method. The deposition method may provide a uniform thin film and have small inclusion possibility of impurities into the thin film, but when the compound has a lower melting point than a temperature for the deposition, a product decomposed from the compound may be deposited and thus performance of a device may be deteriorated. Accordingly, the compound desirably has a higher melting point than the deposition temperature. In this regard, the compound has a melting point higher than the deposition temperature, for example, by about 10° C. or higher, about 15° C. or higher, about 20° C. or higher, about 25° C. or higher, or about 30° C. or higher, and thus may be desirably used in the deposition process.

In more detail, the donor-acceptor-type material represented by the structure of Chemical Formula 1 may be thermally decomposed at the melting point ($T_m$) of the material because the melting point ($T_m$) is similar to the decomposition temperature (Td). If the temperature (sublimation temperature, deposition temperature, $T_s$) at which a film is formed by vacuum deposition is higher than $T_m$, decomposition occurs more preferentially than sublimation (deposition), and thus a normal device cannot be manufactured. Since such a material cannot be used to produce a stable image sensor, $T_m$ should be higher than $T_s$, and $T_m$-$T_s \geq 10°$ C. is more desirable.

In addition, a micro lens array (MLA) needs to be formed to concentrate light after manufacturing an organic photoelectric device during manufacture of an image sensor. This micro lens array requires a relatively high temperature (greater than or equal to about 160° C., for example greater than or equal to about 170° C., greater than or equal to about 180° C., or greater than or equal to about 190° C.). The performance of the photoelectric devices (e.g., organic photoelectric devices) is required not to be deteriorated in these heat-treatment processes. The performance deterioration of the organic photoelectric device during the heat treatment of MLA may be caused not by chemical decomposition of an organic material but its morphology change. The morphology change is in general caused, when a material starts a thermal vibration due to a heat treatment. A material having a rigid molecular structure may not undergo the thermal vibration and may be prevented from the deterioration by the heat treatment. The compound may be suppressed from the thermal vibration of molecules due to a conjugation structure in the donor moiety and thus may be stably maintained during the MLA heat treatment and secure process stability.

The compound may be a p-type semiconductor compound.

Since the compound works as a p-type semiconductor, the compound may be appropriately used, as long as it has a higher LUMO energy level than an n-type semiconductor. For example, when the compound is mixed with an n-type material such as fullerene, the compound desirably has a higher LUMO energy level than the fullerene having a LUMO energy level of 4.2 eV. As for the appropriate HOMO-LUMO energy level of the compound, when the compound has a HOMO energy level ranging from about 5.2 eV to about 5.8 eV and an energy bandgap ranging from about 2.12 eV to about 2.48 eV, the LUMO energy level of the compound is in a range of about 3.7 eV to about 2.7 eV. The HOMO energy level may be evaluated by irradiating thin films with UV light and then, measuring an amount of photoelectrons emitted therefrom depending on energy with AC-3 (Riken Keiki Co., Ltd.), and the LUMO energy levels may be evaluated by obtaining an energy bandgap with a UV-Vis spectrometer (Shimadzu Corporation) and then, calculating using the energy bandgap and the measured HOMO energy level. The compound having a HOMO energy level, an LUMO energy level, and an energy bandgap within the ranges may be used as a p-type semiconductor compound effectively absorbing light in a green wavelength region, and thus has high external quantum efficiency (EQE) and resultantly improves photoelectric conversion efficiency.

In example embodiments, in view of a thin film formation, a stably depositable compound is desirable and thus the compound has a molecular weight of about 300 g/mol to about 1500 g/mol. However, even though the compound has a molecular weight out of the range, the compound may be used as long as it is depositable. In addition, when the compound is formed using a coating process to form a thin film, the compound may be used as long as it can be dissolved in a solvent and can be coated.

Hereinafter, a photoelectric device including the compound according to an embodiment is described with reference to drawings.

FIG. 1 is a cross-sectional view showing a photoelectric device according to an embodiment.

Referring to FIG. 1, a photoelectric device 100 according to an example embodiment includes a first electrode 10 and a second electrode 20, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor such as indium tin oxide (ITO) or indium zinc oxide (IZO), or a metal thin layer of a thin single layer or multilayer. When one of the first electrode 10 and the second electrode 20 is a non-light-transmitting electrode, it may be made of, for example, an opaque conductor such as aluminum (Al).

The active layer 30 includes a p-type semiconductor and an n-type semiconductor to form a pn junction, and absorbs external light to generate excitons and then separates the generated excitons into holes and electrons.

The active layer 30 includes the compound represented by Chemical Formula 1. The compound may act as a p-type semiconductor compound in the active layer 30.

The compound may selectively absorb light in a green wavelength region, and the active layer 30 including the compound may have a maximum absorption wavelength ($\lambda_{max}$) in a wavelength region of greater than or equal to about 500 nm, for example greater than or equal to about 510 nm, greater than or equal to about 520 nm, greater than or equal to about 525 nm, or greater than or equal to about 530 nm and less than or equal to about 590 nm, for example less than or equal to about 580 nm, less than or equal to about 570 nm, less than or equal to about 560 nm, less than or equal to about 555 nm, or less than or equal to about 550 nm.

The active layer 30 may exhibit a light absorption curve having a relatively narrow full width at half maximum (FWHM) of about 50 nm to about 100 nm, for example, about 50 nm to about 95 nm. Accordingly, the active layer 30 has high selectivity for light in a green wavelength region.

The active layer 30 may include the compound and C60 in a volume ratio of about 0.9:1 to about 1.1:1, for example 1:1 and may have an absorption coefficient of greater than or equal to about $6.5 \times 10^4$ cm$^{-1}$, for example greater than or equal to about $6.7 \times 10^4$ cm$^{-1}$ to about $10 \times 10^4$ cm$^{-1}$, or about $6.9 \times 10^4$ cm$^{-1}$ to about $10 \times 10^4$ cm$^{-1}$.

The active layer 30 may further include an n-type semiconductor compound for forming pn junction.

The n-type semiconductor compound may be sub-phthalocyanine or a sub-phthalocyanine derivative, fullerene or a fullerene derivative, thiophene or a thiophene derivative, or a combination thereof.

The fullerene may include C60, C70, C76, C78, C80, C82, C84, C90, C96, C240, C540, a mixture thereof, a fullerene nanotube, and the like. The fullerene derivative may refer to compounds of these fullerenes having a substituent. The fullerene derivative may include a substituent such as an alkyl group (e.g., C1 to C30 alkyl group), an aryl group (e.g., C6 to C30 aryl group), a heterocyclic group (e.g., C3 to C30 cycloalkyl group), and the like. Examples of the aryl groups and heterocyclic groups may be a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxazine ring, a phenoxathin ring, a phenothiazine ring, or a phenazine ring.

The sub-phthalocyanine or the sub-phthalocyanine derivative may be represented by Chemical Formula 6.

[Chemical Formula 6]

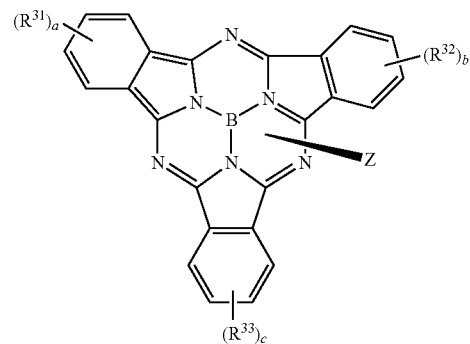

In Chemical Formula 6,
R$^{31}$ to R$^{33}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a halogen-containing group, or a combination thereof,
a, b, and c independently are integers of 1 to 3, and
Z is a monovalent group.
For example, Z may be a halogen or a halogen-containing group, for example F, Cl, an F-containing group, or a Cl-containing group.
The halogen refers to F, C, Br, or I and the halogen-containing group refers to alkyl group (e.g., C1 to C30 alkyl group, C1 to C20 alkyl group, or C1 to C10 alkyl group,) where at least one of hydrogen is replaced by F, Cl, Br, or I.

The thiophene derivative may be for example represented by Chemical Formula 7 or 8, but is not limited thereto.

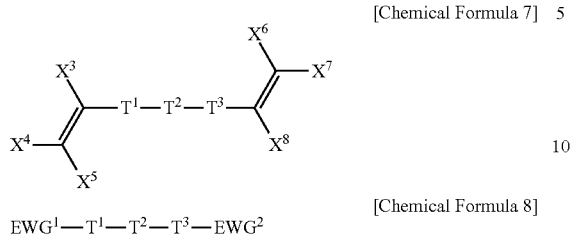

[Chemical Formula 7]

[Chemical Formula 8]

EWG¹—T¹—T²—T³—EWG²

In Chemical Formulas 7 and 8, $T^1$, $T^2$, and $T^3$ are aromatic rings including substituted or unsubstituted thiophene moieties, $T^1$, $T^2$, and $T^3$ are independently present or are fused to each other, $X^3$ to $X^8$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a cyano group, or a combination thereof, and $EWG^1$ and $EWG^2$ may independently be electron withdrawing groups.

For example, in Chemical Formula 7, at least one of $X^3$ to $X^8$ may be an electron withdrawing group, for example a cyano-containing group.

The active layer 30 may further include a second p-type semiconductor compound selectively absorbing green light. The second p-type semiconductor compound may be a compound represented by Chemical Formula 9.

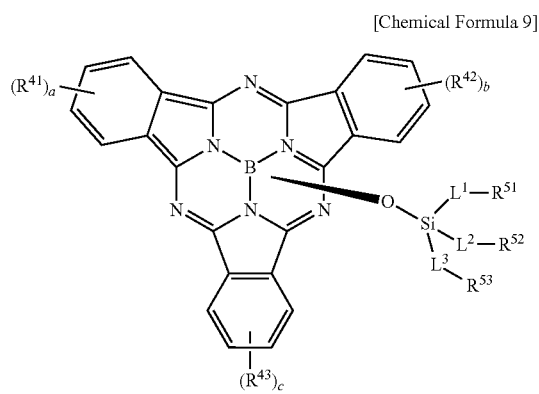

[Chemical Formula 9]

In Chemical Formula 9, $R^{41}$ to $R^{43}$ are independently hydrogen, a substituted or unsubstituted C1 to C30 aliphatic hydrocarbon group, a substituted or unsubstituted C6 to C30 arene group, a substituted or unsubstituted C1 to C30 aliphatic heterocyclic group, a substituted or unsubstituted C2 to C30 aromatic heterocyclic group (heteroarene group), a substituted or unsubstituted C1 to C30 alkoxy group, a substituted or unsubstituted C6 to C30 aryloxy group, a thiol group, a substituted or unsubstituted C1 to C30 alkylthio group, a substituted or unsubstituted C6 to C30 arylthio group, a cyano group, a cyano-containing group, a halogen, a halogen-containing group, a substituted or unsubstituted sulfonyl group (e.g., a substituted or unsubstituted C0 to C30 aminosulfonyl group, a substituted or unsubstituted C1 to C30 alkylsulfonyl group or a substituted or unsubstituted C6 to C30 arylsulfonyl group), or a combination thereof, or two adjacent groups of $R^{41}$ to $R^{43}$ are linked with each other to provide a fused ring, $L^1$ to $L^3$ are independently a single bond, a substituted or unsubstituted C1 to C30 alkylene group, a substituted or unsubstituted C6 to C30 arylene group, a divalent group (e.g., $=CR^{x'}-(CR^xR^y)_p-CR^{y'}(CN)_2$ wherein $R^x$, $R^y$, $R^{x'}$, and $R^{y'}$ are independently hydrogen or a C1 to C10 alkyl group and p is an integer of 0 to 10 or 1 to 10), a substituted or unsubstituted C3 to C30 heterocyclic group, or a combination thereof, $R^{51}$ to $R^{53}$ are independently a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group (e.g., a substituted or unsubstituted C1 to C30 alkylamine group or a substituted or unsubstituted C6 to C30 arylamine group), a substituted or unsubstituted silyl group, or a combination thereof, and a to c are independently an integer ranging from 0 to 4.

The second p-type semiconductor compound may be configured to selectively absorb green light and may be included in an amount of about 500 to about 1500 parts by weight based on 100 parts by weight of the compound represented by Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, and the like.

The intrinsic layer (I layer) may include the compound of Chemical Formula 1 and the n-type semiconductor compound in a volume ratio of about 1:100 to about 100:1. The compound of Chemical Formula 1 and the n-type semiconductor compound may be included in a volume ratio ranging from about 1:50 to about 50:1 within the range, for example, about 1:10 to about 10:1, and such as, about 1:1. When the compound of Chemical Formula 1 and the n-type semiconductor compound have a composition ratio within the range, an exciton may be effectively produced, and a pn junction may be effectively formed.

The p-type layer may include the semiconductor compound of Chemical Formula 1, and the n-type layer may include the n-type semiconductor compound.

The active layer 30 may have a thickness of about 1 nm to about 500 nm and for example, about 5 nm to about 300 nm. When the active layer 30 has a thickness within the range, the active layer may effectively absorb light, effectively separate holes from electrons, and deliver them, thereby effectively improving photoelectric conversion efficiency. A desirable thickness of the active layer 30 may be, for example, determined by an absorption coefficient of the active layer 30, and may be, for example, a thickness being capable of absorbing light of at least about 70% or more, for example about 80% or more, and for another example about 90% or more (e.g., less than 100%).

In the photoelectric device 100, when light enters from the first electrode 10 and/or second electrode 20, and when the active layer 30 absorbs light in a desired and/or alternatively predetermined wavelength region, excitons may be produced from the inside. The excitons are separated into holes and electrons in the active layer 30, and the separated holes are transported to an anode that is one of the first electrode 10 and the second electrode 20 and the separated electrons are transported to the cathode that is the other of and the first electrode 10 and the second electrode 20 so as to flow a current in the photoelectric device.

Hereinafter, a photoelectric device according to another embodiment is described with reference to FIG. 2.

Figure 2:
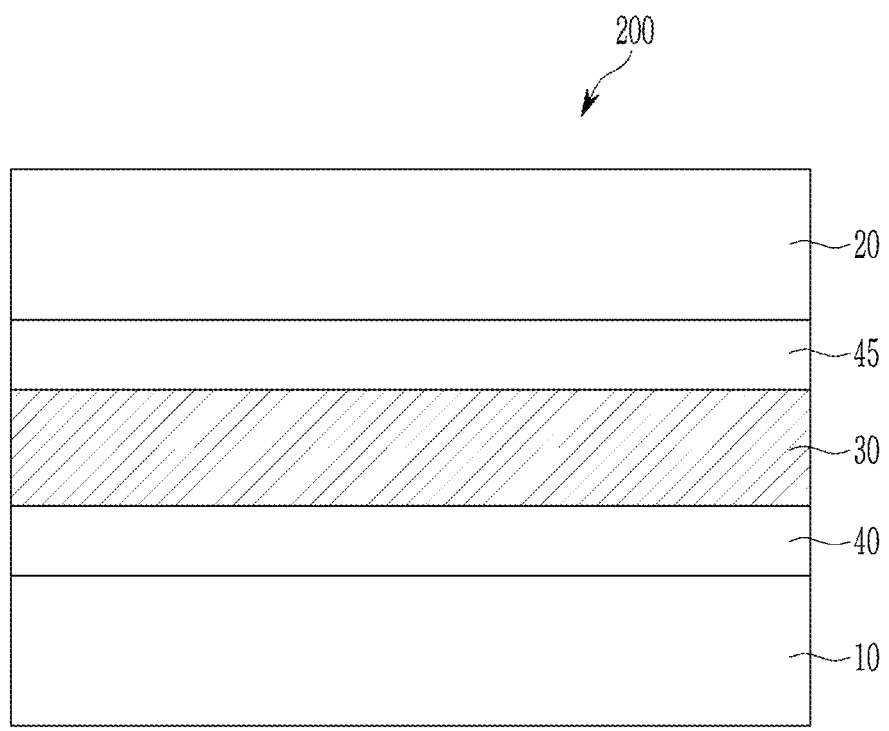
FIG. 2 is a cross-sectional view showing a photoelectric device according to another embodiment.

FIG. 2 is a cross-sectional view showing a photoelectric device according to another example embodiment.

Referring to FIG. 2, a photoelectric device 200 according to the present embodiment includes a first electrode 10 and a second electrode 20 facing each other, and an active layer 30 between the first electrode 10 and the second electrode 20, like the above embodiment.

However, the photoelectric device 200 according to the present embodiment further includes charge auxiliary layers 40 and 45 between the first electrode 10 and the active layer 30, and the second electrode 20 and the active layer 30, unlike the above embodiment. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for preventing electron transport, an electron injection layer (EIL) for facilitating electron injection, an electron transport layer (ETL) for facilitating electron transport, and a hole blocking layer (HBL) for preventing hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole transport layer (HTL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 45 may be omitted.

The photoelectric device may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
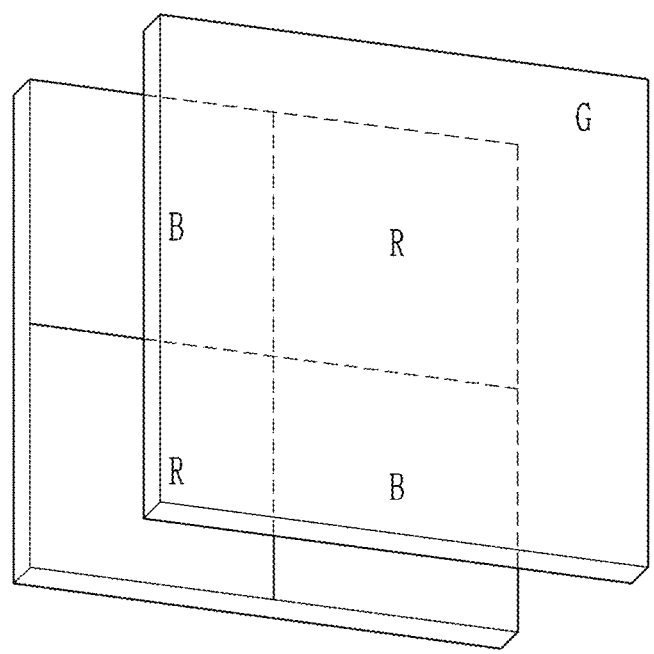
FIG. 3 is a schematic top plan view showing an organic CMOS image sensor according to an embodiment.
Figure 4:
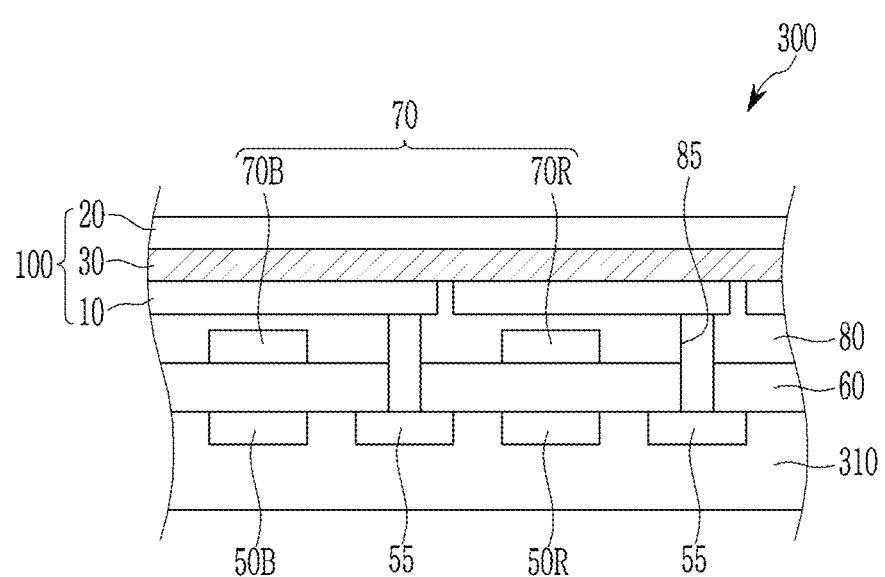
FIG. 4 is a cross-sectional view showing the organic CMOS image sensor of FIG. 3.

FIG. 3 is a schematic top plan view showing an organic CMOS image sensor according to an example embodiment, and FIG. 4 is a cross-sectional view showing the organic CMOS image sensor of FIG. 3.

Referring to FIGS. 3 and 4, an organic CMOS image sensor 300 according to an example embodiment includes a semiconductor substrate 310 integrated with blue and red photo-sensing devices 50B and 50R, a transmission transistor (not shown), and a charge storage 55, a lower insulation layer 60, a color filter layer 70, an upper insulation layer 80, and a photoelectric device 100.

The semiconductor substrate 310 may be a silicon substrate, and is integrated with the blue and red photo-sensing devices 50B and 50R, the transmission transistor (not shown), and the charge storage 55. The blue and red photo-sensing devices 50B and 50R may be photodiodes.

The blue and red photo-sensing devices 50B and 50R, the transmission transistor, and/or the charge storage 55 may be integrated in each pixel, and as shown in the drawing, the blue and red photo-sensing devices 50B and 50R may be respectively included in a blue pixel and a red pixel and the charge storage 55 may be included in a green pixel.

The blue and red photo-sensing devices 50B and 50R sense light, the information sensed by the photo-sensing devices may be transferred by the transmission transistor, the charge storage 55 is electrically connected to the photoelectric device 100, and the information of the charge storage 55 may be transferred by the transmission transistor.

In the drawings, the blue and red photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 310. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the blue and red photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70B formed in the blue pixel and selectively transmitting blue light and a red filter 70R formed in the red pixel and selectively transmitting red light. In an embodiment, a cyan filter 70C and a yellow filter 70Y may be disposed instead of the blue filter 70B and red filter 70R. In the present embodiment, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The aforementioned photoelectric device 100 is formed on the upper insulation layer 80. The photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs and/or senses light in a green wavelength region and replaces a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in the blue and red photo-sensing devices 50B and 50R.

As described above, the photoelectric devices selectively absorbing light in a green wavelength region are stacked and thereby a size of an image sensor may be decreased and a down-sized image sensor may be realized.

As described above, when the compound represented by the Chemical Formula 1 is used as a semiconductor compound, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased and sensitivity may be increased.

In an embodiment, in FIG. 4, additional color filters may be further disposed on the photoelectric device 100. The additional color filters may include a blue filter 70B and a red filter 70R or a cyan filter 70C and a yellow filter 70Y.

Figure 5:
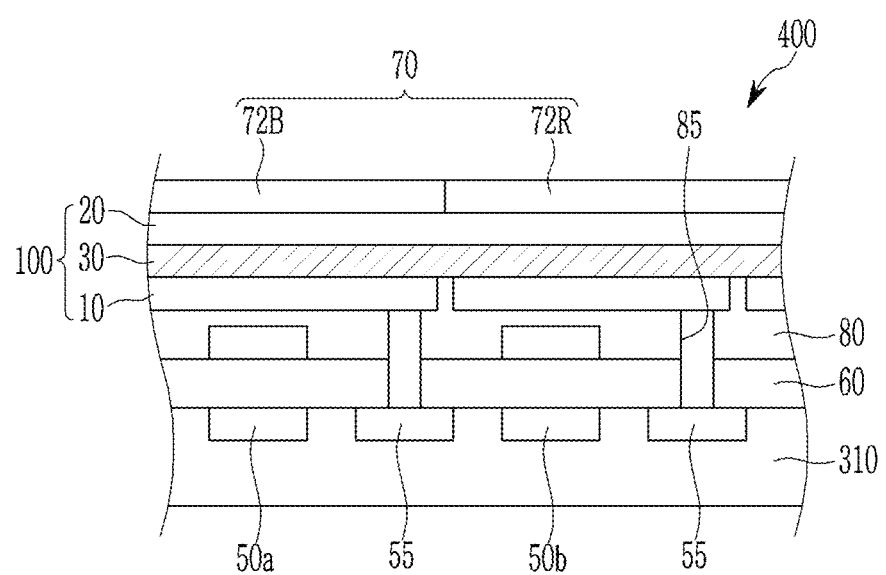
FIG. 5 is a schematic cross-sectional view showing an organic CMOS image sensor according to another embodiment.

The organic CMOS image sensor with the color filters disposed on the photoelectric device is shown in FIG. 5. FIG. 5 is a schematic cross-sectional view showing an organic CMOS image sensor according to an embodiment. Referring to FIG. 5, an organic CMOS image sensor 400 has the same structure as FIG. 4 except that a color filter layer 72 including the blue filter 72B and the red filter 72R is disposed on the photoelectric device 100. Instead of the blue filter 72B and the red filter 72R, the cyan filter 72C and the yellow filter 72Y may be disposed respectively.

Figure 6:
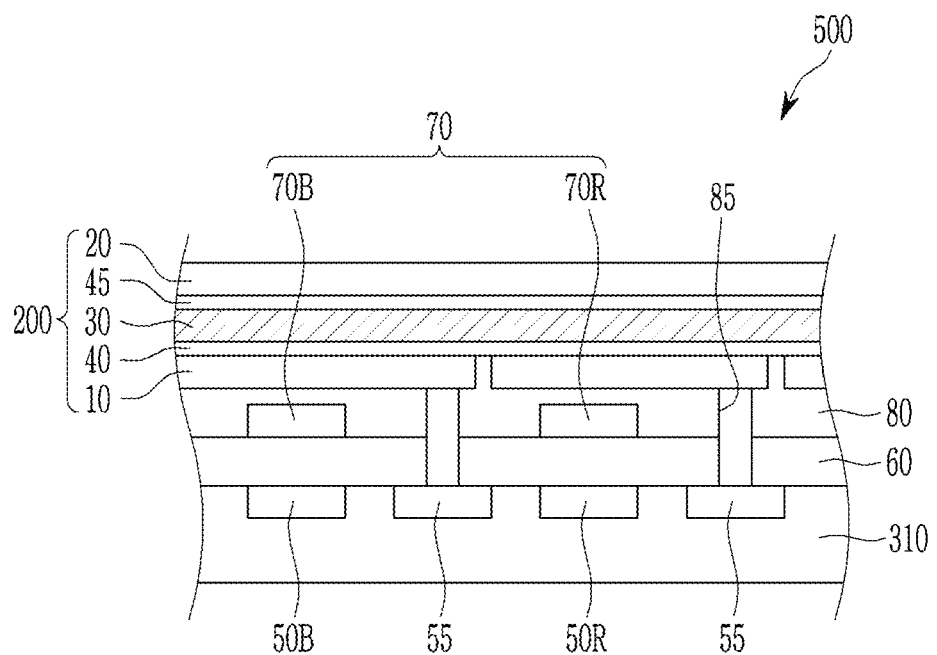
FIG. 6 is a schematic cross-sectional view showing an organic CMOS image sensor according to another embodiment.

In FIGS. 4 and 5, the photoelectric device 100 of FIG. 1 is included, but it is not limited thereto, and thus the photoelectric device 200 of FIG. 2 may be applied in the same manner. FIG. 6 is a cross-sectional view showing an organic CMOS image sensor 500 to which the photoelectric device 200 is applied.

Figure 7:
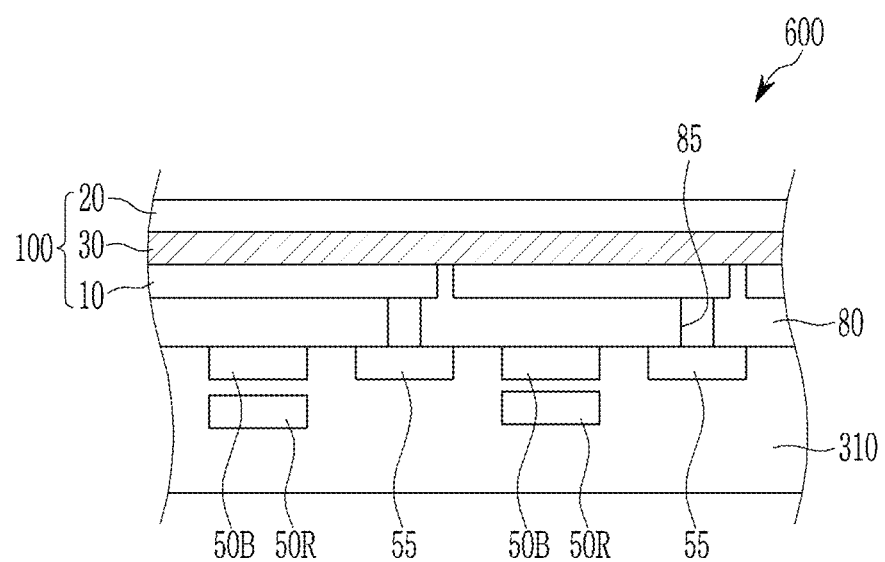
FIG. 7 is a schematic cross-sectional view showing an organic CMOS image sensor according to another embodiment.

FIG. 7 is a schematic cross-sectional view showing an organic CMOS image sensor according to another embodiment.

Referring to FIG. 7, the organic CMOS image sensor 600 includes a semiconductor substrate 310 integrated with blue and red photo-sensing devices 50B and 50R, a transmission transistor (not shown), and a charge storage 55, an insulation layer 80, and a photoelectric device 100, like the example embodiment illustrated in FIG. 5.

However, the organic CMOS image sensor 600 according to the embodiment includes the blue photo-sensing device 50B and the red photo-sensing device 50R that are stacked and does not include a color filter layer 70, unlike the aforementioned embodiments. The blue photo-sensing device 50B and the red photo-sensing device 50R are electrically connected with the charge storage 55, and the information of the charge storage 55 may be transferred by the transmission transistor (not shown). The blue photo-sensing device 50B and the red photo-sensing device 50R may selectively absorb light in each wavelength region depending on a stack depth.

As described above, the photoelectric devices selectively absorbing light in a green wavelength region are stacked and the red photo-sensing device and the blue photo-sensing device are stacked, and thereby a size of an image sensor may be decreased and a down-sized image sensor may be realized. As described above, the photoelectric device 100 has improved green wavelength selectivity, and crosstalk caused by unnecessary absorption of light in a wavelength region except green may be decreased while increasing sensitivity.

In FIG. 7, the photoelectric device 100 of FIG. 1 is included, but it is not limited thereto, and thus the photoelectric device 200 of FIG. 2 may be applied in the same manner. In other words, the organic CMOS image sensor 600 may be modified to include the photoelectric device 200 of FIG. 2 instead of the photoelectric device 100 of FIG. 1.

Figure 8:
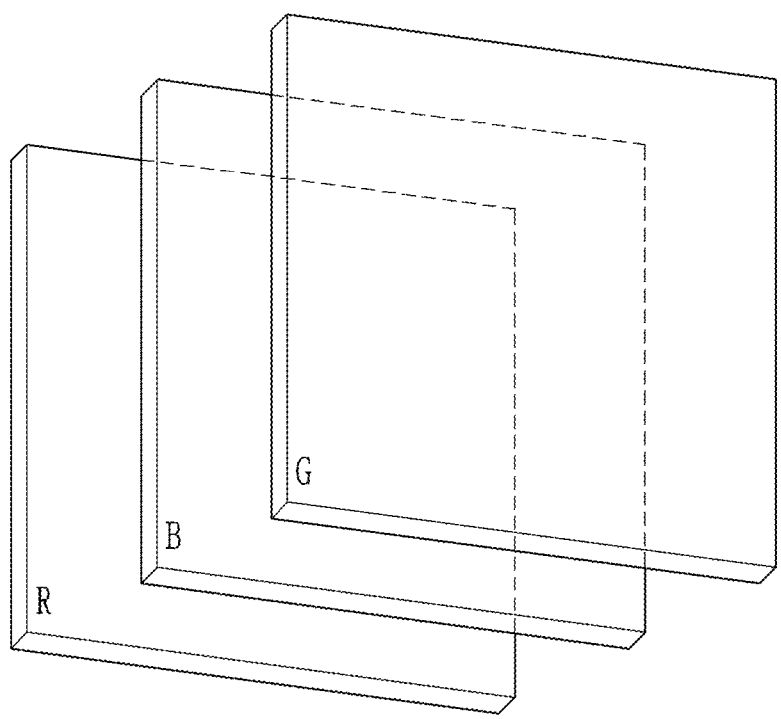
FIG. 8 is a schematic top plan view showing an organic CMOS image sensor according to another embodiment.

FIG. 8 is a schematic top plan view showing an organic CMOS image sensor according to another example embodiment.

Referring to FIG. 8, the organic CMOS image sensor according to the present embodiment includes a green photoelectric device (G) selectively absorbing light in a green wavelength region, a blue photoelectric device (B) selectively absorbing light in a blue wavelength region, and a red photoelectric device (R) selectively absorbing light in a red wavelength region that are stacked.

In the drawing, the red photoelectric device, the green photoelectric device, and the blue photoelectric device are sequentially stacked, but the stacking order may be changed without limitation.

The green photoelectric device may be the aforementioned photoelectric device 100 or photoelectric device 200, the blue photoelectric device may include electrodes facing each other and an active layer interposed therebetween and including an organic material selectively absorbing light in a blue wavelength region, and the red photoelectric device may include electrodes facing each other and an active layer interposed therebetween and including an organic material selectively absorbing light in a red wavelength region.

As described above, the green photoelectric device (G) selectively absorbing light in a green wavelength region, the blue photoelectric device (B) selectively absorbing light in a blue wavelength region, and the red photoelectric device (R) selectively absorbing light in a red wavelength region are stacked, and thereby a size of an image sensor may be decreased and a down-sized image sensor may be realized.

The image sensor absorbs light in an appropriate wavelength region and may show both of improved sensitivity (YSNR10) and color reproducibility ($\Delta E^*ab$) despite a stacked structure.

Herein, the YSNR10 indicates sensitivity of the image sensor, which is measured in a method described in Juha Alakarhu's "Image Sensors and Image Quality in Mobile Phones" printed in 2007 International Image Sensor Workshop (Ogunquit Maine, USA) but minimum illuminance expressed by lux at a ratio of 10 between signal and noise. Accordingly, the smaller the YSNR10 is, the higher sensitivity is.

On the other hand, the color reproducibility (ΔE*ab) shows a difference from standard colors in an X-Rite chart, and the ΔE*ab is defined as a distance between two points on a L*a*b* color space by CIE (Commission International de L'Eclairage) in 1976. For example, the color difference may be calculated according to Equation 1.

$$\Delta E = \sqrt{(\Delta L^*)^2 + (\Delta a^*)^2 + (\Delta b^*)^2}$$ [Equation 1]

In Equation 1,

ΔL* denotes a change of a color coordinate L* compared with the color coordinate L* at room temperature (about 20° C. to about 25° C.), Δa* denotes a change of a color coordinate a* compared with the color coordinate a* at room temperature, and Δb* denotes a change of a color coordinate b* compared with the color coordinate b* at room temperature.

In order to manufacture an image sensor having high sensitivity and high color reproducibility, it is require that YSNR10≤100 lux at ΔE*ab≤3. Herein, the compound may realize YSNR10≤100 lux of sensitivity and color reproducibility at ΔE*ab≤3.

The image sensor may be applied to various electronic devices, for example, a mobile phone, a digital camera, and the like but is not limited thereto.

Figure 9:
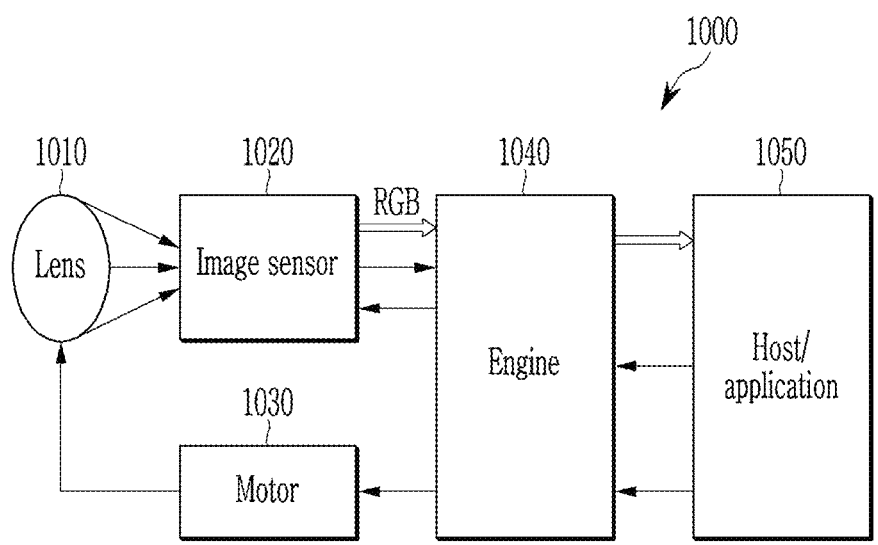
FIG. 9 is a block diagram of a digital camera including an image sensor according to an embodiment.

FIG. 9 is a block diagram of a digital camera including an image sensor according to an embodiment.

Referring to FIG. 9, a digital camera 1000 includes a lens 1010, an image sensor 1020, a motor 1030, and an engine 1040. The image sensor 1020 may be one of image sensors according to embodiments shown in FIGS. 3 to 8.

The lens 1010 concentrates incident light on the image sensor 1020. The image sensor 1020 generates RGB data for received light through the lens 1010.

In some embodiments, the image sensor 1020 may interface with the engine 1040.

The motor 1030 may adjust the focus of the lens 1010 or perform shuttering in response to a control signal received from the engine 1040. The engine 1040 may control the image sensor 1020 and the motor 1030.

The engine 1040 may be connected to a host/application 1050.

Figure 10:
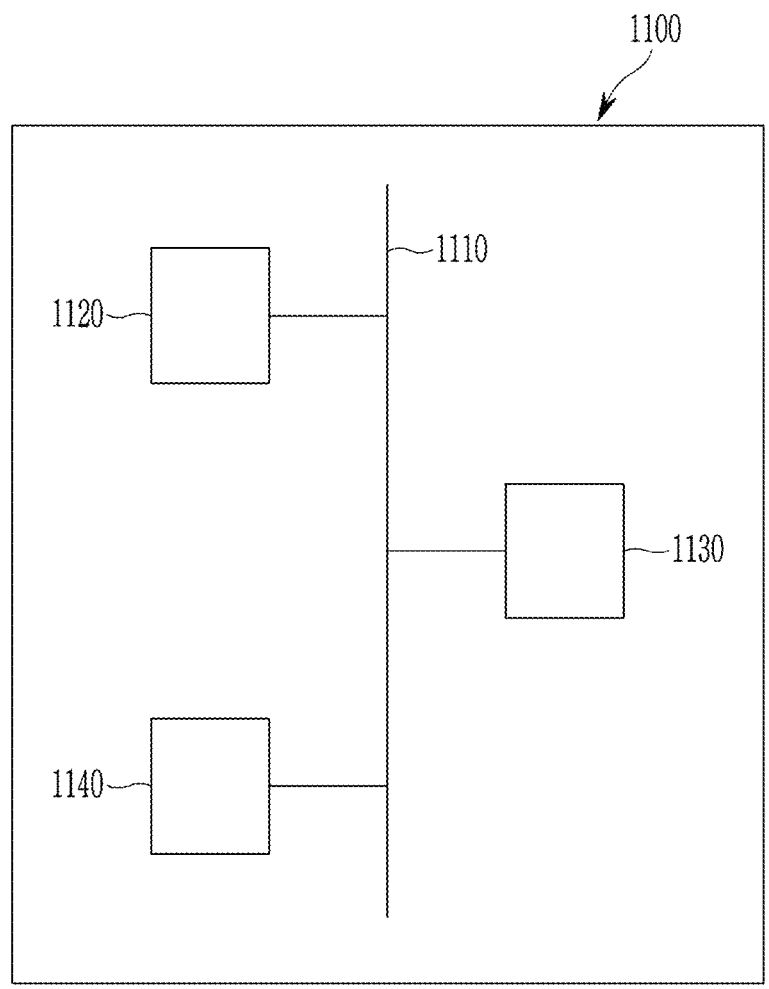
FIG. 10 is a schematic diagram of an electronic device according to example embodiments.

FIG. 10 is a schematic diagram of an electronic device according to example embodiments.

Referring to FIG. 10, an electronic device 1100 may include a processor 1120, a memory 1130, and an image sensor 1140 that are electrically coupled together via a bus 1110. The image sensor 1140 may be one according to one of the aforementioned embodiments. The memory 1130 may be a non-transitory computer readable medium and may store a program of instructions. The memory 1130 may be a nonvolatile memory, such as a flash memory, a phase-change random access memory (PRAM), a magneto-resistive RAM (MRAM), a resistive RAM (ReRAM), or a ferro-electric RAM (FRAM), or a volatile memory, such as a static RAM (SRAM), a dynamic RAM (DRAM), or a synchronous DRAM (SDRAM). The processor 1120 may execute the stored program of instructions to perform one or more functions. For example, the processor 1120 may be configured to process electrical signals generated by the image sensor 1140. The processor 1120 may include processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc. The processor 1120 may be configured to generate an output (e.g., an image to be displayed on a display interface) based on such processing.

Hereinafter, the embodiments are illustrated in more detail with reference to examples. However, these examples are non-limiting, and the present disclosure is not limited thereto.

Synthesis Example 1: Synthesis of Compound Represented by Chemical Formula 1-1

[Chemical Formula 1-1]

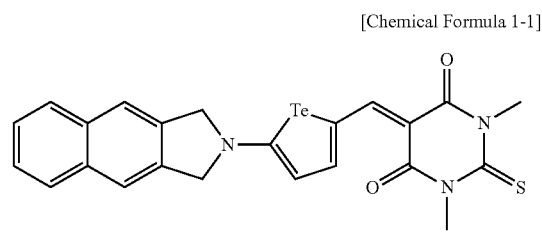

[Reaction Scheme 1-1]

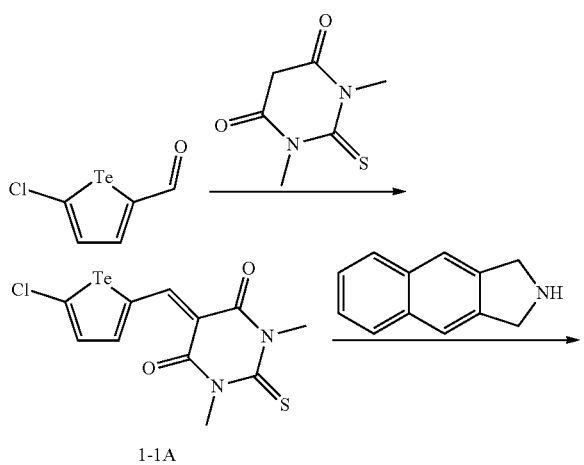

1-1A

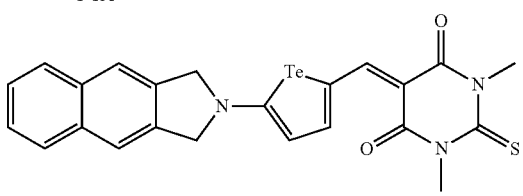

1-1

(i) Synthesis of Compound 1-1A 3.1 g (12.6 mmol) of 5-chlorotellurophene-2-carbaldehyde and 2.6 g (15.1 mmol) of 1,3-dimethyl-2-thioxodihydropyrimidine-4,6(1H,5H)-dione (also referred to as 1,3-dimethyl-2-thiobarbituric acid) are heated under reflux in 50 ml of ethanol for 6 hours. The obtained product is separated and purified through silica gel column chromatography (methylene chloride) to obtain 4.5 g (Yield of 90%) of Compound 1-1A (5-((5-chlorotellurophen-2-yl)methylene)-1,3-dimethyl-2-thioxodihydropyrimidine-4,6(1H,5H)-dione).

(ii) Synthesis of Compound Represented by Chemical Formula 1-1

2.2 g (5.7 mmol) of Compound 1-1A and 1.9 g (11.34 mmol) of 2,3-dihydro-1H-benzo[f]isoindole are added in a dropwise fashion to 200 ml of 1,4-dioxane, and 0.01 ml of triethylamine is added thereto and then, stirred at 100° C. for 12 hours. The obtained mixture is cooled down to room temperature (24° C.) to precipitate products followed by filtering and purifying. Chloroform is used for recrystallization to obtain 2.00 g (Yield of 67.0%) of a compound represented by Chemical Formula 1-1.

$^1$H-NMR (500 MHz, Methylene Chloride-d2): δ 8.46 (s, 1H), 8.27 (d, 1H), 7.84 (m, 2H), 7.71 (s, 2H), 7.45 (m, 2H), 6.94 (d, 1H), 4.35 (s, 4H), 3.71 (s, 1H), 3, 66 (s, 1H).

Synthesis Example 2: Synthesis of Compound Represented by Chemical Formula 1-2

[Chemical Formula 1-2]

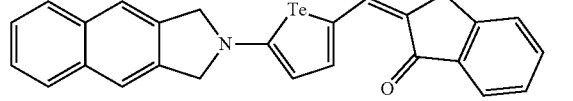

[Reaction Scheme 1-2]

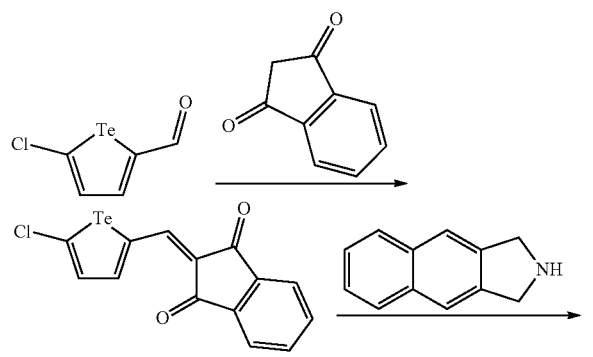

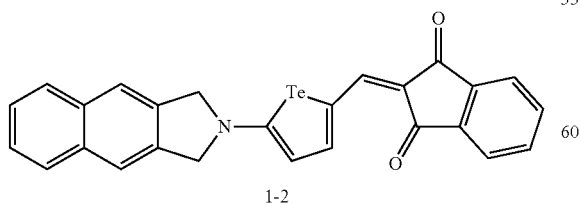

1-2

(i) Synthesis of Compound 1-2A 3.3 g (13.5 mmol) of 5-chlorotellurophene-2-carbaldehyde and 2.4 g (16.2 mmol) of 1H-indene-1,3(2H)-dione are heated under reflux in 50 ml of ethanol for 6 hours. The obtained product is separated and purified through silica gel column chromatography (methylene chloride) to obtain 4.4 g (Yield=88%) of Compound 1-2A (2-((5-chlorotellurophen-2-yl)methylene)-1H-indene-1,3(2H)-dione).

(ii) Synthesis of Compound Represented by Chemical Formula 1-2

2.2 g (6.0 mmol) of Compound 1-2A and 2.0 g (11.9 mmol) of 2,3-dihydro-1H-benzo[f]isoindole are added in a dropwise fashion to 200 ml of 1,4-dioxane, and 0.01 ml of triethylamine is added thereto and then, stirred at 100° C. for 12 hours. The resultant is cooled down to room temperature (24° C.) to precipitate products followed by filtering and purifying. Chloroform is used for recrystallization to obtain 2.1 g (Yield of 70.0%) of a compound represented by Chemical Formula 1-2.

$^1$H-NMR (500 MHz, Methylene Chloride-d2): δ 8.43 (s, 1H), 8.24 (d, 1H), 7.82 (m, 2H), 7.7-7.68 (m, 6H), 7.41 (m, 2H), 7.04 (d, 1H), 4.3 (s, 4H).

Synthesis Example 3: Synthesis of Compound Represented by Chemical Formula 1-3

[Chemical Formula 1-3]

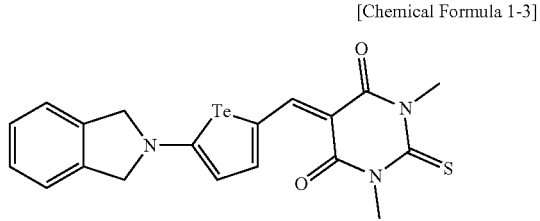

[Reaction Scheme 1-3]

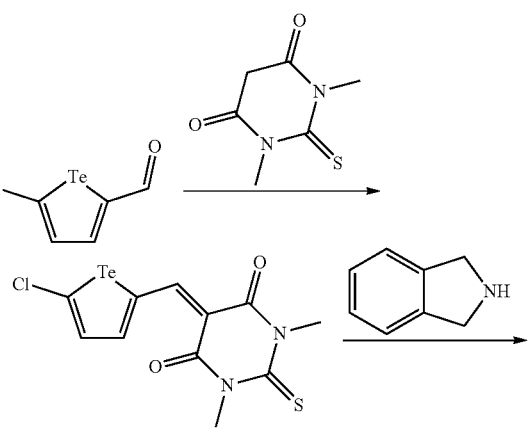

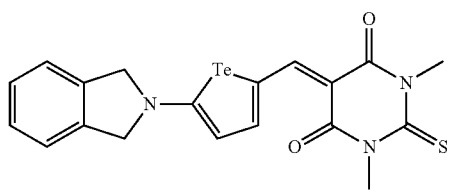

1-3

(i) Synthesis of Compound 1-1A 3.1 g (12.6 mmol) of 5-chlorotellurophene-2-carbaldehyde and 2.6 g (15.1 mmol) of 1,3-dimethyl-2-thioxodihydropyrimidine-4,6(1H,5H)-dione are heated under reflux in 50 ml of ethanol for 6 hours. The obtained product is separated and purified through silica gel column chromatography (methylene chloride) to obtain 4.5 g (Yield of 90%) of Compound 1-1A 5-((5-chlorotellurophen-2-yl)methylene)-1,3-dimethyl-2-thioxodihydropyrimidine-4,6(1H,5H)-dione).

(ii) Synthesis of Compound 1-3

2.4 g (6.0 mmol) of Compound 1-1A and 1.4 g (12.0 mmol) of isoindole are added to 200 ml of 1,4-dioxane in a dropwise fashion, and 0.01 ml of triethylamine is added thereto and then, stirred at 100° C. for 12 hours. The resultant is cooled down to room temperature (24° C.) to precipitate products followed by filtering and purifying. Chloroform is used for recrystallization to obtain 2.4 g (Yield of 80.0%) of a compound represented by Chemical Formula 1-3.

$^1$H-NMR (500 MHz, Methylene Chloride-d2): δ 8.46 (s, 1H), 8.27 (d, 1H), 7.69 (dd, 2H), 7.45 (dd, 2H), 6.94 (d, 1H), 4.35 (s, 4H), 3.71 (s, 1H), 3.63 (s, 1H).

Synthesis Example 4: Synthesis of Compound Represented by Chemical Formula 1-4

(i) Synthesis of Compound 1-2A 3.3 g (13.5 mmol) of 5-chlorotellurophene-2-carbaldehyde and 2.4 g (16.2 mmol) of 1H-indene-1,3(2H)-dione are heated under reflux in 50 ml of ethanol for 6 hours. The obtained product is separated and purified through silica gel column chromatography (methylene chloride) to obtain 4.4 g (Yield of 88%) of Compound 1-2A (2-((5-chlorotellurophen-2-yl)methylene)-1H-indene-1,3(2H)-dione).

(ii) Synthesis of Compound Represented by Chemical Formula 1-4

2.2 g (6.0 mmol) of Compound 1-2A and 1.4 g (11.9 mmol) of isoindole are added to 200 ml of 1,4-dioxane in a dropwise fashion, and 0.01 ml of triethylamine is added thereto and then, stirred at 100° C. for 12 hours. The resultant is cooled down to room temperature (24° C.) to precipitate products followed by filtering and purifying. Chloroform is used for recrystallization to obtain 2.2 g (Yield of 73.0%) of a compound represented by Chemical Formula 1-4.

$^1$H-NMR (500 MHz, Methylene Chloride-d2): δ 8.45 (s, 1H), 8.19 (d, 1H), 7.7-7.68 (m, 8H), 7.04 (d, 1H), 4.3 (s, 4H).

Reference Synthesis Example 1: Synthesis of Compound Represented by Chemical Formula 2-1 (2-((5-(10H-phenoselenazin-10-yl)tellurophen-2-yl)methylene)-1H-indene-1,3(2H)-dione)

[Chemical Formula 1-4]

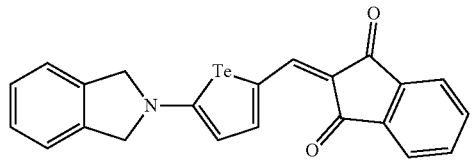

[Reaction Scheme 1-4]

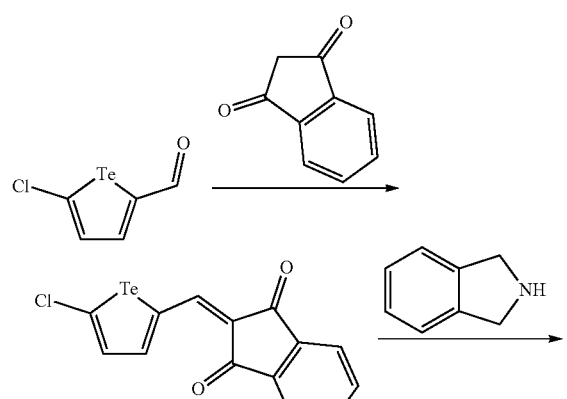

1-2A

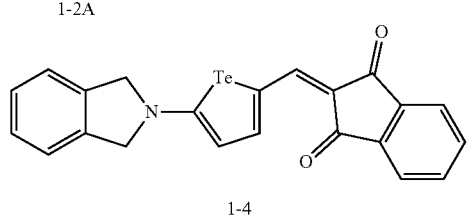

1-4

[Chemical Formula 2-1]

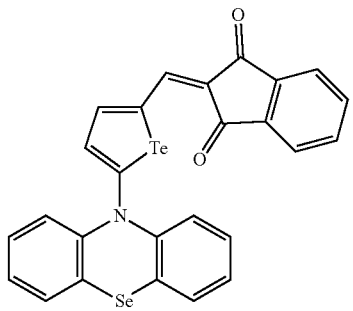

[Reaction Scheme 2-1]

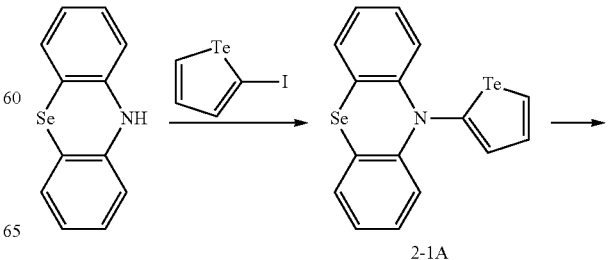

2-1A

71

-continued

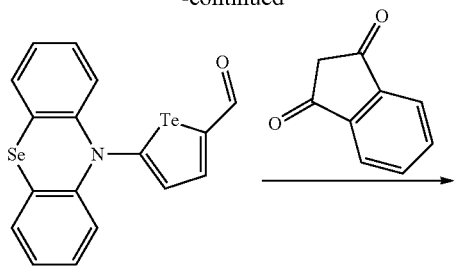

2-1B

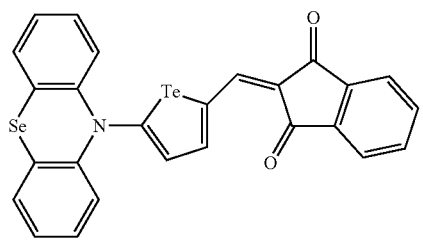

2-1

(i) Synthesis of Compound 2-1A 10.0 g (32.7 mmol) of 2-iodotellurophene and 6.17 g (25.2 mmol) of 10H-phenoselenazine are heated under reflux in 100 ml of anhydrous toluene under presence of 5 mol % of bis(dibenzylideneacetone)palladium (Pd(dba)$_2$), 5 mol % of tri-tert-butylphosphine (P(tBu)$_3$), and 2.66 g (27.7 mmol) of sodium tert-butanolate (NaOtBu) for 2 hours. The obtained product is separated and purified through silica gel column chromatography (a volume ratio of toluene:hexane=1:4) to obtain 4.25 g (Yield of 39.8%) of Compound 2-1A (10-(tellurophen-2-yl)-10H-phenoselenazine).

(ii) Synthesis of Compound 2-1B 1.84 ml of phosphoryl chloride is added to 6.0 ml of N,N-dimethylformamide in a dropwise fashion at −15° C. and then, stirred at room temperature (24° C.) for 2 hours. The resultant is slowly added to a mixture of 200 ml of dichloromethane and 4.25 g of Compound 2-1A in a dropwise fashion at −15° C. and then, stirred at room temperature (24° C.) for 30 minutes and concentrated under a reduced pressure. Subsequently, 100 ml of water is added thereto, an aqueous sodium hydroxide solution is added thereto, until the pH becomes 14 and then, stirred at room temperature (24° C.) for 2 hours. An organic layer extracted by using dichloromethane is washed with an aqueous sodium chloride solution and then, dried by adding anhydrous magnesium sulfate thereto. The obtained product is separated and purified through silica gel column chromatography (a volume ratio of hexane:ethyl acetate=4:1) to obtain 2.50 g (Yield of 55.2%) of Compound 2-1B (5-(10H-phenoselenazin-10-yl) tellurophene-2-carbaldehyde).

(iii) Synthesis of Compound Represented by Chemical Formula 2-1

1.90 g (4.21 mmol) of Compound 2-1B is suspended in ethanol, 0.74 g (5.05 mmol) of 1H-indene-1,3(2H)-dione is added thereto and then, reacted at 50° C. for 2 hours to obtain 2.02 g (Yield of 82.8%) of a compound represented by Chemical Formula 2-1. The obtained compound is purified through sublimation up to purity of 99.9%.

$^1$H-NMR (500 MHz, Methylene Chloride-d2): δ 7.87 (s, 1H), 7.72 (m, 6H), 7.49 (m, 4H), 7.34 (m, 3H), 6.82 (d, 1H).

72

Reference Synthesis Example 2: Synthesis of Compound Represented by Chemical Formula 2-2 (5-((5-(10H-phenoselenazin-10-yl)tellurophen-2-yl)methylene)-1,3-dimethyl-2-thioxodihydropyrimidine-4,6(1H,5H)-dione)

[Chemical Formula 2-2]

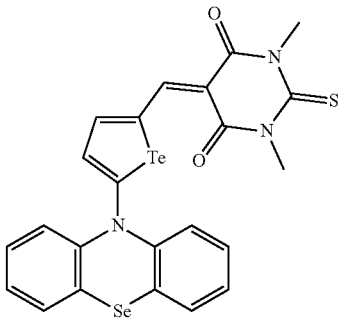

[Reaction Scheme 2-2]

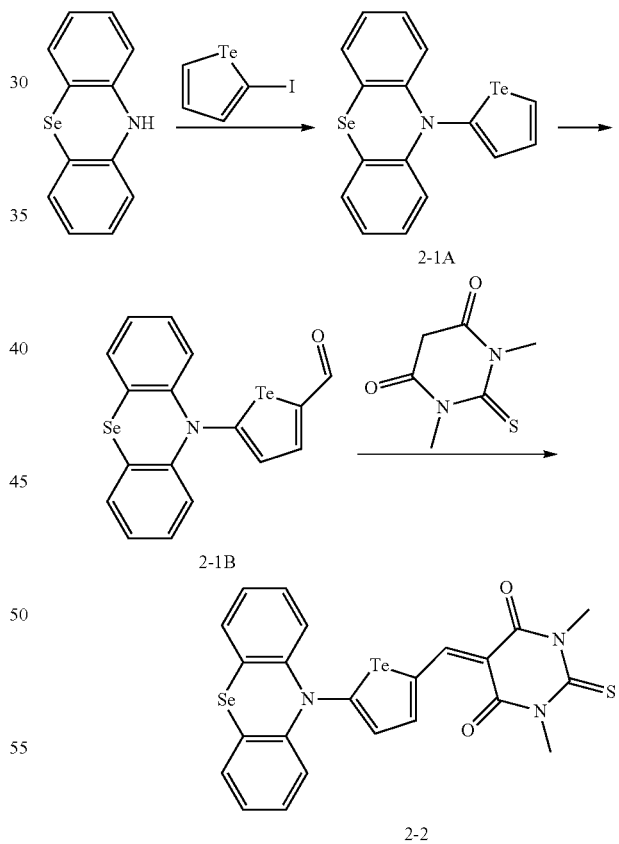

(i) Synthesis of Compound 2-1A 10.0 g (32.7 mmol) of 2-iodotellurophene and 6.17 g (25.2 mmol) of 10H-phenoselenazine are heated under reflux in 100 ml of anhydrous toluene under the presence of 5 mol % of Pd(dba)$_2$, 5 mol % of P(tBu)$_3$, and 2.66 g (27.7 mmol) of NaOtBu for 2 hours. The obtained product is separated and purified through silica gel column chromatography (a volume ratio of toluene:hexane=1:4) to obtain 4.25 g (Yield of 19.6%) of Compound 2-1A (10-(tellurophen-2-yl)-10H-phenoselenazine).

(ii) Synthesis of Compound 2-1B 1.84 ml of phosphoryl chloride is added to 6.0 ml of N,N-dimethylformamide in a dropwise fashion at −15° C. and then, stirred at room temperature (24° C.) for 2 hours. The resultant is slowly added to a mixture of 180 ml of dichloromethane and 4.25 g of Compound 2-1A at −15° C. and then, stirred at room temperature (24° C.) for 30 minutes and concentrated under a reduced pressure. Subsequently, 100 ml of water is added thereto, and an aqueous sodium hydroxide solution is added thereto, until the pH becomes 14 and then, stirred at room temperature (24° C.) for 2 hours. An organic layer extracted by using dichloromethane is washed with an aqueous sodium chloride solution and then, dried by adding anhydrous magnesium sulfate thereto. The obtained product is separated and purified through silica gel column chromatography (a volume ratio of hexane:ethyl acetate=4:1) to obtain 2.50 g (Yield of 55.2%) of Compound 2-1B (5-(10H-phenoselenazin-10-yl)tellurophene-2-carbaldehyde).

(iii) Synthesis of Compound Represented by Chemical Formula 2-2

1.90 g (4.21 mmol) of Compound 2-1B is suspended in ethanol, and 0.87 g (5.05 mmol) of 1,3-dimethyl-2-thioxo-dihydropyrimidine-4,6(1H,5H)-dione is added thereto and then, reacted at 50° C. for 2 hours to obtain 2.02 g (Yield=79.2%) of a compound represented by Chemical Formula 2-2. The obtained compound is purified through sublimation up to purity of 99.9%.

$^1$H-NMR (500 MHz, Methylene Chloride-d2): δ 8.29 (s, 1H), 7.83 (d, 1H), 7.73 (d, 2H), 7.51 (d, 2H), 7.37 (t, 2H), 6.99 (t, 2H), 5.32 (d, 1H), 3.67 (d, 6H).

Reference Synthesis Example 3: Synthesis of Compound Represented by Chemical Formula 2-3

[Chemical Formula 2-3]

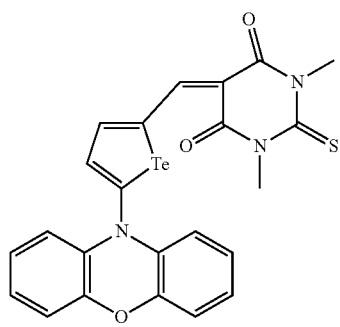

[Reaction Scheme 2-3]

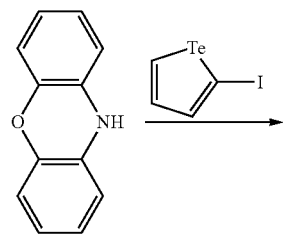

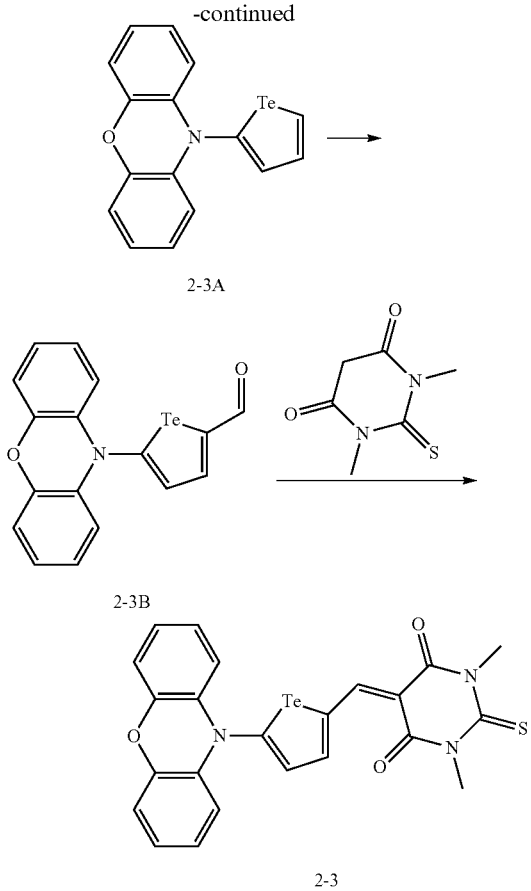

(i) Synthesis of Compound 2-3A 15.2 g (49.9 mmol) of 2-iodotellurophene and 7.6 g (41.6 mmol) of 10H-phenoxazine are heated under reflux in 150 ml of anhydrous toluene under the presence of 5 mol % of Pd(dba)$_2$, 5 mol % of P(tBu)$_3$, and 10.4 g (107.9 mmol) of NaOtBu for 2 hours. The obtained product is separated and purified through silica gel column chromatography (a volume ratio of toluene:hexane=1:4) to obtain 9.1 g (Yield of 61.0%) of Compound 2-3A (10-(tellurophen-2-yl)-10H-phenoxazine).

(ii) Synthesis of Compound 2-3B 1.25 ml (13.4 mmol) of phosphoryl chloride is added to 4.0 ml (51.4 mmol) of N,N-dimethylformamide in a dropwise fashion at −15° C. and then, stirred at room temperature (24° C.) for 2 hours. The obtained mixture is slowly added dropwise to a mixture of 200 ml of dichloromethane and 3.7 g (10.6 mmol) of Compound 2-3A at −15° C. and then, stirred at room temperature (24° C.) for 2 hours. Subsequently, 100 ml of water is added thereto, and an aqueous sodium hydroxide solution is added thereto, until the pH becomes 14 and then, stirred at room temperature (24° C.) for 2 hours. An organic layer extracted with dichloromethane is washed with an aqueous sodium chloride solution and then, dried with anhydrous magnesium sulfate. The obtained product is separated and purified through silica gel column chromatography (a volume ratio of hexane:ethylacetate=4:1) to obtain 3.5 g (Yield of 88.0%) of Compound 2-3B (5-(10H-phenoxazin-10-yl)tellurophene-2-carbaldehyde).

(iii) Synthesis of Compound Represented by Chemical Formula 2-3

1.18 g (3.0 mmol) of Compound 2-3B is suspended in ethanol, and 0.63 g (3.6 mmol) of 1,3-dimethyl-2-thioxodihydropyrimidine-4,6(1H,5H)-dione is added thereto and then, heated under reflux at 50° C. for 2 hours. The resultant is cooled down to room temperature (24° C.), and hexane is added thereto. When powder is formed therein, the powder is filtered and then, the product from the filtrate is separated and purified through silica gel column chromatography (dichloromethane) to obtain 1.25 g (Yield of 83.0%) of a compound represented by Chemical Formula 2-3. The obtained compound is purified through sublimation up to purity of 99.9%.

$^1$H-NMR (500 MHz, Methylene Chloride-d2): δ 8.50 (s, 1H), 8.31 (d, 1H), 7.81 (d, 2H), 7.48 (t, 2H), 7.43-7.36 (m, 4H), 7.06 (d, 1H), 3.7 (d, 6H).

Reference Synthesis Example 4: Synthesis of Compound Represented by Chemical Formula 2-4

[Chemical Formula 2-4]

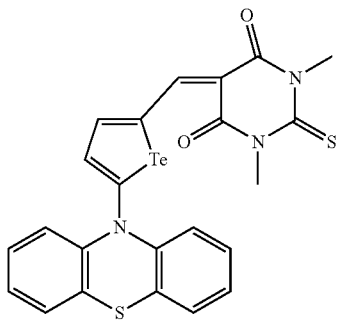

[Reaction Scheme 2-4]

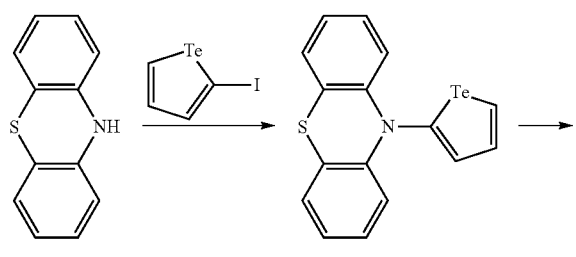

2-4A

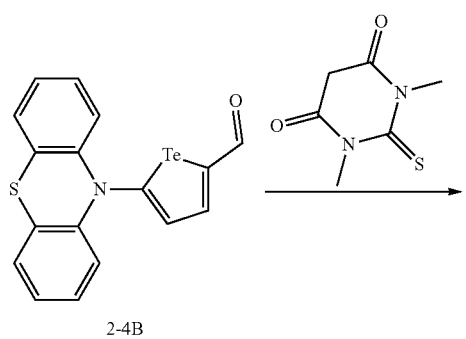

2-4B

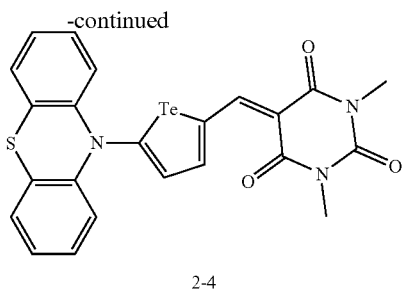

2-4

(i) Synthesis of Compound 2-4A 11.7 g (38.2 mmol) of 2-iodotellurophene and 6.3 g (31.8 mmol) of 10H-phenothiazine are heated under reflux in 150 ml of anhydrous toluene under the presence of 5 mol % of Pd(dba)$_2$, 5 mol % of P(tBu)$_3$, and 9.2 g (95.5 mmol) of NaOtBu for 2 hours. The obtained product is separated and purified through silica gel column chromatography (a volume ratio of toluene:hexane=1:4) to obtain 7.0 g (Yield 58.0%) of 10-(tellurophen-2-yl)-10H-phenothiazine.

(ii) Synthesis of Compound 2-4B 1.6 ml (17.6 mmol) of phosphoryl chloride is added dropwise to 5.3 ml (67.9 mmol) of N,N-dimethylformamide at −15° C. and then, stirred at room temperature (24° C.) for 2 hours. The resultant is slowly added dropwise to a mixture of 200 ml of dichloromethane and 5.1 g (13.6 mmol) of Compound 2-4A at −15° C. and then, stirred at room temperature (24° C.) for 2 hours. Subsequently, 100 ml of water is added thereto, and an aqueous sodium hydroxide solution is added thereto, until the pH becomes 14 and then, stirred at room temperature (24° C.) for 2 hours. An organic layer extracted with dichloromethane is washed with an aqueous sodium chloride solution and then, dried by adding anhydrous magnesium sulfate thereto. The obtained product is separated and purified through silica gel column chromatography (a volume ratio of hexane:ethyl acetate=4:1) to obtain 3.5 g (Yield of 63.5%) of Compound 2-4B (5-(10H-phenothiazin-10-yl)tellurophene-2-carbaldehyde).

(iii) Synthesis of Compound Represented by Chemical Formula 2-4

1.09 g (2.7 mmol) of Compound 2-4B is suspended in ethanol, and 0.55 g (3.2 mmol) of 1,3-dimethyl-2-thioxodihydropyrimidine-4,6(1H,5H)-dione is added thereto and then, heated under reflux at 50° C. for 2 hours. The resultant is cooled down to room temperature (24° C.), and hexane is added thereto. When powder is formed therein, the powder is filtered and then, the product from the filtrate is separated and purified through silica gel column chromatography (dichloromethane) to obtain 1.30 g (Yield of 87.0%) of a compound represented by Chemical Formula 2-4. The obtained compound is purified through sublimation up to purity of 99.9%.

1H-NMR (500 MHz, Methylene Chloride-d2): δ 8.50 (s, 1H), 8.31 (d, 1H), 7.81 (d, 2H), 7.48 (t, 2H), 7.55 (d, 2H), 7.36 (d, 2H), 7.04 (1, 2H), 3.7 (d, 6H).

Reference Synthesis Example 5: Synthesis of Compound Represented by Chemical Formula 2-5

[Chemical Formula 2-5]

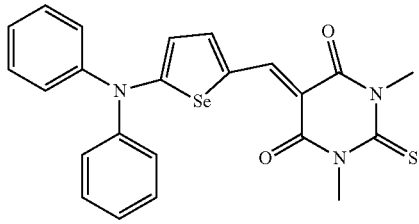

[Reaction Scheme 2-5]

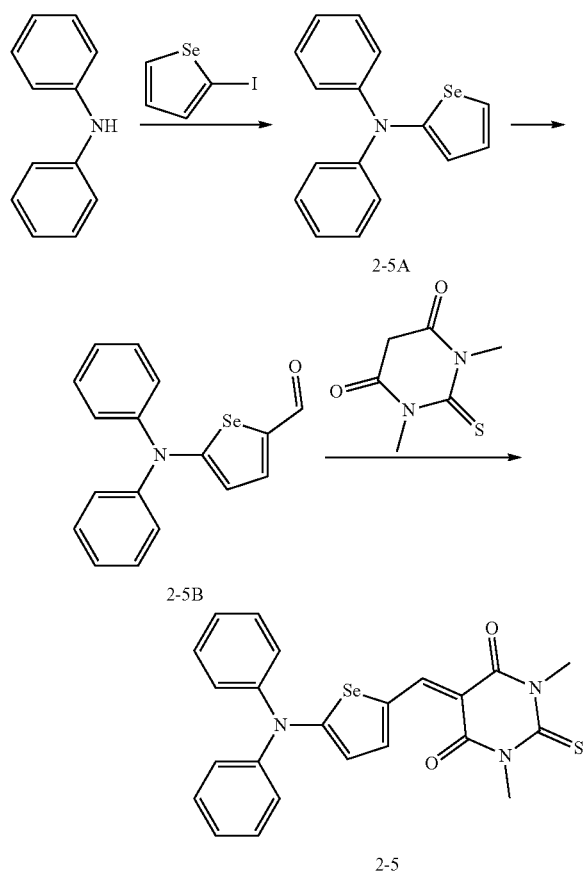

(i) Synthesis of Compound 2-5A 2.0 g (7.80 mmol) of 2-iodoselenophene (Compound 1) and 1.2 g (7.09 mmol) of diphenylamine are heated under reflux in 30 ml of anhydrous toluene under the presence of 5 mol % of Pd(dba)$_2$, 5 mol % of P(tBu)$_3$, and 0.75 g (7.80 mmol) of NaOtBu for 2 hours. The obtained product is separated and purified through silica gel column chromatography (a volume ratio of toluene:hexane=1:4) to obtain 1.40 g (Yield of 66.2%) of Compound 2-5A.

(ii) Synthesis of Compound 2-5B 1.75 ml of phosphoryl chloride is added dropwise to 6.0 ml of N,N-dimethylformamide at −15° C. and then, stirred at room temperature (24° C.) for 2 hours. The obtained mixture is slowly added dropwise to a mixture of 60 ml of dichloromethane and 1.4 g of Compound 2-5A at −15° C. and then, stirred at room temperature (24° C.) for 30 minutes and concentrated under a reduced pressure. 100 ml of water is added thereto, and an aqueous sodium hydroxide solution is added thereto until the pH becomes 14 and then, stirred at room temperature (24° C.) for 2 hours. An organic layer extracted with dichloromethane is washed with an aqueous sodium chloride solution and then, dried by adding anhydrous magnesium sulfate thereto. The obtained product is separated and purified through silica gel column chromatography (a volume ratio of hexane:ethyl acetate=4:1) to obtain 1.0 g (Yield of 65.3%) of Compound 2-5B.

(iii) Synthesis of Compound Represented by Chemical Formula 2-5

0.33 g (1.09 mmol) of Compound 2-5B is suspended in ethanol, and 0.23 g (1.3 mmol) of 1,3-dimethyl-2-thioxodihydropyrimidine-4,6(1H,5H)-dione is added thereto and then, reacted at 50° C. for 2 hours to obtain 0.47 g (Yield of 90%) of a compound represented by Chemical Formula 2-5.

$^1$H-NMR (500 MHz, Methylene Chloride-d2): 8.5 (s, 1H), 7.9 (d, 1H), 7.5-7.3 (m, 10H), 6.6 (d, 1H), 3.7 (d, 6H)

Example 1: Production of Photoelectric Device

ITO is deposited through sputtering on a glass substrate to form an about 150 nm-thick anode, and the ITO glass substrate is ultrasonic wave-cleaned under in acetone/isopropyl alcohol/pure water respectively for 15 minutes and then, UV ozone-cleaned. Subsequently, the compound of Synthesis Example 1 and C60 are codeposited in a volume ratio of 1:1 on the ITO glass substrate to form a 1000 nm-thick active layer, and Al is vacuum-deposited thereon to be 70 nm thick to produce a photoelectric device having a structure of ITO (150 nm)/active layer (1000 nm)/A (70 nm).

Examples 2 to 4 and Reference Examples 1 to 5: Production of Photoelectric Device Photoelectric devices of Examples 2 to 4 are produced according to the same method as Example 1 except that each of compounds of Synthesis Examples 2 to 4 and Reference Synthesis Examples 1 to 5 are respectively used instead of the compound of Synthesis Example 1.

Evaluation 1: Light Absorption Characteristics of Compounds

Light absorption characteristics (maximum absorption wavelength, full width at half maximum (FWHM), and absorption coefficient per thickness of thin film) of the compounds of Synthesis Examples 1 to 4 depending on a wavelength are evaluated. Each compound of Synthesis Examples 1 to 4 (a p-type semiconductor) and C60 (an n-type semiconductor) are codeposited in a volume ratio of 1:1 to form thin films, and the light absorption characteristics of the thin films are evaluated by using Cary 5000 UV spectrometer (Varian Medical Systems, Inc.) in an ultraviolet-visible ray (UV-Vis) region. The results are shown in Table 1.

TABLE 1

| Compound | $\lambda_{max}$ (nm) | FWHM (nm) | Abs. coeff. ($10^4$ cm$^{-1}$) |
|---|---|---|---|
| Synthesis Example 1 | 532 | 85 | 7.65 |
| Synthesis Example 2 | 543 | 90 | 7.43 |

TABLE 1-continued

| Compound | $\lambda_{max}$ (nm) | FWHM (nm) | Abs. coeff. ($10^4$ cm$^{-1}$) |
|---|---|---|---|
| Synthesis Example 3 | 530 | 86 | 7.01 |
| Synthesis Example 4 | 542 | 91 | 6.98 |

Referring to Table 1, the compounds according to Synthesis Examples 1 to 4 exhibit a maximum absorption wavelength in a green wavelength region, a low full width at half maximum (FWHM), and a high absorption coefficient. Accordingly, the compounds according to Synthesis Examples 1 to 4 have high wavelength selectivity in the green wavelength region.

Evaluation 2: Planarity of Compounds

The compounds of Synthesis Example 1 to 4 and Reference Synthesis Examples 1 to 5 are respectively calculated with respect to a molecular skeleton of an energetically-optimized structure through Density Functional Theory (DFT), and in the corresponding skeleton, a ratio (Z/X) of the shortest length (Z) relative to the longest length (X) is calculated to obtain an aspect ratio. The results are shown in Table 2.

TABLE 2

| Compound | Aspect ratio (Z/X) |
|---|---|
| Synthesis Example 1 | 0.206 |
| Synthesis Example 2 | 0.199 |
| Synthesis Example 3 | 0.233 |
| Synthesis Example 4 | 0.221 |
| Reference Synthesis Example 1 | 0.406 |
| Reference Synthesis Example 2 | 0.424 |
| Reference Synthesis Example 3 | 0.368 |
| Reference Synthesis Example 4 | 0.401 |
| Reference Synthesis Example 5 | 0.383 |

Referring to Table 2, the compounds according to Synthesis Examples 1 to 4 exhibit a low aspect ratio compared with the compounds according to Reference Synthesis Examples 1 to 5. Accordingly, the compounds according to Synthesis Examples 1 to 4 maintain planarity.

Evaluation 3: Mobility Evaluation of Photoelectric Device

In order to evaluate mobility of photoelectric devices, light of 550 nm (a laser pulse (pulse width: 6 nm)) is radiated into photoelectric devices according to Examples 1 to 4 and Reference Examples 1 to 5, and a bias voltage (V) is applied thereto to measure photocurrents thereof. Time (t) where the photocurrents are maximized is measured and used to calculate the mobility (p) according to Equation 2.

$$\mu = \frac{T^2}{t \times V}$$ [Equation 2]

In Equation 2, T is a thickness of an active layer, t is time where a photocurrent is maximized, and V is an applied voltage.

The results are shown in Table 3.

TABLE 3

| Examples | Mobility (cm$^2$/V·sec) |
|---|---|
| Example 1 | $1.1 \times 10^{-5}$ |
| Example 2 | $1.0 \times 10^{-5}$ |
| Example 3 | $1.0 \times 10^{-5}$ |
| Example 4 | $1.0 \times 10^{-5}$ |
| Reference Example 1 | $0.1 \times 10^{-5}$ |
| Reference Example 2 | $0.1 \times 10^{-5}$ |
| Reference Example 3 | $0.2 \times 10^{-5}$ |
| Reference Example 4 | $0.2 \times 10^{-5}$ |
| Reference Example 5 | $0.2 \times 10^{-5}$ |

Referring to Table 3, the photoelectric devices of Examples 1 to 4 respectively including the compounds of Synthesis Examples 1 to 4 exhibit excellent mobility compared with the photoelectric devices of Reference Examples 1 to 5 respectively including the compounds of Reference Synthesis Examples 1 to 5.

While some example embodiments have been described, it is to be understood that inventive concepts are not limited to the disclosed embodiments, but, on the contrary, are intended to cover various modifications and equivalent arrangements included within the spirit and scope of the appended claims.

What is claimed is:

1. A compound represented by Chemical Formula 1:

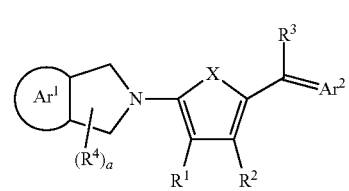

[Chemical Formula 1]

wherein, in Chemical Formula 1,
Ar$^1$ is a substituted or unsubstituted C6 to C30 arene group, a substituted or unsubstituted C3 to C30 heteroarene group, or a condensed ring thereof,
X is O, S, Se, Te, S(=O), S(=O)$_2$, NR$^a$, SiR$^b$R$^c$, GeR$^d$R$^e$, or CR$^f$R$^g$, wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure,
Ar$^2$ is a substituted or unsubstituted C6 to C30 hydrocarbon ring group having at least one functional group selected from C=O, C=S, C=Se, and C=Te, a substituted or unsubstituted C2 to C30 heterocyclic group having at least one functional group selected from C=O, C=S, C=Se, and C=Te, or a fused ring group thereof,
R$^1$ to R$^3$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, a pentafluorosulfanyl group (—SF$_5$), a hydroxyl group, an amine group, a hydrazine group, a hydrazone group, a carboxyl group or a salt thereof, a sulfonic acid group or a salt thereof, a phosphoric acid group or a salt thereof, —SiR$^a$R$^b$R$^c$, or a combination thereof, wherein R$^a$, R$^b$ and R$^c$ are independently hydrogen or a substituted or unsubstituted C1 to C10 alkyl group, R$^4$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a is an integer of 0 to 4.

2. The compound of claim 1, wherein the compound is represented by Chemical Formula 2-1:

[Chemical Formula 2-1]

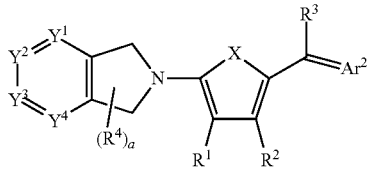

wherein, in Chemical Formula 2-1,

Y$^1$ to Y$^4$ are independently N or CR$^p$, wherein R$^p$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group or adjacent CR$^p$'s are linked to each other to form a substituted or unsubstituted C6 to C30 arene group, a substituted or unsubstituted C3 to C30 heteroarene group, or a condensed ring thereof, X is O, S, Se, Te, S(=O), S(=O)$_2$, NR$^a$, SiR$^b$R$^c$, GeR$^d$R$^e$, or CR$^f$R$^g$, wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure, Ar$^2$ is a substituted or unsubstituted C6 to C30 hydrocarbon ring group having at least one functional group selected from C=O, C=S, C=Se, and C=Te, a substituted or unsubstituted C2 to C30 heterocyclic group having at least one functional group selected from C=O, C=S, C=Se, and C=Te, or a fused ring group thereof, R$^1$ to R$^3$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, a pentafluorosulfanyl group (—SF$_5$), a hydroxyl group, an amine group, a hydrazine group, a hydrazone group, a carboxyl group or a salt thereof, a sulfonic acid group or a salt thereof, a phosphoric acid group or a salt thereof, —SiR$^a$R$^b$R$^c$, or a combination thereof, wherein R$^a$, R$^b$ and R$^c$ are independently hydrogen or a substituted or unsubstituted C1 to C10 alkyl group, R$^4$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a is an integer of 0 to 4.

3. The compound of claim 2, wherein the compound is represented by one of Chemical Formulas 2-1A to 2-1E:

[Chemical Formula 2-1A]

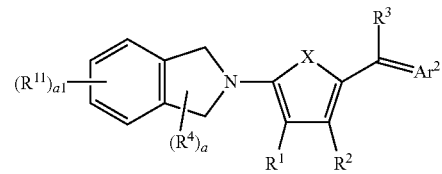

wherein, in Chemical Formula 2-1A,

X, Ar$^2$, R$^1$ to R$^4$, and a are the same as in claim 2,

R$^{11}$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 is an integer of 0 to 4,

[Chemical Formula 2-1B]

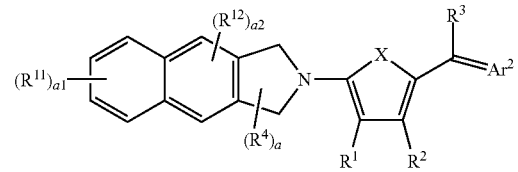

wherein, in Chemical Formula 2-1B,

X, Ar$^2$, R$^1$ to R$^4$, and a are the same as in claim 2,

R$^{11}$ and R$^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a1 is an integer of 0 to 4, and a2 is an integer of 0 to 2,

[Chemical Formula 2-1C]

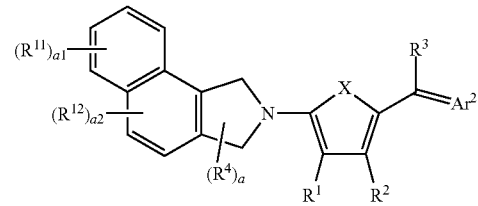

wherein, in Chemical Formula 2-1C,

X, Ar$^2$, R$^1$ to R$^4$, and a are the same as in claim 2,

R$^{11}$ and R$^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group,
a1 is an integer of 0 to 4, and
a2 is an integer of 0 to 2,

[Chemical Formula 2-1D]

![Chemical Formula 2-1D structure]

wherein, in Chemical Formula 2-1D,
X, $Ar^2$, $R^1$ to $R^4$, and a are the same as in claim 2,
$R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and
a1 and a2 are independently an integer of 0 to 4,

[Chemical Formula 2-1E]

![Chemical Formula 2-1E structure]

wherein, in Chemical Formula 2-1E,
X, $Ar^2$, $R^1$ to $R^4$, and a are the same as in claim 2,
$X^1$ is O, S, Se, Te, S(=O), S(=O)$_2$, NR$^a$, SiR$^b$R$^c$, GeR$^d$R$^e$, or CR$^f$R$^g$, wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure,
$R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and
a1 and a2 are independently an integer of 0 to 2.

4. The compound of claim 1, wherein the compound is represented by Chemical Formula 2-2:

[Chemical Formula 2-2]

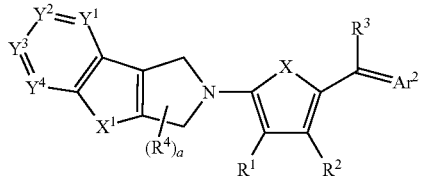

wherein, in Chemical Formula 2-2,
X is O, S, Se, Te, S(=O), S(=O)$_2$, NR$^a$, SiR$^b$R$^c$, GeR$^d$R$^e$, or CR$^f$R$^g$, wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure,
$X^1$ is O, S, Se, Te, S(=O), S(=O)$_2$, NR$^a$, SiR$^b$R$^c$, GeR$^d$R$^e$, or CR$^f$R$^g$, wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure,
$Ar^2$ is a substituted or unsubstituted C6 to C30 hydrocarbon ring group having at least one functional group selected from C=O, C=S, C=Se, and C=Te, a substituted or unsubstituted C2 to C30 heterocyclic group having at least one functional group selected from C=O, C=S, C=Se, and C=Te, or a fused ring group thereof,
$R^1$ to $R^3$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, a pentafluorosulfanyl group (—SF$_5$), a hydroxyl group, an amine group, a hydrazine group, a hydrazone group, a carboxyl group or a salt thereof, a sulfonic acid group or a salt thereof, a phosphoric acid group or a salt thereof, —SiR$^a$R$^b$R$^c$, or a combination thereof, wherein R$^a$, R$^b$ and R$^c$ are independently hydrogen or a substituted or unsubstituted C1 to C10 alkyl group,
$R^4$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group,
a is an integer of 0 to 4, and
$Y^1$ to $Y^4$ are independently N or CR$^p$, wherein R$^p$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group or adjacent CR$^p$'s are linked to each other to form a substituted or unsubstituted C6 to C30 arene group, a substituted or unsubstituted C3 to C30 heteroarene group, or a condensed ring thereof.

5. The compound of claim 4, wherein the compound is represented by one of Chemical Formulas 2-2A to 2-2J:

[Chemical Formula 2-2A]

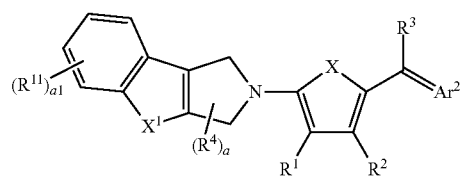

wherein, in Chemical Formula 2-2A,

X, $X^1$, $Ar^2$, $R^1$ to $R^4$, and a are the same as in claim 4, $R^{11}$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 is an integer of 0 to 4,

[Chemical Formula 2-2B]

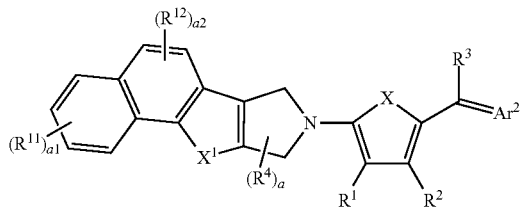

wherein, in Chemical Formula 2-2B,

X, $X^1$, $Ar^2$, $R^1$ to $R^4$, and a are the same as in claim 4, $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a1 is an integer of 0 to 4, and a2 is an integer of 0 to 2,

[Chemical Formula 2-2C]

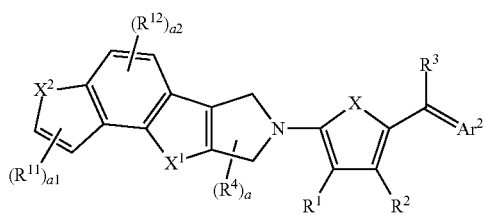

wherein, in Chemical Formula 2-2C,

X, $X^1$, $Ar^2$, $R^1$ to $R^4$, and a are the same as in claim 4, $X^2$ is O, S, Se, Te, S(=O), S(=O)$_2$, $NR^a$, $SiR^bR^c$, $GeR^dR^e$, or $CR^fR^g$, wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure, $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer of 0 to 2,

[Chemical Formula 2-2D]

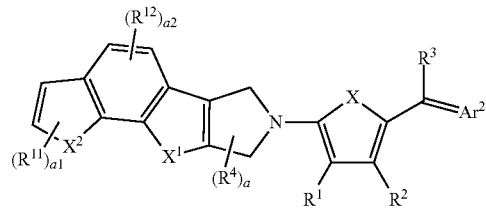

wherein, in Chemical Formula 2-2D,

X, $X^1$, $Ar^2$, $R^1$ to $R^4$, and a are the same as in claim 4, $X^2$ is O, S, Se, Te, S(=O), S(=O)$_2$, $NR^a$, $SiR^bR^c$, $GeR^dR^e$, or $CR^fR^g$, wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure, $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer of 0 to 2,

[Chemical Formula 2-2E]

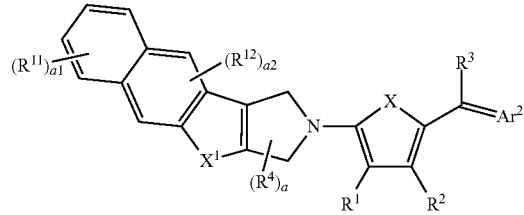

wherein, in Chemical Formula 2-2E,

X, $X^1$, $Ar^2$, $R^1$ to $R^4$, and a are the same as in claim 4, $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a1 is an integer of 0 to 4, and a2 is an integer of 0 to 2,

[Chemical Formula 2-2F]

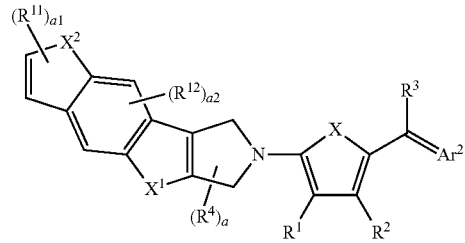

wherein, in Chemical Formula 2-2F,

X, $X^1$, $Ar^2$, $R^1$ to $R^4$, and a are the same as in claim 4, $X^2$ is O, S, Se, Te, S(=O), S(=O)$_2$, $NR^a$, $SiR^bR^c$, $GeR^dR^e$, or $CR^fR^g$, wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R_g$ are linked to each other to form a spiro structure, $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer of 0 to 2,

[Chemical Formula 2-2G]

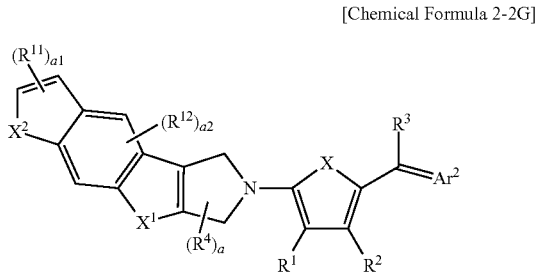

wherein, in Chemical Formula 2-2G,

X, $X^1$, $Ar^2$, $R^1$ to $R^4$, and a are the same as in claim 4, $X^2$ is O, S, Se, Te, S(=O), S(=O)$_2$, $NR^a$, $SiR^bR^c$, $GeR^dR^e$, or $CR^fR^g$, wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure, $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer of 0 to 2,

[Chemical Formula 2-2H]

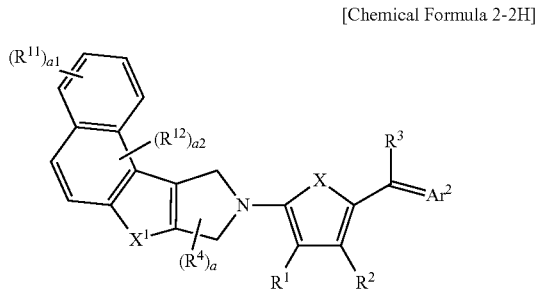

wherein, in Chemical Formula 2-2H,

X, $X^1$, $Ar^2$, $R^1$ to $R^4$, and a are the same as in claim 4, $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, a1 is an integer of 0 to 4, and a2 is an integer of 0 to 2,

[Chemical Formula 2-2I]

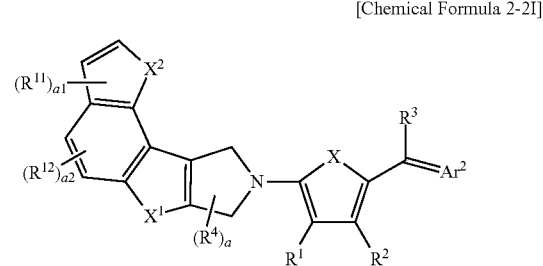

wherein, in Chemical Formula 2-2I,

X, $X^1$, $Ar^2$, $R^1$ to $R^4$, and a are the same as in claim 4, $X^2$ is O, S, Se, Te, S(=O), S(=O)$_2$, $NR^a$, $SiR^bR^c$, $GeR^dR^e$, or $CR^fR^g$, wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure, $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer of 0 to 2,

[Chemical Formula 2-2J]

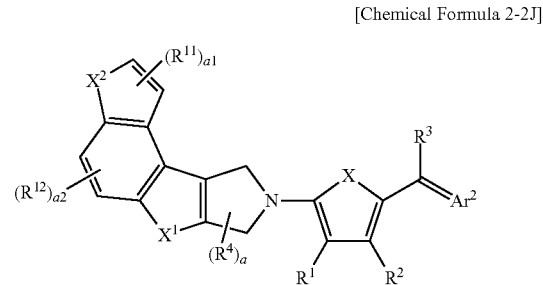

wherein, in Chemical Formula 2-2J,

X, $X^1$, $Ar^2$, $R^1$ to $R^4$, and a are the same as in claim 4, $X^2$ is O, S, Se, Te, S(=O), S(=O)$_2$, $NR^a$, $SiR^bR^c$, $GeR^dR^e$, or $CR^fR^g$, wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure, $R^{11}$ and $R^{12}$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and a1 and a2 are independently an integer of 0 to 2.

6. The compound of claim 1, wherein the compound is represented by Chemical Formula 2-3:

[Chemical Formula 2-3]

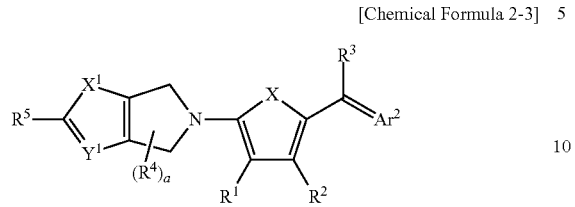

wherein, in Chemical Formula 2-3,
- X is O, S, Se, Te, S(=O), S(=O)$_2$, NR$^a$, SiR$^b$R$^c$, GeR$^d$R$^e$, or CR$^f$R$^g$, wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure,
- X$^1$ is O, S, Se, Te, S(=O), S(=O)$_2$, NR$^a$, SiR$^b$R$^c$, GeR$^d$R$^e$, or CR$^f$R$^g$, wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure,
- Ar$^2$ is a substituted or unsubstituted C6 to C30 hydrocarbon ring group having at least one functional group selected from C=O, C=S, C=Se, and C=Te, a substituted or unsubstituted C2 to C30 heterocyclic group having at least one functional group selected from C=O, C=S, C=Se, and C=Te, or a fused ring group thereof,
- R$^1$ to R$^3$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, a pentafluorosulfanyl group (—SF$_5$), a hydroxyl group, an amine group, a hydrazine group, a hydrazone group, a carboxyl group or a salt thereof, a sulfonic acid group or a salt thereof, a phosphoric acid group or a salt thereof, —SiR$^a$R$^b$R$^c$ or a combination thereof, wherein R$^a$, R$^b$, and R$^c$ are independently hydrogen or a substituted or unsubstituted C1 to C10 alkyl group,
- R$^4$ and R$^5$ are independently hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group,
- a is an integer of 0 to 4, and
- Y$^1$ is N or CR$^p$, wherein R$^p$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group or R$^p$ and R$^5$ are linked to each other to form a substituted or unsubstituted C6 to C30 arene group, a substituted or unsubstituted C3 to C30 heteroarene group, or a condensed ring thereof.

7. The compound of claim 6, wherein the compound is represented by one of Chemical Formulas 2-3A to 2-3D:

[Chemical Formula 2-3A]

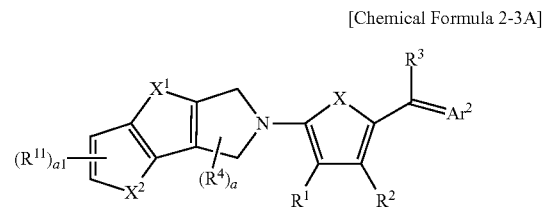

wherein, in Chemical Formula 2-3A,
- X, X$^1$, Ar$^2$, R$^1$ to R$^4$, and a are the same as in claim 6,
- X$^2$ is O, S, Se, Te, S(=O), S(=O)$_2$, NR$^a$, SiR$^b$R$^c$, GeR$^d$R$^e$, or CR$^f$R$^g$, wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure,
- R$^{11}$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and
- a1 is an integer of 0 to 2,

[Chemical Formula 2-3B]

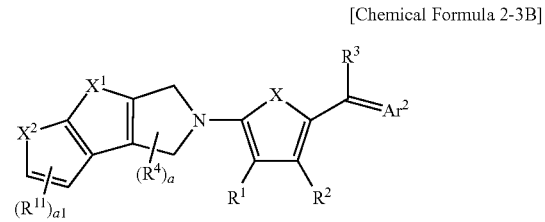

wherein, in Chemical Formula 2-3B,
- X, X$^1$, Ar$^2$, R$^1$ to R$^4$, and a are the same as in claim 6,
- X$^2$ is O, S, Se, Te, S(=O), S(=O)$_2$, NR$^a$, SiR$^b$R$^c$, GeR$^d$R$^e$, or CR$^f$R$^g$, wherein R$^a$, R$^b$, R$^c$, R$^d$, R$^e$, R$^f$, and R$^g$ are independently hydrogen, a substituted or unsubstituted C1 to C10 alkyl group, or a substituted or unsubstituted C6 to C10 aryl group, wherein R$^b$, R$^c$, R$^d$, R$^e$, R$^f$, and R$^g$ are independently present or at least one pair selected from R$^b$ and R$^c$, R$^d$ and R$^e$, and R$^f$ and R$^g$ are linked to each other to form a spiro structure,
- R$^{11}$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, and
- a1 is an integer of 0 to 2,

[Chemical Formula 2-3C]

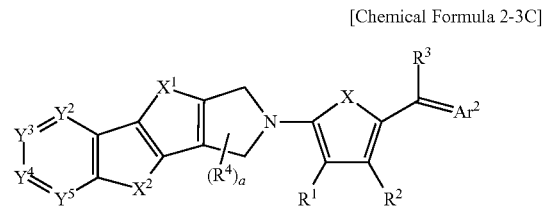

wherein, in Chemical Formula 2-3C,

X, $X^1$, $Ar^2$, $R^1$ to $R^4$, and a are the same as in claim 6, $X^2$ is O, S, Se, Te, S(=O), S(=O)$_2$, $NR^a$, $SiR^bR^c$, $GeR^dR^e$, or $CR^fR^g$, wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure, and $Y^2$ to $Y^5$ are independently N or $CR^p$, wherein $R^p$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group or adjacent $CR^p$'s are linked to each other to form a substituted or unsubstituted C6 to C30 arene group, a substituted or unsubstituted C3 to C30 heteroarene group, or a condensed ring thereof,

[Chemical Formula 2-3D]

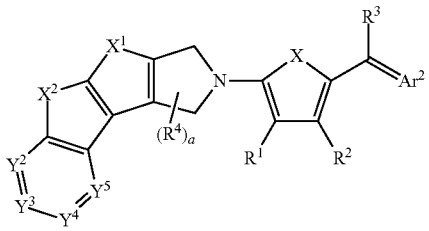

wherein, in Chemical Formula 2-3D,

X, $X^1$, $Ar^2$, $R^1$ to $R^4$, and a are the same as in claim 6, $X^2$ is O, S, Se, Te, S(=O), S(=O)$_2$, $NR^a$, $SiR^bR^c$, $GeR^dR^e$, or $CR^fR^g$, wherein $R^a$, $R^b$, $R^c$, $R^d$, $R^e$, $R^f$, and $R^g$ are independently hydrogen, a substituted or unsubstituted C1 to C10 alkyl group, or a substituted or unsubstituted C6 to C10 aryl group, wherein $R^b$, $R^c$, $R^d$, $R^e$, $R^f$, and $R^g$ are independently present or at least one pair selected from $R^b$ and $R^c$, $R^d$ and $R^e$, and $R^f$ and $R^g$ are linked to each other to form a spiro structure, and $Y^2$ to $Y^5$ are independently N or $CR^p$, wherein $R^p$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group or adjacent $CR^p$'s are linked to each other to form a substituted or unsubstituted C6 to C30 arene group, a substituted or unsubstituted C3 to C30 heteroarene group, or a condensed ring thereof.

8. The compound of claim 1, wherein $Ar^2$ is a ring group represented by Chemical Formula 3:

[Chemical Formula 3]

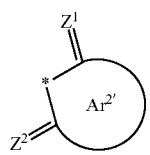

wherein, in Chemical Formula 3, $Ar^{2'}$ is a substituted or unsubstituted C6 to C30 aryl group or a substituted or unsubstituted C3 to C30 heteroaryl group, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group, and

* is a linking portion.

9. The compound of claim 1, wherein in Chemical Formula 1, $Ar^2$ is a ring group represented by one of Chemical Formulas 4A to 4F:

[Chemical Formula 4A]

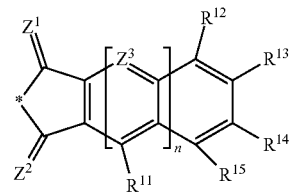

wherein, in Chemical Formula 4A, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group, $Z^3$ is N or $CR^c$, wherein $R^c$ is hydrogen, deuterium, or a substituted or unsubstituted C1 to C10 alkyl group, $R^{11}$, $R^{12}$, $R^{13}$, $R^{14}$, and $R^{15}$ are the same or different and are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group, a cyano-containing group, or a combination thereof, or $R^{12}$ and $R^{13}$ and/or $R^{14}$ and $R^{15}$ are independently linked to each other to form a fused aromatic ring, n is 0 or 1, and

* is a linking portion,

[Chemical Formula 4B]

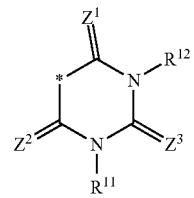

wherein, in Chemical Formula 4B, $Z^1$ is O, S, Se, or Te, $Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group, $Z^3$ is O, S, Se, Te, or $C(R^a)(CN)$, wherein $R^a$ is hydrogen, a cyano group (—CN), or a C1 to C10 alkyl group, $R^{11}$ and $R^{12}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and
* is a linking portion,

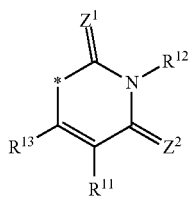
[Chemical Formula 4C]

wherein, in Chemical Formula 4C,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group,
$R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and
* is a linking portion,

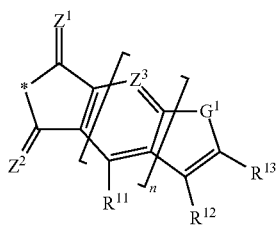
[Chemical Formula 4D]

wherein, in Chemical Formula 4D,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group,
$Z^3$ is N or $CR^c$, wherein $R^c$ is hydrogen or a substituted or unsubstituted C1 to C10 alkyl group,
$G^1$ is O, S, Se, Te, $SiR^xR^y$, or $GeR^zR^w$, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group,
$R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, wherein $R^{12}$ and $R^{13}$ are independently present or are linked to each other to form an aromatic ring,
n is 0 or 1, and
* is a linking portion,

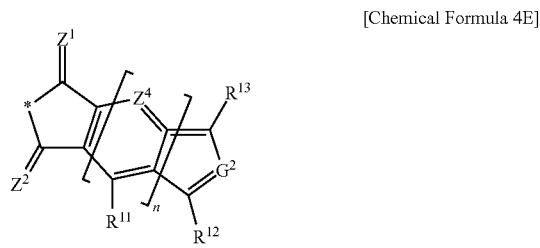
[Chemical Formula 4E]

wherein, in Chemical Formula 4E,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group,
$Z^4$ is $NR^a$, $CR^bR^c$, O, S, Se, Te, S(=O), S(=O)$_2$, $SiR^dR^e$, or $GeR^fR^g$, wherein $R^a$, $R^b$, $R^c$, $R^d$, $R^e$, $R^f$, and $R^g$ are independently hydrogen or a substituted or unsubstituted C1 to C10 alkyl group,
$G^2$ is O, S, Se, Te, $SiR^xR^y$, or $GeR^zR^q$, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group,
$R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof,
n is 0 or 1, and
* is a linking portion,

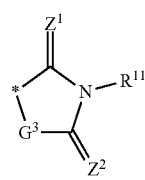
[Chemical Formula 4F]

wherein, in Chemical Formula 4F,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group,
$R^{11}$ is hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group, a cyano-containing group, or a combination thereof, and $G^3$ is O, S, Se, Te, $SiR^xR^y$, or $GeR^zR^w$, wherein $R^x$, $R^y$, $R^z$, and $R^w$ are the same or different and are independently hydrogen, a halogen, a substituted or unsubstituted C1 to C10 alkyl group, or a substituted or unsubstituted C6 to C10 aryl group.

10. The compound of claim 1, wherein $Ar^2$ is represented by one of Chemical Formulas 4A-1, 4A-2, or 4A-3,

[Chemical Formula 4A-1]

[Chemical Formula 4A-2]

[Chemical Formula 4A-3]

wherein in Chemical Formulas 4A-1 to 4A-3,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, and wherein when $Z^2$ is $CR^aR^b$, at least one of $R^a$ and $R^b$ is a cyano group or a cyano-containing group,
$Z^3$ is N or $CR^c$, wherein $R^c$ is hydrogen or a substituted or unsubstituted C1 to C10 alkyl group,
n is 0 or 1,
$R^{11}$, $R^{12}$, $R^{13}$, $R^{14}$, and $R^{15}$ are the same or different and are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group, a cyano-containing group, or a combination thereof, and
wherein in Chemical Formula 4A-3,
$R^{12a}$ and $R^{12b}$ are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof,
m1 and m2 are independently an integer of 0 to 4, and
$Ph^1$ and $Ph^2$ are a fused phenylene ring.

11. The compound of claim 9, wherein $Ar^2$ is the ring group represented by Chemical Formula 4B and $Ar^2$ is represented by one of Chemical Formulas 4B-1, 4B-2, or 4B-3,

[Chemical Formula 4B-1]

[Chemical Formula 4B-2]

[Chemical Formula 4B-3]

wherein, in Chemical Formulas 4B-1, 4B-2, and 4B-3, $R^{11}$ and $R^{12}$ are the same as in Chemical Formula 4B of claim 9.

12. The compound of claim 9, wherein $Ar^2$ is the ring group represented by Chemical Formula 4C and $Ar^2$ is represented by one of Chemical Formulas 4C-1 or 4C-2,

[Chemical Formula 4C-1]

[Chemical Formula 4C-2]

wherein, in Chemical Formulas 4C-1 and 4C-2, $R^{11}$ to $R^{13}$ are the same as in Chemical Formula 4C of claim 9.

13. The compound of claim 1, wherein the compound represented by Chemical Formula 1 has an aspect ratio (Z/X), obtained by dividing a shortest length (Z) by a longest length (X), in a range of less than or equal to about 0.30.

14. The compound of claim 1, wherein the compound has a maximum absorption wavelength ($\lambda_{max}$) in a wavelength range of greater than or equal to about 500 nm and less than or equal to about 590 nm in a thin film state.

15. The compound of claim 1, wherein the compound exhibits a light absorption curve having a full width at half maximum (FWHM) of about 50 nm to about 100 nm.

16. The compound of claim 1, wherein
the compound is a p-type semiconductor compound,
the p-type semiconductor compound has a HOMO energy level ranging from about 5.2 eV to about 5.8 eV and an energy bandgap ranging from about 2.12 eV to about 2.48 eV,
a LUMO energy level of the p-type semiconductor compound is in a range of about 3.8 eV to about 2.7 eV, and
the p-type semiconductor compound has a molecular weight of about 300 g/mol to about 1500 g/mol.

17. The compound of claim 1, wherein the compound is represented by Chemical Formula 1A or Chemical Formula 1B,

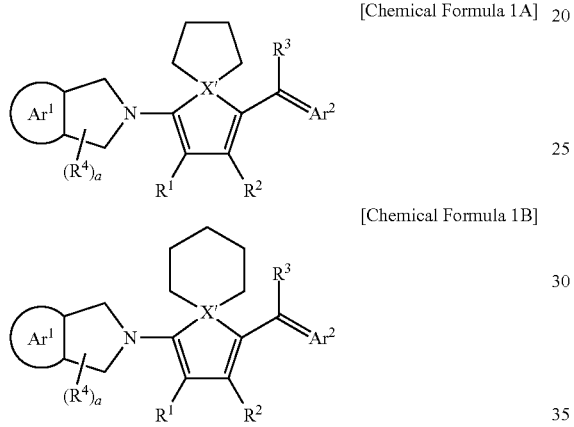

[Chemical Formula 1A]

[Chemical Formula 1B]

in Chemical Formulas 1A and 1B,
$Ar^1$, $Ar^2$, $R^1$ to $R^4$, and a are the same as in claim 1, and
X' is Si, Ge, or C.

18. A photoelectric device, comprising
a first electrode and a second electrode facing each other, and
an active layer between the first electrode and the second electrode,
wherein the active layer comprises the compound of claim 1.

19. An image sensor comprising:
the photoelectric device of claim 18.

20. The image sensor of claim 19, further comprising:
a semiconductor substrate integrated with a plurality of first photo-sensing devices configured to sense light in a blue wavelength region and a plurality of second photo-sensing devices configured to sense light in a red wavelength region, wherein
the photoelectric device is on the semiconductor substrate and configured to selectively sense light in a green wavelength region.

21. The image sensor of claim 20, further comprising:
a color filter layer comprising a blue filter configured to selectively transmit light in a blue wavelength region and a red filter configured to selectively transmit light in a red wavelength region.

22. The image sensor of claim 20, wherein the first photo-sensing devices and the second photo-sensing devices are stacked in a vertical direction in the semiconductor substrate.

23. The image sensor of claim 19, comprising:
a green photoelectric device including the photoelectric device, the green photoelectric device being an organic photoelectric device;
a blue photoelectric device configured to selectively absorb light in a blue wavelength region; and
a red photoelectric device configured to selectively absorb light in a red wavelength region,
wherein the green photoelectric device, the blue photoelectric device, and the red photoelectric device are stacked.

24. An electronic device comprising:
the image sensor of claim 19.

* * * * *